(12) United States Patent
Felden

(10) Patent No.: US 7,611,843 B2
(45) Date of Patent: Nov. 3, 2009

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

( * ) Notice: Subject to any disclaimer, the term of this patent is extended or adjusted under 35 U.S.C. 154(b) by 348 days.

(21) Appl. No.: 11/329,230

(22) Filed: Jan. 11, 2006

(65) Prior Publication Data
US 2006/0216733 A1  Sep. 28, 2006

Related U.S. Application Data

(62) Division of application No. 09/958,206, filed as application No. PCT/US00/08988 on Apr. 6, 2000, now Pat. No. 7,115,366.

(60) Provisional application No. 60/128,058, filed on Apr. 7, 1999.

(51) Int. Cl.
*C12Q 1/68* (2006.01)
*C12P 19/34* (2006.01)
*C07H 21/02* (2006.01)
*C07H 21/04* (2006.01)
*A61K 31/70* (2006.01)
*A01N 43/04* (2006.01)

(52) U.S. Cl. .................... 435/6; 435/91.1; 435/91.2; 536/23.1; 536/23.7; 514/44

(58) Field of Classification Search .................. None
See application file for complete search history.

(56) References Cited

FOREIGN PATENT DOCUMENTS

EP  786519 A2 *  7/1997

OTHER PUBLICATIONS

B. Felden et al., "Eubacterial tmRNAs: everywhere except the alpha-Proteobacteria?" Biochimica et Biophysica Acta 1446:145-148, 1999.
N. Nameki et al., "Three of four pseudoknots in tmRNA are interchangeable and are substitutable with single-stranded RNAs," FEBS Lett 470(3):345-349, Mar. 31, 2000.
N. Nameki et al., "Functional and structural analysis of a pseudoknot upstream of the tag-encoded sequence in *E. coli* tmRNA," J. Mol. Biol 286(3):733-744, Feb. 26, 1999.
W. Schönhuber et al., "Utilization of tmRNA squences for bacterial identification," MBC Microbiology 2001, 1:20 (online, 8 pages).
K.P. Williams et al., "Phylogenetic analysis of tmRNA secondary structure," RNA 2:1306-1310, 1996.
C. Zwieb et al., "Survey and Summary, Comparative sequence analysis of tmRNA," Nucleic Acids Research 27(10):2063-2071, 1999.

\* cited by examiner

*Primary Examiner*—Janet L. Epps-Smith
(74) *Attorney, Agent, or Firm*—Rothwell, Figg, Ernst & Manbeck p.c.

(57) ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

3 Claims, 24 Drawing Sheets

```
                    H1                      H5              H2
             ⑤'  ══              ═══════════════    ══
Tab.saccha   *********-**********CGGGGGUAGUAGAGGUAAAAGUAGCGAGC
C.acetobut   *********-************************************
C.stercora   *********-**********CGGGGUUAU-UGAAGCAAGAGUAGCGGGU
C.perfrige   *********-**********CGGGGGUAAGAUGGGUUUGAUAAGCGAGU
C.lentocel   *********-**********CGGGGGUCACAUCUACUGGGGCAGCCAUC
Hlb.mobili   *********-**********CGGGGAACGUGUUUGCUUGGGAUGCGAGC
Hsp.gestii   *********-**********CGGGGAACGUGUUUGCUUAGGACGCGAGC
Bb.brevis    *********-**********CGGGGAUGG-UAGAGCAUGAGAAGCGAGC
B.subtilis   GGGGACGUU-ACGGAUUCGACAGGGAUGGAUCGAGCUUGAGCUGCGAGC
B.badius     *********-**********CAGGGAUAGUUCGAGCUUGGGCUGCGAGC
B.megateri   ggggacguu-acggauucgacAGGG-UAGUUCGAGCUUAGGUUGCGAGU
B.thermole   *********-**********CGGGGGUAGGUCGAGCUUAAGCGGCGAGC
Eco.fecium   *********-**********CAGGCACAGUUUGAGCUUGAAUUGCGUUU
Eco.faecal   GGGGGCGUU-ACGGAUUCGACAGGCAUAG-UUGAGCUUGAAUUGCGUUU
Stc.pyogen   GGGGUUGUU-ACGGAUUCGACAGGCAUUA-UGAGGCAUGUUUUGCGUCC
Stc.pneumo   GGGGUCGUU-ACGGAUUCGACAGGCAUUA-UGAGGCAUAUUUUGCGACU
Stc.gordon   GGGGUCGUU-ACGGAUUCGACAGGCAUUA-UGAGGCAUAUUUUGCGACU
Stc.mutans   GGGGUCGUU-ACGGAUUCGACAGGCAUUA-UGAGACCUAUUUUGCGACU
Stp.epider   *********-**********CAGGGGUCC-CGAGCUUAUUAAGCGUGU
Stp.aureuT   GGGGACGUUCAUGGAUUCGACAGGGGUCCCCGAGCUCAUUAAGCGUGU
L.acidophi   *********-**********CAGGCGUAG-ACCCGCAUUGACUGCGGUU
             ▭ ▬▬ ▭ ▬▬ ▭ ▬▬ ▭ ▬▬▬▬ ← PK1
Tab.saccha   CGAGGU--UCCAUCUG-CUCG-UAAA-ACGGUGGAC---UUAAAU
C.acetobut   **********-*****-****-****-*********---******
C.stercora   AGAGGAUUCUCGUUGGCCUCU-UUAA-AAAACGAGA--GCUAAAA
C.perfrige   CGAGGGAAGCAUGGUGCCUCGAUAAUAAAGUAUGCA---UUAAAG
C.lentocel   CGUAGAACGCCGGAGUCUACG-UUAA-AAGCUGGCA---CUUAAA
Hlb.mobili   CGGGUUG--CCGCCAGGACCG-UAAA--AAGGGCGG---AAGGCU
Hsp.gestii   CGGGUUG--CCGCCAGGACCG-UAAA--AAGGGCGG---AAGGCU
Bb.brevis    CGGGGGG--UUGCGGACCUCG-UCAC--CAACGCAA---ACGCCA
B.subtilis   CGAGA-----GGCG-AUCUCG-UAAA---CACGCAC---UUAAAU
B.badius     CGGAG-----GGCCGUCUUCG-U-AC-CAACGCAAACGCCUAAAU
B.megateri   CGAGG-----AGAUGGCCUCG-UUAA--AACAUCAA-CGCCAAUA
B.thermole   CGAGG-----GGGACGUCCUCG-UAAA--AACGUCAC---CUAAAG
Eco.fecium   CGUAG----GUUACGUCUACG-UUAAAACGUUACAG---UUAAAU
Eco.faecal   CGUAG----GUUACGGCUACG-UUAAAACGUUACAG---UUAAAU
Stc.pyogen   CAUC--------GGCAGAUG-UAAA---UUGCCAG---UUAAAU
Stc.pneumo   CGU---------GUGGCGACG-UAAA---CGCUCAG---UUAAAU
Stc.gordon   CAUC-------UAGCGGAUG-UAAA---ACGCCAG---UUAAAU
Stc.mutans   CAUC-------UAGCGGAUG-UAAA---ACGCCAG---UUAAAU
Stp.epider   CGGAG-----GGUUGGCUCCG-UCAUCAACACAUUUCGGUUAAAU
Stp.aureus   CGGAG-----GGUUGUCUUCG-UCAUCAACACACACAGUUUAUA-
L.acidophi   CGUAG----GUUACGUCUACG-UAAAAACGUUACAG---UUAAAU
```

FIG. 3A

```
                    ┌─ CODING SEQUENCE                                    H4
                    ▼                                                ┌──────────┐
Tab.saccha   AUAAAC|gcaaacgauaau--------------uuagcuuacgcugcuUAA|UUA-CAAGCAGC---
C.acetobut   ******|************-------------*******************|***********---
C.stercora   AUAAAC|gcaaacaacgauaacuac--------gcuuuagcugcugcgUAA|GUAACACGCAGCC--
C.perfrige   AUAAAC|gcagaagauaau--------------uuugcauuagcagcuUAA|UUUAGCGCUGCU---
C.lentocel   GUAAAC|gcugaagauaau--------------uuagcaaucgcugccUAA|UUA-AGGC-GC----
Hlb.mobili   UUAAUU|gccgaagauaac--------------uacgcuuuagcugcuUUA|UUGCAGUCUAA----
Hsp.gestii   UUAAUU|gccgaagauaac--------------uacgcuuuagcugcuUUA|UUGCAGUCUAA----
Bb.brevis    UUAACU|ggcaacaaacaa--------------cuuucucucgcugcuUAA|UAACCAGUGAG----
B.subtilis   AUAACU|ggcaaaacuaacaguuuuaaccaaaacguagcauuagcugccUAA|UAAGCGCAGCGA---
B.badius     AUAACU|ggcaaaaaagau--------------uuagcuuuagcugccUAA|UAUAGGUUCAGCU--
B.megateri   AUAACU|ggcaaaucuaacaauaac--------uucgcuuuagcugcaUAA|UAGUAGCUUAGC---
B.thermole   AUAACU|ggcaaacaaaac--------------uacgcuuuagcugccUAA|UUGCUGCAGCUA---
Eco.fecium   AUAACU|gcuaaaaacgaaaacaacucu------uacgcuuuagcugccUAA|AAA-CAGUUAGCGUA
Eco.faecal   AUAACU|gcuaaaaacgaaaacaauucu------uucgcuuuagcugccUAA|AAACCAGCUAGCGAA
Stc.pyogen   AUAACU|gcaaaaaauacaaacucu---------uacgcuuuagcugccUAA|AAACCAGCUAGCGU-
Stc.pneumo   AUAACU|gcaaaaaauaaacacuucu--------uacgcucuagcugccUAA|AAACCAGCAGGCGU-
Stc.gordon   AUAACU|gcaaaaaauaauacuucu---------uacgcuuuagcugccUAA|AAACCAGCGGGCGU-
Stc.mutans   AUAACU|gcaaaaaauacaaauucu---------uacgcaguagcugccUAA|AAACCAGCCUGUGU-
Stp.epider   AUAACU|gacaaaucaaacaauaau---------uucgcaguagcugcgUAA|UAGCCACUGC-----
Stp.aureus   AUAACU|ggcaaaucaaacaauaau---------uucgcaguagcugccUAA|UCGCA-CU-CUGC--
L.acidophi   AUAACU|gcaaauaacaaaaauucu---------uacgcauuagcugcuUAA|UUUAGCGCAUGCGU- Tab.saccha   CGUUCAA-CCUU-UGAU-UCCCAC--AUCA-AAGGAUUGGGCGUCG--AUUUAGUGGGG
C.acetobut   ********-*******--*AAUCUGGCGUCG----AGAGCGGGG
C.stercora   CGUCGG-C-CCCCGGGGUUCCUGC---GCCUCGGGAUACCGGCGUCA---UCAAGGCAGG
C.perfrige   CAUCCUU--CCU-CAAUUGCCCACG-GUUG-AGAGUAAGGGUGUCAUUUAAAAGUGGGG
C.lentocel   AGUCCU----CCU-AGGUCUUCCGCA-GCCU-AGAUC-AGGGCUUCG---ACUCGCGGAU
Hlb.mobili   CCUCUU-C-UCC-UC-UGUGCUCUCGGUGA-GGAUGUAAGGGGUCA-UUUAAGAGAGCU
Hsp.gestii   CCUCUU-C-UCC-UC-UGUGCUCUCGGUGA-GGAUGUAAGGGGUCA-UUUAAGAGAGCU
Bb.brevis    GCUCUC-CCACU-GCAUCGGCCCGU-GUGC-CGUGGAUAGGGCUCAACUUUAACGGGCU
B.subtilis   GCUCUUC--CUG-ACAU-UGCCUAU-GUGU-CUGU-GAAGAGCACA-UCCAAGUAGGCU
B.badius     GCUCCU--CCCG-CUAU-CGUCCAU-GUAGUCGGGUAAGGGGUCCAAACUUAGUGGACU
B.megateri   GUUCCU--CCCU-CCAU-CGCCCAU-GUGGUAGGGUAAGGGACUCACUUUAAGUGGGCU
B.thermole   GCUCCUC--CCG-CCAU-CGCCCGC-GUGG-CGUUCGAGGGCUCAUAUGGAGCGGGCU
Eco.fecium   GAUCCU--CUCG-GCAU-CGCCCAU-GUGCUCGAGUAAGGGUCUCAAAUUUAGUGGGAU
Eco.faecal   GAUCCU--CCCG-GCAU-CGCCCAU-GUGCUCGGGUCAGGGUCCUAAUCGAAGUGGGAU
Stc.pyogen   GACUUCU--ACA-AGAU-UGCUUGU-GUCC-UGUU-AGAAGUC-UCAAAAUAGCAAGCU
Stc.pneumo   GACCC--GAUUU-GGAU-UGCUCGU-GUUC-AAUGA-CAGGUCUUAUAUUAGCGAGAU
Stc.gordon   GACCC--GAUUC-GGAU-UGCUUGU-GUCU-GAUGA-CAGGUCUUAUAUUAGCAAGCU
Stc.mutans   GAUCAAU--AAC-AAAU-UGCUUGU-GUUU-GUUG-AUUGGUCUUAUUGUUAACAAGCU
Stp.epider   AUCGCC-UAACA-GCAU-CUCCUAC-GUGC-UGUUAACGCGAUUCAACCCUAGUAGGAU
Stp.aureus   AUCGCC-UAACA-GCAU-UUCCUAU-GUGC-UGUUAACGCGAUUCAACCUUAAUAGGAU
L.acidophi   UGCUCU-UUGUC-GGUU-UACUCGU-GGCU-GACAC-UGAGUAUCA-ACUUAGCGAGUU
                                                              └──────────┘
                                                                   PK2
```

FIG. 3B

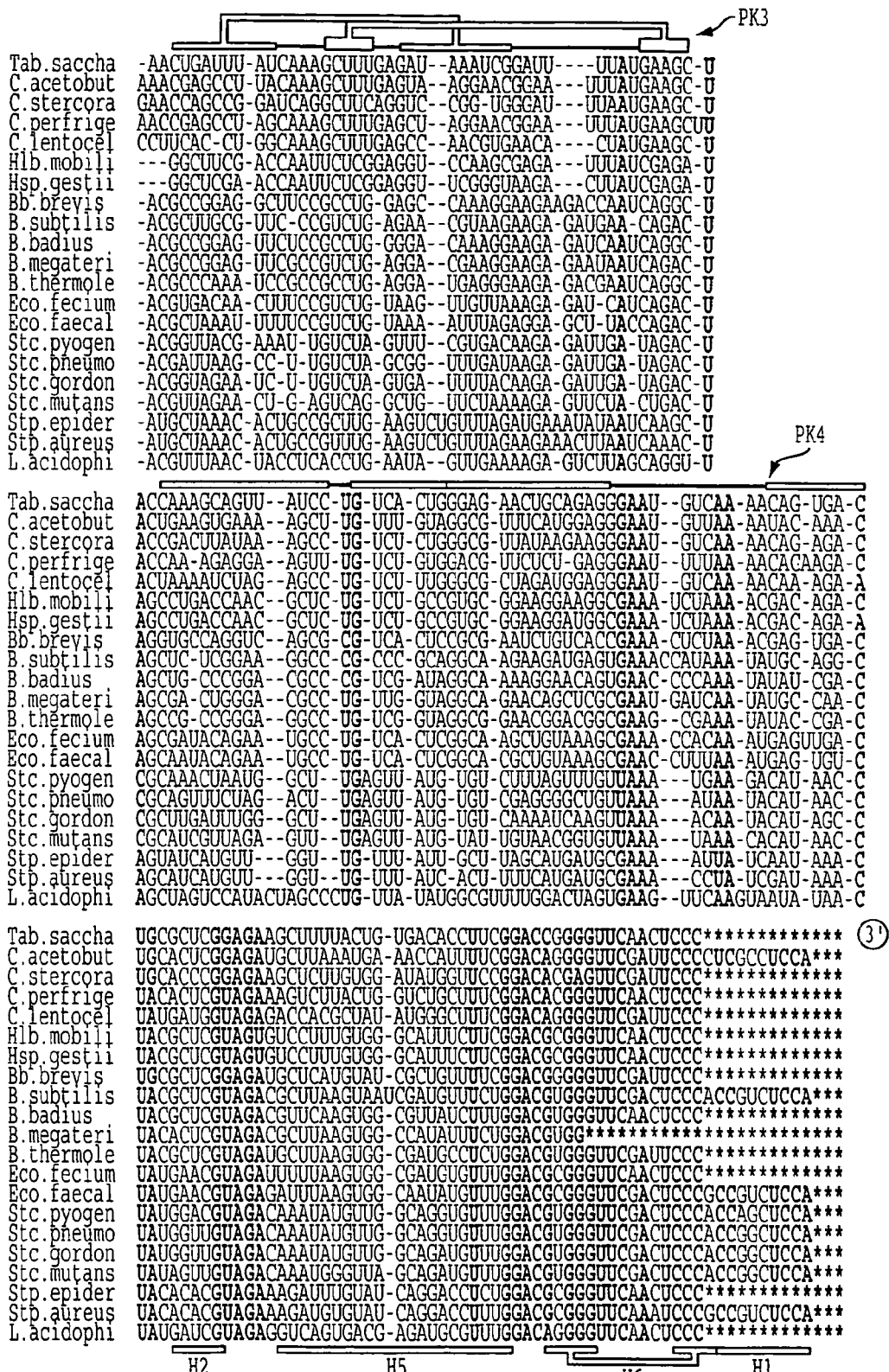
FIG. 3C  +RNA-LIKE DOMAIN H1-H6

```
Aqf.aeolic  CG-GGCUACUCGGU--CGCACGGG-GCUGAGUAGCUGACACCUAACCCGUGCU  ⎫
Tt.maritim  A--CCGAUUCAG--UUCGCCUUCCGGCCUGAAUCGGGAAAACUCAGGAAGGCU  ⎪
Tt.neapoli  A--CCGAUCUGGGCUCCGCCUUCCGGCCCGGAUCGGGAAGGUUCAGGAAGGCU  ⎪
T.thermoph  A--GCCCGGGGC--CACGCCCUCU--AACCCCGGGCGAAGCUUGAAGGGGGCU  ⎪
D.radiodur  A--GCCC-AGGC--GAUUCUCCAU--AGCCGACGGCGAAACU-UUAUGGAGCU  ⎪
D.proteoly  A--GCUU-AGGU--GAGGUUCCAU--AGCCAAAAGUGAAACC-AAAUGGAAAU  ⎬ PK3
Tmc.roseum  GCCCCUGGCCCA--AGCGCCGGUG---CGGGCCAGGUCAAGCGUGAUCCGGCU  ⎪
Ctb.proteo  GC-UCUUAAGCAG--UGGCACCAG--CUGUUUAAGGGUGAAAAGAGUGGUGCU  ⎪
Her.aurant  CGCUCCCCUAGUU--AUGUCUGUG--GGCUAGGGG--CUAAGAUUAACAGGCU  ⎪
Tdb.commun  UU-GGGAGGCUUAA-UCGGUGGGG-UUAAGCCUCCCGAGAUUACAUCCCACCU  ⎪
Ver.spinos  G--GCCAAAAGAGC-GGGCGACCG-GC-CCCAAGGCGAGAUCUACAGGCCGCU  ⎪
Dcg.thermo  GCCCCUUCCG-----ACUCCCCUA-----AGGAAGGGAAAGA-UGUAGGGGAU  ⎭

Aqf.aeolic  A--CCCUC-GGGGAGCUUGCCCGUGGGCGACCC-GAGGG--GAAAUCC-UGAACACGGGC  ⎫
Tt.maritim  G-UGGGAGAGGACACCCUGCCCGUGGGAGGUCC-CUCCC--GAGAGCG-AAAACACGGGC  ⎪
Tt.neapoli  G-UGGGAAGCGACACCCUGCCCGUGGGGGGUC-CUUCCC--GAGACAC-GAAACACGGGC  ⎪
T.thermoph  C-GCUCCUGGCC--GCCCGUCCGCGGGCCAAGCCAGGAG--GACACGC-GAAACGCGGAC  ⎪
D.radiodur  A-CGGCCUGCGAGAACCUGCCCACUGGUGAGCGCCGGCCC-GACAAUC-AAACAGUGGGA  ⎪
D.proteoly  A-AGGCGGACGGCAGCCUGUUUGCUGGCAGCCCAGGCCC--GACAAUU-UAAGAGCAGAC  ⎬ PK4
Tmc.roseum  C-GGCUGACCGGGAUCCUGUCGGUGGGAGCCUGG-CAGC--GACAGUA--GAACACCGAC  ⎪
Ctb.proteo  G--GGCAGUGCGGUU-GGGCU-UCCUGGGCUGCACUGUC--GAGACUU-CACAGGAGGGC  ⎪
Her.aurant  G-GUCGUGGC-CCGCUUUGUCUAUCGGGUGGUGCACCGAU-AAGAUUU-AAUCAAUAGAC  ⎪
Tdb.commun  G--GUAGGGUUGCUUGGUGCCUGUGACAAGCA-CCCUAC-GAGAUUU--UCCCACAGGC  ⎪
Ver.spinos  G--GAUGGACGGCAUCCUGGCAGUAGGAGGCUGGACAUC--GAGAUCA-AAUNAUUGCC  ⎪
Dcg.thermo  AGGUGCUUACAGAAUCCUGCGGGAGGGAGUCUGUAAGUGCCGAAAAGUUAAAACUCCCGC ⎭

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGGACGGGGGUUCGAAUCCCCCGCCUCCACCA
Tt.neapoli  UGCGCU-CGGAGAAGCCCAGGGG---CCUCCAUCUUCGGACGGGGGUUCGAUUCCCGCCGCCUCCA***
T.thermoph  UACGCG-CGUAGAGGCcacgccc---cggcgaccuucggacgggggUUCGAUUCCCCCACCUCCACCA
D.radiodur  UACACA-CGUAGACGCA-CGCUG--GACGGACCUUUGGACGGCGGUUCGACUCCGCCCACCUCCACCA
D.proteoly  UACGCA-CGUAGAUGCA-CGCUG---GAUGGACCUUUGGACGGCGGUUCGAUUCCCGCCGCCU-CACCA
Tmc.roseum  UAAGCC-UGUAGCAUAUCCUCGG---CUGAACGCUCUGGACGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGGG*****************
Dcg.thermo  UAAGCU-UGUAGAGGCUUUUGAU---UCUUGCUCUCUGGACGCGGGUUCGAUUCCCGCCGCCUCCACCA (3')
            ══       ═════════       ══════════   ══╗   ══
            H2         H5                  H6     H1
            +RNA-LIKE DOMAIN H1-H6
```

FIG. 4B

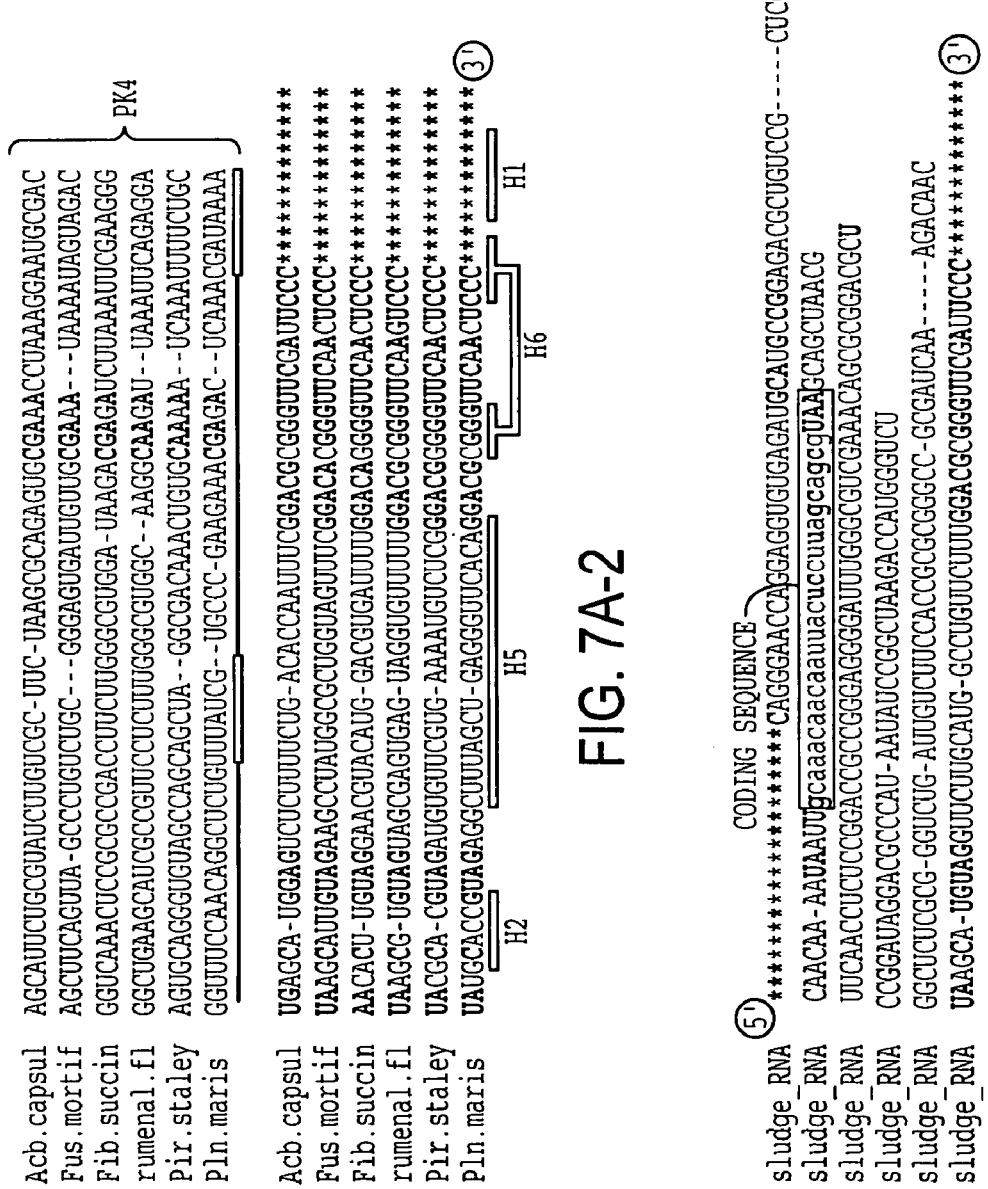

```
Clm.tracho  5'  GGGGGUGUAAAGGUUUCGACUUAG-AAAUGAAGCGUUAAUUGCAUG CGGAGGGCUGGCUUCCUAAAAAGCCGAC AAAACA
Clm.mousep      GGGGGUGUAAAGGUUUCGACUUAG-AAAUGAAGCGUUAAUUGCAUG CGGAGGGCUGGCUUGCCUAAAAAGCCGAC AAAACA
Clm.pneumo      GGGGGUGUAUAGGUUUCGACUUGA-AAAUGAAGUGUUAAUUGCAUG CGGAGGGCUGGCUUGCCUAAAAAGCCAAC AAAACA
                    H1                H5                  H2                              PK4

Clm.tracho      AUAAAU ccgaaccuaaggcugaaugcgaaauuaucagcuucgcugauc ugaagaguagcugcuUAA UUAGCAA-AGUUGUUACC----UAAAUACG-GGUGAC
Clm.mousep      AUAAAU ccgaaccuaaggcugaaugcgaaauuaucagcuucgcugauc ugaagaguagcugcuUAA UUAGCAA-AGUUGUUACC----UAAGUACU-GGUAAC
Clm.pneumo      AUAAAU ccgaaccuaaggcugaaugcgaaauuauuagcuugauuugacu uguugaggaagagcuagcugcuUAA UUAGCAAAAGUUGUUACCAAAAGUUAGGGUGAC
                                                                      ↑ CODING SEQUENCE                         H4

Clm.tracho      CCGGUGUUCGCGAGUCCACCAGAGGUUUCGAAAACACCGUCAUGUAUCUGGUU
Clm.mousep      CCGGUGUUCGCGAGUCCACCAGAGGUUUUCGAAACGCCCUCAUUUAUCUGGUU
Clm.pneumo      CCGGUAUCUGCGAGUCCACCAGAGGCUUGCAAAAUACGUCAUUUAUCUGGUU
                                                                        } PK2

Clm.tracho      AGAACUUAGGUCCUUUAAAUUCUCGAGGAAAUCUAGAGUUGCAAAUUUAAUGAGAGU
Clm.mousep      AGAAUAGGGCCUUUUAACUCUAAUUCUCGAGGAACUAAUUGAAUUUAAUGAGAGU
Clm.pneumo      GGAACUUACUUUCUAAUUCUCUAAUUCUCAAGGAGUCGUUCGAGAUUU-UUGAGAGU
                                                                        } PK3

Clm.tracho      CGUUA-GUCUCUAUAGGGGUUUCUAGCUGAGGAGACAUAACGUAUAGUA-CCUAGGAAC
Clm.mousep      CGUUG-GUCUCUAUAGAGGUUUCUAGCUGAGGAGACAUAUAACGUAUAUAUAUAAUUCUAGAAAC
Clm.pneumo      CAUUGG-CUGCUAUAGAGGCUUCUAGCUGAGGAGACAUAAGGAGUUACAAUUGUAAACAAUUCUAGAGA
                                                                                             } PK4

Clm.tracho      UAAGCAUGUAGAGGUUUAGCGGGGAGUUUACUAAGGACGAGAGUUCGACUCUCUCCACCACCUCCAcca 3'
Clm.mousep      UAAGCAUGUAGAGGUUAGCGGGGAGUUACUAAGGACGAGAGUUCGACUCUCUCCACCACCUCCAcca
Clm.pneumo      UAAGCAUGUAGAGGUUAGCGGGGAGUUUGUCAAGGAGUCGAGAGUUCGAGUCUCUCCACCACCUCCAcca
                       H2              H5                              H6                   H1
```

FIG. 7D

```
                    H1                    H5              H2              PK1
         5'    ┌──────┐        ┌────────────┐        ┌──────┐       ┌──────────┐
Trp.pallid  GGGGAUGACU-AGGUUUCGACUAGGGAUGUG-GGGUGUUGCGCUGCAGGUGGAGUGUCGAUCUCCUGAU--UCGGCGCCUUU
Bor.burgdo  GGGGAUGUUU-UGGAUUUGACUGAAAAUGUUAAUAUUGUAAGUUGCAGGCAGAG--GGAAUCUCUUAAAACUUCUA----AA
Bor.qarini  GGGGCUGAUUCUGGAUUCGACUGAAAAUGCGAAUAUUGUAAGUUGCAGGCAGAG--GGAAUCUCUUAAAACUUCUA----AA
Bor.afzeli  GGGGCUGAUUCUGGAUUCGACUGAAAAUGCUAAUAUUGUAAGUUGCAAGCAGAG--GGAAUCUCUUAAAACUUCUA----AA
Bor.crocid  GGGGCUGAUUCUGGAUUCGACUAAGAACUUUAGUAGCAUAAAUGGCAAGCAGAG--UGAAUCUCUUAAAACUUCUU----UA
Bor.hermsi  GGGGCUGAUUCUGGAUUCGACUAAAAACUUUAGUAGCAUAAAUUGCAAGCAGAG--GGAAUCUCUUAAAACUUCUU----UA
                         CODING SEQUENCE                                       ┌──┐ H4
Trp.pallid  AUAACUgccaauucugacaguuuc---------gacuacgcgcucgccgcgUAA----UCG
Bor.burgdo  AUAAAUgcaaaaaauaauaacuuuacaagcucaaaucuuguaauggcugcuUAAGUUAGCAG
Bor.qarini  AUAAAUgcaaaaaauaauaacuuuacaagcucaaaccuuguaauggcugcuUAAGUUAGCAG
Bor.afzeli  AUAAAUgcaaaaaauaauaacuuuacaaguucaaaccuuguaauggcugcuUAAGUUAGCAG
Bor.crocid  AUAAAUgcaaaaaauaauaacuuuacaaguucagaucuuguaauggcugcuUAAUUUAGCAG
Bor.hermsi  AUAAAUgcaagaaauaauaacuuuacaaguucaaaucuuguaauggcugcuUAAAUUAGCAG Trp.pallid  CGGGCCU-GUGUUUGCGCUGCUCUG-AGCGAACAUAUCGGCCCGAC-GCCAAACGGAGCU ⎫
Bor.burgdo  -AGGGUUUUGUUGAAUUUGGCUUUGAGGUUCA-CUUAUACUCUUUU-CGACAUCAAAGCU ⎪
Bor.qarini  -GGAGUUUCGUUGAAUUUGGCUUUGAGGUUCA-CUUAUACUCUUUU-CGAUAUCGAAGCU ⎬ PK2
Bor.afzeli  -AGAGUUUUGUUGAAUUUGGCUUUGAGAUUCA-CUUAUACUCUUUU-AGACAUCGAAGCU ⎪
Bor.crocid  -AGAGUUUUGUUGGAUUUUGCUUUGAGGUUCAACUUAUACUCUUUA-AGACAUCAAAGUA ⎪
Bor.hermsi  -AGAGUUCUGCUGGAUUUUGCUUUGAGGUUCAGCUUAUACUCUUUUAAGACAUCAAAGCU ⎭

Trp.pallid  UGCUCUUACGUUG-UGCACGGCGGACGUAGGGGACUUUUGUCUGUGCU ⎫
Bor.burgdo  UGCUUAAAAAUGUUUUCAAGUU-GAUUUUUAGGGACUUUUAUACUUGAG ⎪
Bor.qarini  UGCUUAAAAAUGUUUUCAAGUU-AAUUUUUAGGGACUUUUGUACUUGAG ⎬ PK3
Bor.afzeli  UGCUUAAAAAUGUUUUCAAGUU-GAUUUUUAGGGACUUUUAUACUUGAG ⎪
Bor.crocid  UGCCUAAAAAUGU-UUCAAGUU-GAUUUUUAGGGACCUUUAAACUUGAG ⎪
Bor.hermsi  UGCUUAAAAAUAU-UUCAAGUU-GAUUUUUAGGGACUUUUAAAUUUGAG ⎭

Trp.pallid  AAGACUCUGGCGCG-UGCGGUGCAGGCCUAGCAGAGUCCGACAAACGCAGUACGCACCGC ⎫
Bor.burgdo  AGCAAUUUGGUGGUUUGCUAGUAUUUCCAAACCAUAUUGCU---U-AAUAAAAUACUAGA ⎪
Bor.qarini  AGCAAUUUGGCGGUUUGCUAGUAUUUCCAAACCAUAUUGCU---UAAGUAAAAUGCUAGA ⎬ PK4
Bor.afzeli  AGCAAUUUGGCGGUUUGCUAGUAUUUCCAAACCAUAUUGCU---U-AGUAAAAUACUAGA ⎪
Bor.crocid  AGUAAUUGGGUGGUUUGCUUGUUUU-CCAAGCCUUAUUGCU---UUUUCUAAAAAUUAGC ⎪
Bor.hermsi  AGUAAUUGGCGGUUUGCUAGUUUUUCCAAACCUUAUUACU---UAAAGAAAACACUAGC ⎭

Trp.pallid  UAAACCUGUAGGCGCGCAGCACUCG-CUCUUUAGGACGGGGGUUCGAUUCCCCCCAUCUCCACca
Bor.burgdo  UAAGCUUGUAGAAGCUUAUAGUAUU-AUUUUUAGGACGCGGGUUCAAUUCCCGCCAUCUCCAcca
Bor.qarini  UAAGCUUGUAGAAGCUUAUAAUAUU-GUUUUUAGGACGCGGGUUCAauuccgccaucuccacca
Bor.afzeli  UAAGCUUGUAGAAGCUUAUAGUAUU-GUUUUUAGGACGCGGGUUCAauuccgccaucuccacca
Bor.crocid  UAAGCUUGUAGAUAUUUAUGAUAUU-AUUUUUGGACGCGGGUUCAauuccgccaucuccacca
Bor.hermsi  UAAGCUUGUAGAUAUUUAUGAUAUU-AUUUUUAGGACGCGGGUUCAauuccgccaucuccacca 3'
                  ────────  ──────────      ┌──┐      ┌──────┐
                      H2          H5          H6        H1
```

FIG. 8B

```
Alc.faecal  GCAGUGUUAU-UUACAAAGAAU---C-GAAUCGGUCUGCGCCACGAAGUCCGGUUCUAAAA-CUUAGUGGAU
Alc.eutrop  GCGAGGUCAU-UUACGUCAGAU---A-AGCUCCGGAAGGGUCACGAAGCCGGGGACGAAAA-CCUAGUGACU
Ral.picket  GCGAGGUCAU-UUACGUCAGAU---A-AGCUUUAGGUGAGUCACGGGCCUAGAGACGAAAA-CUUAGUGAAU
Nis.gonorr  GCAACGUCAUCUUACAUUGACU---G-GUUUCCAGCCGGGUUACUUGGCAGGAAAUAAGACUUAAGGUAACU
Nis.meninS  GCAACGUCAUCUUACAUUGACU---G-GUUUCCUGCCGGGUUAUUUGGCAGGAAAUGAGAUUUAAGGUAACU
Chb.violac  GUAGUGUCACUCUACAUCUGCU---A-GUGCUGUUCCGGGUUACUUGGUUCAGUGCGAAAUAAUAGGUAACU
Nms.cryoto  GCAGAGUCAU-UAG-CAAGGAU---C-GCGUUCUGUAGGGUCACUUUACAGAACGUUAAACAAUAGGUGACU
Mtb.glycog  GCAGCGUCAU-UAAGAGAGGAU---C-GUGCGAUAUUGGGUUACUUAAUAUCGUAUUAAAUCCAAGGUAACU
Ps.testost  GCAAGGGAAU-UUUCAUUAGCU---G-GCUGGAUACCGGGCUUCUUGGUAUUUGGCGAGAUUUUAGGAAGCU
Vx.paradox  GCAAGGAUAA-CUACAUGGGCU---G-GCUCCGAUCCGGGUACCUUGGGUCGGGGCGAGAAAAUAGGGUACU
Hph.paller  GCAAGGUAAU-UUACAUCGGCU---G-GUUCUGCGUCGGGCACCUUGGCGCAGGAUGAGAUUCAAGGAUGCU
Brd.pertus  GCAGCGACAU-UCACAAGGAAU---C-GGCCACCGCUGGGUCACA-CGGCGUUGGUUUAAA-UUACGUGAAU
                      PK2
Alc.faecal  CGCCAAGG-AAAGGCCUGUCA-AUUGGCAUAGUCCAAGGUUAAAACUUAAAAUUAAU-UGAC
Alc.eutrop  CGCCGUCG-UAGAGCGUGUUC-GUCCGCGAUG-CGCCGGUUAAAU---CAAA-UGACAGAAC
Ral.picket  CGCCGUCG-UAGAGCGUGUUC-GUCCGCGAUG-CGGCGGUUAAAU---CAAA-UGACAGAAC
Nis.gonorr  GGUUUCCA-AAAGGCCUGUUG-GUCGGCAUGA-UGGAAAUAAGAUUUUCAAAUAGACACAAC
Nis.meninS  GGUUUCCA-AAAGGCCUGUUG-GUCGGCAUGA-UGGAAAUAAGAUUUUCAAAUAGACACAAC
Chb.violac  CGCCAAAGUCCA-GCCUGUCC-GUCGGCGUGG-CAGAGGUUAAAUC--CAAA-UGACACGAC
Nms.cryoto  CGCCUGCC-AUCAGCCCGCCA-GCUGGCGGUU-GUCAGGUUAAAU---UAAA-GAGCAUGGC
Mtb.glycog  CGCCUGCU-GUUUGCUUGCUC-GUUGGUGAGC-AUCAGGUUAAAU---CAAA-CAACACAGC
Ps.testost  GGCUACCCAAGCAGCGUGUGC-CUGCGGGGUUUGGGUGGCGAGAUU--UAAA-ACAGAGCAC
Vx.paradox  GGCGUCCGGUUUAGCGUGUGA-CUGCGCGACUCCGGAAGCGAGACU--CAAA-ACAGAUCAC
Hph.paller  GGCUUCCCGUUUAGCGUGCCA-CUGCGCGACUCGGGCGGCGAGACC--CAAA-UCAGACGGC
Brd.pertus  CGCCCUGG-UCCGGCCCGUCG-AUCGGCUAAGUCCAGGGUUAAAUC--CAAAUAGAU-CGAC
                                                                              PK4

Alc.faecal  UACACAUGUAGAACUGUCUGUGGACGGCUUGCGGACGGGGGUUCGAUUCCC**********
Alc.eutrop  UAAGUAUGUAGAACUCUCUGUGGAGGGCUUACGGACGCGGGUUCGAUUCCCGCCGGCUCCACCA
Ral.picket  UAAGUAUGUAGAACUCUCUGUGGAGGGCUUGCGGACGCGGGUUCGAUUCCC***********
Nis.gonorr  UAAGUAUGUAGAACGCUUUGUAGAGGACUUUCGGACGGGGGUUCGAUUCCCCCCGCCUCCACCA
Nis.meninS  UAAGUAUGUAGAACGCUUUGUAGAGGACUUUCGGACGGGGGUUCGAUUCCCCCCGCCUCCACCA
Chb.violac  UAAGUAUGUAGAACUCACUGUAGAGGACUUUCGGACGCGGGUUCAACUCCC***********
Nms.cryoto  UAAGUAUGUAGAACUGUCUGUAGAGGACUUGCGGACGCGGGUUCAACUCCC***********
Mtb.glycog  UAAGUAUGUAGAACUGUCUGUGGAGGGCUUGCGGACGGGGGUUCGAUUCCC***********
Ps.testost  UAAACAUGUAGAUCUGUCCGGCGAAGGCUUACGGACGCGGGUCAAUUCCCGCCGGCUCCA***
Vx.paradox  UAAACAUGUAGAACUGCGCGAUGAAGGCUUGCGGACGGGGGUUCAACUCCC***********
Hph.paller  UACACAUGUAGAACUGCUCGAAAAGGCUUGCGGACGGGGGUUCAACUCCC***********
Brd.pertus  UAAGCAUGUAGAACUGGUUGCGGAGGGCUUGCGGACGGGGGUUCAAUUCCCCCCGGCUCCACCA (3')
               H2      H5              H6         H1
```

FIG. 9B

```
                          H1               H5              H2
             ⑤'          ━━              ━━━━━━━━━━      ━━
Leg.pneumo   *******************CGUGGGUUGCAAAACCGGAAGUGCAUGC
Chr.vinosu   *******************CGUGGGUCGCGAAACCUAAGGUGCAUGC
Dcb.nodosu   ****************************CUCGAGGUGCAUGU
Ps.aerugin   GGGGCCGAUU-AGGAUUCGACGCCGGUAACAAAACUUGAGGGGCAUGC
Ps.fluores   *******************CGCCGGUUGCGAACCUUUAGGUGCAUGC
Mar.hydroc   *******************CGCCGGUGACGAACCCUUGGGUGCAUGC
Shw.putref   GGGGGCGAUUCUGGAUUCGACAGGAUUCACGAAACCCUGGGAGCAUGC
Psm.halopl   *******************CGGAAUUCAAGAAGCCCGAGGUGCAUGU
Ae.salmoni   *******************CAAGAUUCACGAAACCCAAGGUGCAUGC
S.typhimur   GGGGCUGAUUCUGGAUUCGACGGGAUUUGCGAAACCCAAGGUGCAUGC
E.coli       GGGGCUGAUUCUGGAUUCGACGGGAUUUGCGAAACCCAAGGUGCAUGC
Yer.pestis   GGGGCUGAUUCUGGAUUCGACGGGAUUCGCGAAACCCAAGGUGCAUGC
V.cholerae   GGGGCUGAUUCAGGAUUCGACGGGAAUUUUGCAGUCUGAGGUGCAUGC
H.influenz   GGGGCUGAUUCUGGAUUCGACGGGAUUAGCGAAGCCCAAGGUGCACGU
H.actinomy   GGGGCUGAUUCUGGAUUCGACGGGAUUAGCGAAGCCCGAAGUGCACGU
                                          PK1
                         ┌──────────────────────────┐
Leg.pneumo   CGAG-AAGGAGAUC-UCUCGUAAAUA-AGA-CUCAAUUA-AAU
Chr.vinosu   CGAG-GUGCGGUUGACCUCGUAAAAC--CCUCCGCAAA--CUU
Dcb.nodosu   CGAG-AAUGAGAGAAUCUCGUUAAAU--ACUUUCAAAA--CUU
Ps.aerugin   CGAGCUGGUAGCAGAACUCGUAAAUUCGCUGCUGCAAA--CUU
Ps.fluores   CGAGUUGGUAACAGAACUCGUAAAUCCACUGUUGCAACUUUCU
Mar.hydroc   CGAGAUGGCAGCGAAUCUCGUAAAUCCAAAGCUGCAAC--GUA
Shw.putref   CGAG-GGGCGGUUGGCCUCGUAAA----AAGCCGCAAA--GUU
Psm.halopl   CGAG-GUGCGGUUUGCCUCGUAAAA---AAGCCGCAAUU-UAA
Ae.salmoni   CGAG-GUGCGGUAGGCCUCGUUAAC---AAACCGCAAA--AAA
S.typhimur   CGAG-GGGCGGUUGGCCUCGUAAA----AAGCCGCAAA--AAA
E.coli       CGAG-GGGCGGUUGGCCUCGUAAA----AAGCCGCAAA---AA
Yer.pestis   CGAG-GUGCGGUG-GCCUCGUAAA----AAACCGCAAA-AAAA
V.cholerae   CGAG-GUGCGGUAGGCCUCGUUAAC---AAACCGCAAA--AAA
H.influenz   CGAG-GUGCGGUAGGCCUCGUAAAU---AAACCGCAAA--AAA     CODING SEQUENCE
H.actinomy   CGAG-GUGCGGUAGGCCUCGUAAAU---AAACCGCAAA--AAA              ↓
             ━━━━━━━━━━━━━━━━━━━━━━━━━━━━━━━━━━━━━
                                                        ┌────────────────────────────────────┐
Leg.pneumo   A-UAAAU│gcaaacgaugaaaacuuugcugguggggaagcuaucgcugccUAA│-----UAAGCACUUU
Chr.vinosu   A-UAGUU│gccaacgacgacaacuac-----------gcucucgcugcuUAA│-----UCCCAGCGGG
Dcb.nodosu   A-UAGUU│gcaaacgacgacaacuac-----------gcuuuagcggcuUAA│-----UUCCCGCUUU
Ps.aerugin   A-UAGUU│gccaacgacgacaacuac-----------gcucuagcugcuUAA│------UGCGGCUAG
Ps.fluores   A-UAGUU│gccaaugacgaaaccuac----ggggaauacgcucucgcugcgUAA│-------GCAGCCUU
Mar.hydroc   A-UAGUC│gcaaacgacgaaaacuac-----------gcacuggcggcgUAA│---GCCGUU-CCAGU
Shw.putref   A-UAGUU│gcaaacgacgauaacuac-----------gcucuagccgcuUAA│-----UGCCGCUAG
Psm.halopl   AGUAAUC│gcaaacgacgauaacuac-----------ucucuagcagcuUAG│-----GCUGGCUAG
Ae.salmoni   A-UAGUC│gcaaacgacgaaaacuac-----------gcacuagcagcuUAA│UAACCUGCAUAGAGC
S.typhimur   A-UAGUC│gcaaacgacgaaaccuac-----------gcuuuagcagcuUAA│UAACCUGCUUAGAGC
E.coli       A-UAGUC│gcaaacgacgaaaacuac-----------gcuuuagcagcuUAA│UAACCUGCUUAGAGC
Yer.pestis   A-UAGUU│gcaaacgacgaaaacuac-----------gcacuagcagcuUAA│UAACCUGCUUAGAGC
V.cholerae   A-UAGUC│gcaaacgacgaaaacuac-----------gcacuagcagcuUAA│UACCCUGCUCAGAGC
H.influenz   A-UACUC│gcaaacgacgaacaauac-----------gcuuuagcagcuUAA│UAACCUGCAUUUAGC
H.actinomy   A-UAGUC│gcaaacgacgaacaauac-----------gcuuuagcagcuUAA│UAACCUGCCUUUAGC
                                                                      ━━━━━━  ━━━━━━
                                                                           H4
```

FIG. 10A

```
Leg.pneumo  AGUUAAACCAUCACUGUGUACUGGCCAAUAAACCCAGUAUC
Chr.vinosu
Dcb.nodosu
Ps.aerugin
Ps.fluores  AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy Leg.pneumo  CCGUUCG-ACCGAGCCC--GCUUAUC-GGUAUCGAA-------UCAACGGUCAU-AAGAGAU-AAGCU
Chr.vinosu  CCUCUGA-CCGUCACUU--GCCUGUGGGCGGCGGAUU------CCAGGGGUAAC-CUCACAC-AGGAU
Dcb.nodosu  CGCUUAC-CUAGAUUU---GUCUGUGGGUUUACC--------GUAAGCGACAU--UAACAC-AGAAU
Ps.aerugin  CAGUCGC-UAGGGGAU---GCCUGUAAACCCGAAA--------CGACUGUCAG-AUAGAAC-AGGAU
Ps.fluores  CAAUCAU-CAGGGGAU---GUCUGUAAACCCAAAG--------UGAUUGUCAU-AUAGAAC-AGAAU
Mar.hydroc  CGUCCUG-GCUGAGGC---GCCUAUAACUCAGUAGCAACAUCCCAGGACGUCAU-CGCUUAU-AGGCU
Shw.putref  CCAUCUA-CCACACGCUUUGCACAUGGGCAGUGGAUU------UGAUGGUCAU-CUCACAUCGUGCU
Psm.halopl  CGCUCCU-UCCAUGUAU--UCUUGUG-GACUGGAUUUU-----GGAGUGUCACCCUAACAC-CUGAU
Ae.salmoni  CCUUCUA-CCCUAGCUU--GCCUGUGUCCUAGGGAAUC-----GGAAGGUCAU-CCUUCAC-AGGAU
S.typhimur  CCUCUCU-CCCUAGCCUCCGCUCUUAGGACGGGGAUCA-----AGAGAGGUCAAACCCAAAA-GAGAU
E.coli      CCUCUCU-CCCUAGCCUCCGCUCUUAGGACGGGGAUCA-----AGAGAGGUCAAACCCAAAA-GAGAU
Yer.pestis  CCUCUCU-CCCUAGCCUCCGCUCUUAGGACGGGGAUCA-----AGAGAGGUCAAACCUAAAA-GAGCU
V.cholerae  CCUUCCU-CCCUAGCUUCCGCUUGUAAGACGGGGAAAUC----AGGAAGGUCAAACCAAAUC-AAGCU
H.influenz  CUUCGCG-CUCCAGCUUCCGCUCGUAAGACGGGGAUAA-----CGCGGAGUCAAACCAAAAC-GAGAU
H.actinomy  CUUCGCU-CCCCAGCUUCCGCUCGUAAGACGGGGAUAA-----AGCGGAGUCAAACCAAAAC-GAGAU
                        PK2
```

FIG. 10B

```
                           PK3
            ┌─────────────────────────────────────────────────────────┐
            ┌──┐                                                   ┌──┐
Leg.pneumo  -AGCG-UCCU-AAUCU--AUCCC-GGGUU-AUGG-CGCGAAA-CU-CA--GGGAAU
Chr.vinosu  -CGUG-GUGA-CGGGA--GUCCG-GACCU-GAUC-CACUAAAACC-UA-ACGGAAU
Dcb.nodosu  -CGCU-GGUU-AACG--CGUCCGC-UGUU-AAUC-GGUUAAA-UU-AA-GCGGAAU
Ps.aerugin  -CGCC-GCCA-AGUU--CGCUGUA-GACG-UAAC-GGCUAAAACU-CA-UACAGCU
Ps.fluores  -CGCC-GUGC-AGUA--CGUUGUG-GACG-AAGC-GGCUAAAACU-UA-CACAACU
Mar.hydroc  GCUCC-GUUC-ACCAG-AGCUCA-CUGGU-GUUC-GGCUAAG-AU-UA-AAGAGCU
Shw.putref  -AGCGAGGGA-ACCC--UGUCUGG-GGGU-GAAC-CGCGAAACAG-UA-CCGGACU
Psm.halopl  -CGCGACGGA-AACCC-UGGCCG-GGGUU-GAAG-CGUUAAAACU-AA-GCGGCCU
Ae.salmoni  -CGUG-UGGA-AGUCC-UGCUCG-GGGCG-GAAG-CAUUAAAACC-AA-UCGAGCU
S.typhimur  -CGCG-CGGA-UGCCC-UGCCUG-GGGUU-GAAG-CGUUAAAACG-AA-UCAGGCU
E.coli      -CGCG-UGGA-AGCCC-UGCCUG-GGGUU-GAAG-CGUUAAAACUUAA-UCAGGCU
Yer.pestis  -CGUG-UGGA-AACCU-UGCCUG-GGGUG-GAAG-CAUUAAAACU-AA-UCAGGAU
V.cholerae  -GGCG-UGGA-UUCCCCCACCUGA-GGGAUGAAG-CGCGAGAUCU-AAUUCAGGUU
H.influenz  -CGUG-UGGA-AGCCACCGUUUGA-GGAUCGAAG-CACUAAAUUG-AA-UCAAACU
H.actinomy  -CGUG-UGGA-AGCCACCGUUUGA-GGAUCGAAG-CAUUAAAUUA-AA-UCAAAGU ┌──────────────────────────────────────────────────────────┐
            ┌──┐                                                    ┌──┐
Leg.pneumo  CGCUGUGUAU-CAUCCUGCCC-GUCGGAGGAGCCACAGUUAAAUUCAAAAGACAAGGC--⎫
Chr.vinosu  CGCCGACUGAUCGCCCUGCCC-UUCGGGCGGCAGAAGGCUAAAAACAAUAGAGUGGGC--⎪
Dcb.nodosu  CGCUUGUAAA-AUGCCUGAGC-GUUGGCUGUUUAUGAGUUAAACCUAAUUAACUGCUC--⎪
Ps.aerugin  CGCUCCAAGC--ACCCUGCCA-CUCGGGCGGCGCGGAGUUA-CUCAGUAGAGCUGGC--⎪
Ps.fluores  CGCCCAAAGC--ACCCUGCCC-GUCGGGUCGCUGAGGGUUAA-CUUAAUAGACACGGC--⎪
Mar.hydroc  CGCCUCUUGC--ACCCUGACC-UUCGGGUCGCUUGAGGUUAA-AUCAAUAGAA-GGACAC⎪
Shw.putref  CACCGUGUGG-GAUCCUGUCU-UUCGGAGUUCAAACGGUUAA-ACAAUA-GAA-AGAC--⎬ PK4
Psm.halopl  CGCCUUUAUC-UACCGUGUUU-GUCCGGGAUUUAAAGGUUAA-UUAAAU-GACAAUAC--⎪
Ae.salmoni  AGUCAAUUCG-UGGCGUGUCU-CUCCGCAGCGGGUUGGCGAA-UGUAAA-GAG-UGAC--⎪
S.typhimur  AGUCUGGUAG-UGGCGUGUCC-GUCCGCAGGUGCCAGGCGAA-UGUAAA-GAC-UGAC--⎪
E.coli      AGUUUGUUAG-UGGCGUGUCC-GUCCGCAGCUGGCAAGCGAA-UGUAAA-GAC-UGAC--⎪
Yer.pestis  AGUUUGUCAG-UAGCGUGUCC-AUCCGCAGCUGGCCGGCGAA-UGUAAU-GAUUGGAC--⎪
V.cholerae  AGCCAUUCGU-UAGCGUGUCG-GUUCGCAGGCG-GUGGGUGAA-AUUAAA-GAU-CGAC--⎪
H.influenz  AGCUUAAGUU-UAGCGUGUCU-GUCCGCA-UGCUUAAGUGAA-AUUAAA-GACGAGAC--⎪
H.actinomy  AGCUUAAUUG-UCGCGUGUCC-GUCAGCA-GGAUUAAGUGAA-UUUAAA-GACCGGAC--⎭

Leg.pneumo  UAUGCAUGUAGAGCUAAAGGCAGAGGACUUGCGGACGCGG*******************
Chr.vinosu  UAAGCAUGUAGGACCGAGGGCAGAGGGCUUGCGGACGCGG*******************
Dcb.nodosu  UAAACAUGUAGUACCAAAAGUUAAGGAUUCGCGGACGGGGGGUUCAAAUCCCCCCGCCUCCACCA
Ps.aerugin  UAAGCAUGUAGAACCGAUAGCGGAGAGCUGGCGGACGGGGGUUCAAAUCCCCCCGGCUCCACCA
Ps.fluores  UACGCAUGUAGUACCGACAGCAGAGUACUGGCGGACGGGG*******************
Mar.hydroc  UAAGCAUGUAGACCUCAAGGCCUAGUGCUGGCGGACGCGG*******************
Shw.putref  UAAGCAUGUAGCGCCUUGGAUGUAGGUUUUCUGGACGCGGGUUCAAGUCCCGCCGCCUCCACCA
Psm.halopl  UAAACAUGUAGUACCGACGGUCGAGGCUUUUCGGACGGGG*******************
Ae.salmoni  UAAGCAUGUAGUACCGAGGAUGUAGUAAUUUUGGACGGGG*******************
S.typhimur  UAAGCAUGUAGUACCGAGGAUGUAGGAAUUUCGGACGCGGGUUCAACUCCCGCCAGCUCCACCA
E.coli      UAAGCAUGUAGUACCGAGGAUGUAGGAAUUUCGGACGCGGGUUCAACUCCCGCCAGCUCCACCA
Yer.pestis  UAAGCAUGUAGUGCCGACGGUGUAGUAAUUUCGGACGGGGGUUCAAAUCCCCCCAGCUCCACCA
V.cholerae  UAAGCAUGUAGUACCAAAGAUGAAUGGUUUUCGGACGGGGGUUCAACUCCCCCCAGCUCCACCA
H.influenz  UAAACGUGUAGUACUGAAGGUAGAGUAAUUUCGGACGGGGGUUCAACUCCCCCCAGCUCCACCA
H.actinomy  UAAACGUGUAGUGCUAACGGCAGAGGAAUUUCGGACGGGGGUUCAACUCCCCCCAGCUCCACCA 3'
              ──────   ─────────       ──────           ──────
                H2        H5              H6               H1
```

FIG. 10C

SEQUENCE LISTING

<160> NUMBER OF SEQ ID NOS: 175

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
ggggctgatt ctggattcga c                                              21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
tggagctggc gggagttgaa c                                              21

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
gggggcggaa aggattcgac g                                              21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4

```
tggaggcggc gggaatcgaa c                                              21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a                                              21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c                                              21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a                                              21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c                                              21

<210> SEQ ID NO 9
<211> LENGTH: 352
<212> TYPE: DNA
<213> ORGANISM: Acidobacterium capsulatum

<400> SEQUENCE: 9
gggggcggaa aggattcgac ggggttgact gcggcaaaga ggcatgccgg ggggtgggca    60
cccgtaatcg ctcgcaaaac aatacttgcc aacaacaatc tggcactcgc agcttaatta   120
aataagttgc cgtcctctga ggcttcgcct gtgggccgag gcaggacgtc atacagcagg   180
ctggttcctt cggctgggtc tgggccgcgg ggatgagatc cacggactag cattctgcgt   240
atcttgtcgc ttctaagcgc agagtgcgaa acctaaagga atgcgactga gcatggagtc   300
tcttttctga caccaatttc ggacgcgggt tcgattcccg ccgcctccac ca           352

<210> SEQ ID NO 10
<211> LENGTH: 353
<212> TYPE: DNA
<213> ORGANISM: Coprothermobacter proteolyticus

<400> SEQUENCE: 10
gggggcggaa aggattcgac ggggagtcgg agccttgagc tgcaggcagg gttggctgcc    60
```

```
acaccttaaa aagggtagca aggcaaaaat aaatgccgaa ccagaatttg cactagctgc    120
ttaatgtaag cagccgctct ccaaactgag gctgcataag tttggaagag cgtcaaccca    180
tgcagcggct cttaagcagt ggcaccagct gtttaagggt gaaaagagtg gtgctgggca    240
gtgcggttgg gcttcctggg ctgcactgtc gagacttcac aggagggcta agcctgtaga    300
cgcgaaaggt ggcggctcgt cggacgcggg ttcgattccc gccgcctcca cca           353
```

<210> SEQ ID NO 11
<211> LENGTH: 399
<212> TYPE: DNA
<213> ORGANISM: Bacteroides thetaiotaomicron

<400> SEQUENCE: 11

```
ggggctgatt ctggattcga cagcgggcag aaatggtagg taagcatgca gtgggtcggt     60
aatttccact taaatctcag ttatcaaaac tttatctggc gaaactaatt acgctcttgc    120
tgcttaatcg aatcacagta gattagctta atccaggcac taggtgccag gacgagacat    180
cactcggaag ctgttgctcc gaagcattcc ggttcagtgg tgcagtaaca tcggggatag    240
tcagaagcgg cctcgcgttt ttgatgaaac tttagaggat aaggcaggaa ttgatggctt    300
tggttctgct cctgcacgaa aatttaggca aagataagca gtagaaagc ttatgatttc    360 ctcgtttgga cgagggttca actcccgcca gctccacca                           399
```

<210> SEQ ID NO 12
<211> LENGTH: 352
<212> TYPE: DNA
<213> ORGANISM: Dictyoglomus thermophilum

<400> SEQUENCE: 12

```
ggggctgatt ctggattcga cagggagtac aaggatcaaa agctgcaagc cgaggtgccg     60
ttacctcgta aaacaacggc aaaaaagaag tgccaacaca aatttagcat tagctgctta    120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aaagttaaaa ctcccgctaa gcttgtagag    300
gcttttgatt cttgctctct ggacgcgggt tcaactcccg ccagctccac ca             352
```

<210> SEQ ID NO 13
<211> LENGTH: 313
<212> TYPE: DNA
<213> ORGANISM: Artificial
<220> FEATURE:
<223> OTHER INFORMATION: sequence isolated from rumenal fluid

<400> SEQUENCE: 13

```
acgcccttgt ctcagacgag ggcactcgtt aaaagtctg aaaagaataa ctgcagaacc      60
tgtagctatg gctgcttaat ttaagggcaa cccttggatc cgcctccatc ccgaaggggt    120
ggcatccgag tcgcaaatcg ggataggatg gatcttggca acgaggagta catccgaaat    180
ttgtcgctgc tggctgaagc atcgccgttc tctttgggc gtggcaaggc aagattaaat    240
tcagaggata agcgtgtagt agcgagtgag taggtgtttt tggacgcggg ttcaagtccc    300
gccatctcca cca                                                       313
```

<210> SEQ ID NO 14
<211> LENGTH: 350
<212> TYPE: DNA

<213> ORGANISM: Artificial
<220> FEATURE:
<223> OTHER INFORMATION: sequence isolated from sludge

<400> SEQUENCE: 14

```
ggggatgtca tggttttgac agggaaccag gaggtgtgag atgcatgccg gagacgctgt        60
ccgctccgtt atcaagcagc aaacaaaact aattgcaaac aacaattact ccttagcagc       120
gtaagcagct aacgttcaac ctctccggac cgccggagg ggatttgggc gtcgaaacag        180
cgcggacgct ccggatagga cgcccataat atccggctaa gaccatgggt ctggctctcg       240
cgggtctgat tgtcttccac cgcgcgggcc gcgatcaaag acaactaagc atgtaggttc       300
ttgcatggcc tgttctttgg acgcgggttc gattcccgcc atctccacca                  350
```

<210> SEQ ID NO 15
<211> LENGTH: 359
<212> TYPE: DNA
<213> ORGANISM: Fibrobacter succinogenes

<400> SEQUENCE: 15

```
ggggctgatt ctggattcga cagggttacc gaagtgttag ttgcaagtcg aggtctcaga        60
cgagggctac tcgttaaaaa gtctgaaaaa aataagtgc tgacgaaaac tacgcactcg        120
ctgcctaatt aacggcaacg ccgggcctca ttccgctccc atcggggtgt acgtccggac       180
gcaatatggg atagggaagt gtcatgcctg ggggcatctc ccgagatttt ctaggctggt       240
caaactccgc gccgaccttc ttgggcgtgg ataagacgag atcttaaatt cgaagggaac       300
acttgtagga acgtacatgg acgtgatttt ggacaggggt tcaactcccg ccagctcca       359
```

<210> SEQ ID NO 16
<211> LENGTH: 350
<212> TYPE: DNA
<213> ORGANISM: Fusobacterium mortiferum

<400> SEQUENCE: 16

```
ggggctgatt ctggattcga cggggttatg aggttatagg tagcatgcca ggatgaccgc        60
tgtgagaggt caacacatcg tttagatgga aacagaaatt acgctttagc tgcttaatta       120
gtcagctcac ctctggtttc tctcttctgt aggagaatcc aaccgaggtg ttaccaatat       180
acagattacc tttagtgatt tctctaagct caaagggaca ttttagagaa tagcttcagt       240
tagccctgtc tgcgggagtg attgttgcga aataaaatag tagactaagc attgtagaag       300
cctatggcgc tggtagtttc ggacacgggt tcaactcccg ccagctccaa                  350
```

<210> SEQ ID NO 17
<211> LENGTH: 377
<212> TYPE: DNA
<213> ORGANISM: Corynebacterium xerosis

<400> SEQUENCE: 17

```
ggggctgatt ctggattcga cttcgtacat tgagccaggg gaagcgtgcc ggtgaaggct        60
ggagaccacc gcaagcgtcg cagcaaccaa ttaagcgccg agaactctca gcgcgactac       120
gccctcgctg cctaagcagc gaccgcgtgt ctgtcagacc gggtaggcct ctgatccgga       180
ccctggcatc gtttagtggg gctcgctcgc cgacttggtc gcaagggtcg gcggggacac       240
tcacttgcga ctgggcccgt catccggtca tgttcgactg aaccggaggg ccgagcagag       300
accacgcgcg aactgcgcac ggagaagccc tggcgaggtg acggaggacc cgggttcaac       360
tcccgccagc tccacca                                                     377
```

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18

| | | | | | |
|---|---|---|---|---|---|
| ggggctattc | tggattcgac | ggtgtgtgtc | gcgtcgggag | aagcgggccg | aggatgcaga | 60 |
| gtcatctcgt | caaacgctct | ctgcaaacca | ataagtgccg | aatccaagcg | cactgacttc | 120 |
| gctctcgctg | cctgatcagt | gatcgagtcc | gtcaccccga | ggtcgctgtc | gcctcggatc | 180 |
| gtggcgtcag | ctagatagcc | actgggcgtc | accctcgccg | ggggtcgtga | cgccgacatc | 240 |
| aatccggctg | gtccgggtt | ggccgcccgt | ctgcgggacg | gccaggaccg | agcaacaccc | 300 |
| acagcagact | gcgcccggag | aagacctggc | aacacctcat | cggacgcggg | ttcaactccc | 360 |
| gcantcccac ca | | | | | 372 |

<210> SEQ ID NO 19
<211> LENGTH: 372
<212> TYPE: DNA
<213> ORGANISM: Mycobacterium smegmatis

<400> SEQUENCE: 19

| | | | | | |
|---|---|---|---|---|---|
| tcatctcggc | ttgttcgcgt | gaccgggaga | tccgagtaga | gacatagcga | actgcgcacg | 60 |
| gagaggggct | gattcctgga | ttcgacttcg | agcatcgaat | ccaggaagc | gtgccggtgc | 120 |
| aggcaagaga | ccaccgtaag | cgtcgttgca | accaattaag | cgccgattcc | aatcagcgcg | 180 |
| actacgccct | cgctgcctaa | gcgacggctg | gtctgtcaga | ccgggagtgc | cctcggcccg | 240 |
| gatcctggca | tcagctagag | ggacccaccc | acgggtcgg | tcgcgggacc | tgtggggaca | 300 |
| tcaaacagcg | actgggatcg | agcctcgagg | acatgccgta | ggacccgggt | tcaactcccg | 360 |
| ccagctccac ca | | | | | 372 |

<210> SEQ ID NO 20
<211> LENGTH: 355
<212> TYPE: DNA
<213> ORGANISM: Bacillus badius

<400> SEQUENCE: 20

| | | | | | |
|---|---|---|---|---|---|
| gggggtgatt | ctggattcga | cagggatagt | tcgagcttgg | gctgcgagcc | ggagggccgt | 60 |
| cttcgtacca | acgcaaacgc | ctaaatataa | ctggcaaaaa | agatttagct | ttagctgcct | 120 |
| aatataggtt | cagctgctcc | tcccgctatc | gtccatgtag | tcgggtaagg | ggtccaaact | 180 |
| tagtggacta | cgccggagtt | ctccgcctgg | ggacaaagga | agagatcaat | caggctagct | 240 |
| gcccggacgc | ccgtcgatag | gcaaaaggaa | cagtgaaccc | caaatatatc | gactacgctc | 300 |
| gtagacgttc | aagtggcgtt | atctttggac | gtgggttcaa | ctcccgccag | ctcca | 355 |

<210> SEQ ID NO 21
<211> LENGTH: 357
<212> TYPE: DNA
<213> ORGANISM: Bacillus brevis

<400> SEQUENCE: 21

| | | | | | |
|---|---|---|---|---|---|
| gggggcggaa | aggattcgac | ggggatggta | gagcatgaga | agcgagccgg | ggggttgcgg | 60 |

```
acctcgtcac caacgcaaac gccattaact ggcaacaaac aactttctct cgctgcttaa    120
taaccagtga ggctctccca ctgcatcggc ccgtgtgccg tggatagggc tcaactttaa    180
cgggctacgc cggaggcttc cgcctggagc caaaggaaga agaccaatca ggctaggtgc    240
caggtcagcg cgtcactccg cgaatctgtc accgaaactc taaacgagtg actgcgctcg    300
gagatgctca tgtatcgctg ttttcggacg ggggttcgat tcccgccgcc tcaccca      357

<210> SEQ ID NO 22
<211> LENGTH: 354
<212> TYPE: DNA
<213> ORGANISM: Bacillus thermoleovorans

<400> SEQUENCE: 22
gggggcggaa aggattcgac ggggtaggt cgagcttaag cggcgagccg aggggacgt      60 cctcgtaaaa acgtcaccta aagataactg gcaaacaaaa ctacgcttta gctgcctaat   120
tgctgcagct agtcctccc gccatcgccc gcgtggcgtt cgaggggctc atatggagcg    180
ggctacgccc aaatccgccg cctgaggatg agggaagaga cgaatcaggc tagccgccgg    240
gaggcctgtc ggtaggcgga acggacgcg aagcgaaata taccgactac gctcgtagat    300
gcttaagtgg cgatgcctct ggacgtgggt tcgattcccg ccgcctcccc acca          354

<210> SEQ ID NO 23
<211> LENGTH: 384
<212> TYPE: DNA
<213> ORGANISM: Clostridium innocuum

<400> SEQUENCE: 23
gggggcggaa aggattcgac ggggatatgt ctggtacaga ctgcagtcga gtggttacgt    60
aataaccaat taaatttaaa cggaaaaact aaattagcta acctctttgg tggaaaccag   120
agaatggctt tcgctgctta ataaccgata taggttcgca gccgcctctg catgcttctt    180
ccttgaccat gtggatgtgc gcgtaagacg caagggataa ggaatctggt ttgcctgaga    240
tcagattcac gaaaattctt caggcacatt catcagcgga tgttcatgac ctgctgatgt    300
cttaatcttc atggactaaa ctgtagaggt ctgtacgtgg ggctgtttct ggacaggagt    360
tcgattcccg ccgcctcacc acca                                           384

<210> SEQ ID NO 24
<211> LENGTH: 349
<212> TYPE: DNA
<213> ORGANISM: Clostridium lentocellum

<400> SEQUENCE: 24
gggggcggaa aggattcgac ggggtcaca tctactgggg cagccatccg tagaacgccg     60
gagtctacgt taaaagctgg cacttaaagt aaacgctgaa gataatttag caatcgctgc    120
ctaattaagg cgcagtcctc ctaggtcttc cgcagcctag atcagggctt cgactcgcgg    180
atccttcacc tggcaaagct ttgagccaac gtgaacacta tgaagctact aaaatctaga    240
gcctgtcttt gggcgctaga tgagggaat gtcaaaacaa agaatatgat ggtagagacc     300
acgctatatg ggctttcgga caggggttcg attcccgccg ccttcacca                349

<210> SEQ ID NO 25
<211> LENGTH: 358
<212> TYPE: DNA
<213> ORGANISM: Clostridium perfringens

<400> SEQUENCE: 25
```

```
ggggctgatt ctggattcga cgggggtaag atgggtttga taagcgagtc gagggaagca    60
tggtgcctcg ataataaagt atgcattaaa gataaacgca gaagataatt ttgcattagc   120
agcttaattt agcgctgctc atccttcctc aattgcccac ggttgagagt aagggtgtca   180
tttaaaagtg gggaaccgag cctagcaaag ctttgagcta ggaacggaat ttatgaagct   240
taccaaagag gaagtttgtc tgtggacgtt ctctgaggga attttaaaac acaagactac   300
actcgtagaa agtcttactg gtctgctttc ggacacgggt tcaactcccg ccactcca    358

<210> SEQ ID NO 26
<211> LENGTH: 362
<212> TYPE: DNA
<213> ORGANISM: Clostridium stercorarium

<400> SEQUENCE: 26
gggggcggaa aggattcgac ggggttattg aagcaagagt agcgggtaga ggattctcgt    60
tggcctcttt aaaaaacgag agctaaaaat aaacgcaaac aacgataact acgctttagc   120
tgctgcgtaa gtaacacgca gcccgtcggc cccggggttc ctgcgcctcg ggataccggc   180
gtcatcaagg cagggaacca gccggatcag gcttcaggtc cggtgggatt taatgaagct   240
accgacttat aaagcctgtc tctgggcgtt ataagaaggg aatgtcaaaa cagagactgc   300
acccggagaa gctcttgtgg atatggttcc ggacacgagt tcgattcccg ccgcctccac   360
ca                                                                   362

<210> SEQ ID NO 27
<211> LENGTH: 369
<212> TYPE: DNA
<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27
ggggctgatt atggattcga caggatngtt gagcttgaat tgcgtttcgt aggttacggc    60
tacgttaaaa cgttacagtt aaatataact gctaaaaacg aaaacaattc tttcgcttta   120
gctgcctaaa aaccagctag cgaagatcct cccggcatcg cccatgtgct cgggtcaggg   180
tcctaatcga agtgggatac gctaaatttt tccgtctgta aaatttagag gagcttacca   240
gactagcaat acaagaatgc ctgtcactcg gcacgctgta aagcgaacct ttaaatgagt   300
gtctatgaac gtagagattt aagtgggaat atgttttgga cgcgggttca actcccgcca   360
gctccacca                                                           369

<210> SEQ ID NO 28
<211> LENGTH: 353
<212> TYPE: DNA
<213> ORGANISM: Heliobacillus mobilis

<400> SEQUENCE: 28
ggggctgatt ctggattcga cggggaacgt gtttgcttgg gatgcgagcc gggttgccgc    60
caggaccgta aaagggcgg aaggctttaa ttgccgaaga taactacgct ttagctgctt   120
aattgcagtc taacctcttc tcctctgtgc tctcggtgag gatgtaaggg gtcatttaag   180
agagctggct tcgaccaatt ctcggaggtc caagcgagat ttatcgagat agcctgacca   240
acgctctgtc tgccgtgcgg aaggaaggcg aaatctaaaa cgacagacta cgctcgtagt   300
```

```
gtcctttgtg ggcatttctt cggacgcggg ttcaactccc gccagctcca cca        353
```

<210> SEQ ID NO 29
<211> LENGTH: 353
<212> TYPE: DNA
<213> ORGANISM: Heliospirillum gestii

<400> SEQUENCE: 29

```
ggggctgatt ctggattcga cggggaacgt gtttgcttag gacgcgagcc gggttgccgc   60
caggaccgta aaagggcgg aaggctttaa ttgccgaaga taactacgct ttagctgctt  120
aattgcagtc taacctcttc tcctctgtgc tctcggtgag gatgtaaggg gtcatttaag  180
agagctggct cgaaccaatt ctcggaggtt cgggtaagac ttatcgagat agcctgacca  240
acgctctgtc tgccgtgcgg aaggatggcg aaatctaaaa cgacagaata cgctcgtagt  300
gtcctttgtg ggcatttctt cggacgcggg ttcaactccc gccagctcca cca         353
```

<210> SEQ ID NO 30
<211> LENGTH: 368
<212> TYPE: DNA
<213> ORGANISM: Lactobacillus acidophilus

<400> SEQUENCE: 30

```
ggggctgatt ctggattcga caggcgtaga cccgcattga ctgcggttcg taggttacgt   60
ctacgtaaaa acgttacagt taaatataac tgcaaataac aaaaattctt acgcattagc  120
tgcttaatt agcgcatgcg ttgctctttg tcggtttact cgtggctgac actgagtatc  180
aacttagcga gttacgttta actacctcac ctgaatagtt gaaaagagtc ttagcaggtt  240
agctagtcca tactagccct gttatatggc gttttggact agtgaagttc aagtaatata  300
actatgatcg tagaggtcag tgacgagatg cgtttggaca gcgggttcaa ctcccgccag  360
ctccacca                                                          368
```

<210> SEQ ID NO 31
<211> LENGTH: 360
<212> TYPE: DNA
<213> ORGANISM: Staphylococcus epidermidis

<400> SEQUENCE: 31

```
ggggctgatt ctgcattcga caggggtccc cgagcttatt aagcgtgtgg agggttggct   60
ccgtcatcaa cacatttcgg ttaaatataa ctgacaaatc aaacaataat ttcgcagtag  120
ctgcgtaata gccactgcat cgcctaacag catctcctac gtgctgttaa cgcgattcaa  180
ccctagtagg atatgctaaa cactgccgct tgaagtctgt ttagatgaaa tataatcaag  240
ctagtatcat gttggttgtt tattgcttag catgatgcga aaattatcaa taaactacac  300
acgtagaaag atttgtatca ggacctctgg acgcgggttc aactcccgcc agctccacca  360
```

<210> SEQ ID NO 32
<211> LENGTH: 368
<212> TYPE: DNA
<213> ORGANISM: Streptococcus faecium

<400> SEQUENCE: 32

```
ggggctgatt ctggattcga caggcacagt ttgagcttga attgcgtttc gtaggttacg   60
tctacgttaa aacgttacag ttaaatataa ctgctaaaaa cgaaaacaac tcttacgctt  120
tagctgccta aaaacagtta gcgtagatcc tctcggcatc gcccatgtgc tcgagtaagg  180
gtctcaaatt tagtgggata cgtgacaact ttccgtctgt aagttgttaa agagatcatc  240
```

```
agactagcga tacagaatgc ctgtcactcg gcaagctgta aagcgaaacc acaaatgagt    300
tgactatgaa cgtagatttt taagtggcga tgtgtttgga cgcgggttca actcccgccg    360
ttccacca                                                             368

<210> SEQ ID NO 33
<211> LENGTH: 328
<212> TYPE: DNA
<213> ORGANISM: Thermoanaerobacterium saccharolyticum

<400> SEQUENCE: 33
ggggtagtag aggtaaaagt agcgagccga ggttccatct gctcgtaaaa cggtggactt     60
aaatataaac gcaaacgata atttagctta cgctgcttaa ttacaagcag ccgttcaacc    120
tttgattccc acatcaaagg attgggcgtc gatttagtgg ggaactgatt tatcaaagct    180
ttgagataaa tcggatttta tgaagctacc aaagcagtta tcctgtcact gggagaactg    240
cagagggaat gtcaaaacag tgactgcgct cggagaagct tttactgtga caccttcgga    300
ccggggttca actcccgcca gcccacca                                       328

<210> SEQ ID NO 34
<211> LENGTH: 379
<212> TYPE: DNA
<213> ORGANISM: Mycoplasma fermentans

<400> SEQUENCE: 34
ggggctgatt ctggattcga catgcattgg gtgatactaa tatcagtagt ttggcagact     60
ataatgcatc taggctttat aatcgcagaa gataaaaaag cagaagaagt taatatttct    120
tcacttatga ttgcacaaaa aatgcaatca caatcaaacc ttgctttcgc ttagttaaaa    180
gtgacaagtg gttttaaagt tgacatttc ctatatattt taaaatcggc ttttaaggag    240
aacaggagtc tgaaagggtt ccaaaaatct atattgtttg catttcggta gtatagatta    300
attagaaatg ataaactgta aaaagtattg gtattgactt ggtgtgtgga ctcgggttca    360
actcccgcca gctccacca                                                 379

<210> SEQ ID NO 35
<211> LENGTH: 373
<212> TYPE: DNA
<213> ORGANISM: Mycoplasma hyorhinis

<400> SEQUENCE: 35
ggggctgatt ctggattcga catacataaa aggatataaa ttgcagtggt cttgtaaacc     60
ataagacaat ttctttacta agcggaaaag aaaacaaaaa agaagattat tcattattaa    120
tgaatgcttc aactcaatca aatctagctt ttgcatttta aaaaactagt agaccaattt    180
gcttctcacg aattgtaatc tttatattag agaatagtta aaaatctgat cacttttaa    240 tgaatttata gatcacaggc ttttttaatc tttttgttat tttagataaa gagtcttctt    300
aaaaataact aaactgtagg aatttatatt taattatgcg tggacccggg ttcaactccc    360
gccagctcca cca                                                       373

<210> SEQ ID NO 36
<211> LENGTH: 399
<212> TYPE: DNA
<213> ORGANISM: Mycoplasma pirum

<400> SEQUENCE: 36
```

-continued

```
ggggagtcat ggttttgaca tgaatgatgg acccatagag gcagtggggt atgcccctta      60
tagctcaagg tttaaattaa ccgacaaaac tgacgaaaac gttgccgttg atacaaattt     120
attaatcaac caacaagctc aatttaacta cgcatttgca tagtataaaa aaataaattg     180
tgctactcat tgtaattagg ttactaaatt actttgtttt atatagtcct gtaactagtt     240
ctagtgatgt ctataaacta gaatgagatt tatagactta tttgttggcg gttgtgccat     300
agcctaaatc aacaaagaca atttatttat ggtactaaac tgtagattct atgatgaaat     360
tatttgtgga acgggttcg attcccgcca tctccacca                             399

<210> SEQ ID NO 37
<211> LENGTH: 385
<212> TYPE: DNA
<213> ORGANISM: Mycoplasma salivarium

<400> SEQUENCE: 37
ggggctgatt ctggattcga caggcattcg attcattatg ttgcagtggt ttgcaaacca      60
taaggcacta ggcttttttta aacgcaaaag accaaaaaac agaagatcaa gcagttgatc    120
tagcatttat gaataattca caaatgcaat caaatctagt tttcgcttag taaaattagt     180
caatttatta tggtgctcaa cataataaat ggtagtatga gcttaatatc atatgatttt     240
agttaatatg ataggatttg taactaaaact atgttataga aatttgtaaa ttatatatat    300
gacataggaa atttaattta ctaaactgta gatgcataat gttgaagatg tgtggaccgg    360
ggttcaactc ccgccagctc cacca                                           385

<210> SEQ ID NO 38
<211> LENGTH: 362
<212> TYPE: DNA
<213> ORGANISM: Herpetosiphon aurantiacus

<400> SEQUENCE: 38
gggggcggaa aggattcgac ggggagggcc aatcgtaagt ggcaagccga gacgctgagc      60
ctcgttaaat cggcaacgcc attaactggc aaaaacactt tccgcgctcc tgtagcgctt    120
gctgcctaat taaggcaaca cgtctctact agcctcagcc cgatgggctt gtagcggcga    180
cacttagtcg ggtcgctccc ctagttatgt ctgtgggcta ggggctaaga ttaacaggct    240
ggtcgtggcc cgctttgtct atcgggtggt gcaccgataa gatttaatca atagactacg    300
cttgtagatg cttgcggttt aacttttttgg acgcgggttc gattcccgcc gcctcaccac    360
ca                                                                   362

<210> SEQ ID NO 39
<211> LENGTH: 355
<212> TYPE: DNA
<213> ORGANISM: Thermomicrobium roseum

<400> SEQUENCE: 39
ggggctgatt ctggattcga cagggccgta ggtgcgagga ttgcaggtcg aggtcgccca      60
cgaactcgta aaaggggca gccaagtaac tggcgagcgc gaactcgctc tggctgcgta     120
attcacgcag ccacgtctgc ccggacccctt ccctggtggg ttcggagcgg gcgccgcaag   180 accgggggtgc ccctggccca agcgccggtg cgggccaggt caagcgtgat ccggctcggc   240
tgaccgggat cctgtcggtg ggagcctggc agcgacagta gaacaccgac taagcctgta    300
gcatatcctc ggctgaacgc tctggacgcg ggttcaactc ccgccagctc cacca          355
```

```
<210> SEQ ID NO 40
<211> LENGTH: 405
<212> TYPE: DNA
<213> ORGANISM: Chlorobium limicola

<400> SEQUENCE: 40
ggggctgatt ctggattcga caggatacgt gtgagatgtc gttgcactcc gagtttcagc    60
atggacggac tcgttaaaca agtctatgta ccattagatg cagacgatta ttcgtatgca   120
atggctgcct gattagcaca agttaactca gacgccatcg tcctgcggtg aatgcgctta   180
ctctgaagcc gccggatggc ataacccgcg cttgagccta cgggttcgcg caagtaagct   240
ccgtacattc atgcccgagg ggctgtgcgg gtaatttctc gggataaggg gacgaacgct   300
gctggcggtg taatcggccc acgaaaaccc aatcaccaga gatgagtgtg gtgactgcat   360
cgagcagtgt tttggacgcg ggttcaactc ccgccagctc cacca                    405

<210> SEQ ID NO 41
<211> LENGTH: 362
<212> TYPE: DNA
<213> ORGANISM: Pirellula staleyi

<400> SEQUENCE: 41
ggggctgatt ctggattcga ccggatagcc tgaagcgaat acggcgtgcc gtggttgatc    60
agatggccac gtaaaaagct gatcacaaac ttaactgccg agagcaatct cgcacttgct   120
gcctaactaa acggtagctt ccgactgagg gctttagccg gagaggccca aaagttggtc   180
accaaatccg gaccgcctcg tgccatgatc gaaacgcacg aggtcaaaaa agtttcgatc   240
tagtgcaggg tgtagccagc agctaggcga caaactgtgc aaaaatcaaa ttttctgcta   300
cgcacgtaga tgtgttcgtg aaaatgtctc gggacggggg ttcaactccc gccactccac   360
ca                                                                  362

<210> SEQ ID NO 42
<211> LENGTH: 346
<212> TYPE: DNA
<213> ORGANISM: Planctomyces limnophilus
<220> FEATURE:
<221> NAME/KEY: misc_feature
<222> LOCATION: (1)..(346)
<223> OTHER INFORMATION: n is an unknown base

<400> SEQUENCE: 42
ggggctgatt ctggattcga caacctctca agaggagcgt ggccactatg ggactcgatt    60
atgttgaatt cgtcatggat cttgaagaga ccttcgacat caaactggat gacaaacatt   120
tttcagcagt caaaacacca cgcgatttgg caatcattat tcgggatcaa ttagctgctg   180
aaggcagaat ctgggatgaa tcgaatgctt ttcgcaaaat ctcgaatttg aattggacga   240
tgttgcccga gttccggatg tggactcaaa tcaaaagctc tctaccagtt tcttttcacc   300
gactgcgtcc cagcacccgt ctcgttcaac tcccgccant ccacca                  346

<210> SEQ ID NO 43
<211> LENGTH: 362
<212> TYPE: DNA
<213> ORGANISM: Planctomyces maris

<400> SEQUENCE: 43
ggggctgatt ctggattcga ctggttcacc gtatgttaag gtggcggtgc cgtggttgat    60
cagttggcca cgtaaaaagc tgatcacaat ctaattgcaa acaagcaatt ttcaatggct   120
```

-continued

```
gcttaataaa agcaacccg gcttaggaat ctctgtctga ggagtccgac agctggtcac    180
aaaatcagac tggtatcaga tcaatgtccg ctccgtctga tacgagattc gtggtggact   240
ggtttccaac aggctctgtt tatcgtgccc gaagaaacga gactcaaacg ataaaatatg   300
caccgtagag gctttagctg agggttcaca ggacgcgggt tcaactcccg ccagctccac   360
ca                                                                  362
```

<210> SEQ ID NO 44
<211> LENGTH: 360
<212> TYPE: DNA
<213> ORGANISM: Alcaligenes eutrophus

<400> SEQUENCE: 44

```
ggggttgatt ctggattcga cgtgggttac aaagcagtgg agggcatacc gaggacccgt    60
cacctcgtta atcaatggga atgcaataac tgctaacgac gaacgttacg cactggccgc   120
ttaattgcgg ccgtcctcgc actggctcgc tgacgggcta gggtcgcaag accacgcgag   180
gtcatttacg tcagataagc tccggaaggg tcacgaagcc ggggacgaaa acctagtgac   240
tcgccgtcgt agagcgtgtt cgtccgcgat gcgccggtta aatcaaatga cagaactaag   300
tatgtagaac tctctgtgga gggcttacgg acgcgggttc aactcccgcc agctccacca   360
```

<210> SEQ ID NO 45
<211> LENGTH: 362
<212> TYPE: DNA
<213> ORGANISM: Alcaligenes faecalis

<400> SEQUENCE: 45

```
ggggggcggaa aggattcgac gggggtcaag aagcagcaca gggcgtgtcg agcaccagta    60
cgctcgtaaa tccactggaa aactataaac gccaacgacg agcgtttcgc tctagccgct   120
taaggctggg ccactgcact aatttgtctt tgggttaggt agggcaacct acagcagtgt   180
tatttacaaa gaatcgaatc ggtctgcgcc acgaagtccg gttctaaaac ttagtggatc   240
gccaaggaaa ggcctgtcaa ttggcatagt ccaaggttaa aacttaaaat taattgacta   300
cacatgtaga actgtctgtg gacggcttgc ggacgggggt tcgattcccg ccgcctccac   360
ca                                                                  362
```

<210> SEQ ID NO 46
<211> LENGTH: 366
<212> TYPE: DNA
<213> ORGANISM: Chromobacterium violaceum

<400> SEQUENCE: 46

```
ggggctgatt ctggattcga cggggggttgc gaagcagatg agggcatacc gggatttcag    60
tcaccccgta aaacgctgaa tttatatagt cgcaaacgac gaaacttacg ctctggcagc   120
ctaacggccg gccagacact acaacggttc gcagatgggc cggggcgtc aaaaccctgt    180 agtgtcactc tacatctgct agtgctgttc cgggttactt ggttcagtgc gaaataatag   240
gtaactcgcc aaagtccagc ctgtccgtcg gcgtggcaga ggttaaatcc aaatgacacg   300
actaagtatg tagaactcac tgtagaggac tttcggacgc gggttcaact cccgccagct   360
ccacca                                                              366
```

<210> SEQ ID NO 47
<211> LENGTH: 378
<212> TYPE: DNA
<213> ORGANISM: Hydrogenophaga palleroni -continued

```
<400> SEQUENCE: 47 gggggctgatt ctggattcga cgtgggttcg gacgcgcagc agggcatgtc gaggttctgt      60 caccctcgtaa atcagcagaa aaaaaccaac tgcaaacgac gaacgtttcg cactcgccgc     120
ttaaacaccg gtgagccttg caacagcagg ccgatgggct gggcaagggg gtcgcaagac     180
ctcccggctg caaggtaatt tacatcggct ggttctgcgt cgggcacctt ggcgcaggat     240
gagattcaag gatgctggct tcccgtttag cgtgccactg cgcgactcgg gcggcgagac     300
ccaaatcaga cggctacaca tgtagaactg ctcgaaaaag gcttgcggac ggggggttcaa     360 ctcccgccag ctccacca                                                    378

<210> SEQ ID NO 48
<211> LENGTH: 365
<212> TYPE: DNA
<213> ORGANISM: Methylobacillus glycogenes

<400> SEQUENCE: 48
gggggcggaa aggattcgac gggggttgca agcagcgca gggcataccg aggcctagtc        60
acctcgtaaa taaactagaa caagtatagt cgcaaacgac gaaacttacg ctctagccgc     120
ttaatcccgg ctggacgctg caccgaaggg cctctcggtc gggtggggta acccacagca     180
gcgtcattaa gagaggatcg tgcgatattg ggttacttaa tatcgtatta aatccaaggt     240
aactcgcctg ctgtttgctt gctcgttggt gagcatcagg ttaaatcaaa caacacagct     300
aagtatgtag aactgtctgt ggagggcttg cggacggggg ttcgattccc gccgcctcac     360
cacca                                                                  365

<210> SEQ ID NO 49
<211> LENGTH: 362
<212> TYPE: DNA
<213> ORGANISM: Nitrosomonas cryotolerans

<400> SEQUENCE: 49 gggggctgatt ctggattcga cgtgggttgc aaagcagcgc agggcatacc gaggaccaga     60
atacctcgta aatacatctg gaaaaaaata gtcgcaaacg acgaaaacta cgctttagcc     120
gcttaatacg gctagcctct gcaccgatgg gccttaacgt cgggtctggc aacagacagc     180
agagtcatta gcaaggatcg cgttctgtag ggtcacttta cagaacgtta acaataggt     240 gactcgcctg ccatcagccc gccagctggc ggttgtcagg ttaaattaaa gagcatggct     300
aagtatgtag aactgtctgt agaggacttg cggacgcggg ttcaactccc gccagtccac     360
ca                                                                     362

<210> SEQ ID NO 50
<211> LENGTH: 378
<212> TYPE: DNA
<213> ORGANISM: Pseudomonas testosteroni

<400> SEQUENCE: 50 gggggctgatt ctggattcga cgtgggttcg ggaccggtgc ggtgcatgtc gagcttgagt     60
gacgctcgta aatctccatt caaaaaacta actgcaaacg acgaacgttt cgcactcgcc     120
gcttaatccg gtgagccttg caacagcacg ctagtgggct gggcaagggg gtagcaatac     180
ctcccggctg caagggaatt tcattagct ggctggatac cgggcttctt ggtatttggc     240
gagattttag gaagctggct acccaagcag cgtgtgcctg cggggtttgg gtggcgagat     300
```

```
ttaaaacaga gcactaaaca tgtagatctg tccggcgaag gcttacggac gcgggttcaa    360
ctcccgccag ctccacca                                                   378

<210> SEQ ID NO 51
<211> LENGTH: 360
<212> TYPE: DNA
<213> ORGANISM: Ralstonia pickettii

<400> SEQUENCE: 51
gggggcggaa aggattcgac gggggttgcg aagcagcgga gggcataccg aggacccgtc     60
acctcgttaa tcaatgggaa tgcaataact gctaacgacg aacgttacgc actggcagcc    120
taagggccgc cgtcctcgca ctggctcgct gacgggctag ggtcgcaaga ccagcgaggt    180
catttacgtc agataagctt taggtgagtc acggcctag agacgaaaac ttagtgaatc     240
gccgtcgtag agcgtgttcg tccgcgatgc ggcggttaaa tcaaatgaca gaactaagta    300
tgtagaactc tctgtggagg gcttgcggac gcgggttcga ttcccgccgc ctcaccacca    360

<210> SEQ ID NO 52
<211> LENGTH: 386
<212> TYPE: DNA
<213> ORGANISM: Variovorax paradoxus

<400> SEQUENCE: 52
ggggctgatt ctggattcga cgtgggttcg gagtcgcagc ggggcatgtc gagctgaatg     60
cgctcgtaaa acagattcaa acaaactaac tgcaaacgac gaacgtttcg cactcgctgc    120
ttaattgcca gtgagccttg caacagttgg ccgatgggct gggcaagggg gtctggagca    180
atcctgacct cccggctgca aggataacta catgggctgg ctccgatccg ggtaccttgg    240 gtcgggcga gaaaataggg tactggcgtc cggtttagcg tgtgactgcg cgactccgga     300
agcgagactc aaaacagatc actaaacatg tagaactgcg cgatgaaggc ttgcggacgg    360
gggttcaact cccgccagct ccacca                                          386

<210> SEQ ID NO 53
<211> LENGTH: 346
<212> TYPE: DNA
<213> ORGANISM: Bdellovibrio bacteriovirus

<400> SEQUENCE: 53
gggggcggaa aggattcgac gggggtgctg aagcataagg agcataccgg ggcggatgag     60
gacctcgtta aaaacgtcca ctttgtaatt ggcaacgatt acgcacttgc agcttaatta    120
agcagcacga tcaaccttgt ggtggttccg cacttggatt gatcgtcatt tagggacctc    180
ggcgtgttgg gttttctcca gcagacatgc ttaaatttac tggggagag gtcttaggga     240 ttttgtctgt ggaagcccga ggaccaatct aaaacactga ctaagtatgt agcgccttat    300
cgtggatcat ttgcggacgg gggttcgatt cccgccgcct ccacca                    346

<210> SEQ ID NO 54
<211> LENGTH: 366
<212> TYPE: DNA
<213> ORGANISM: Myxococcus xanthus

<400> SEQUENCE: 54
gggggcggaa aggattcgac gggggcattg aagttcgaga cgcgtgccga gcttgtcagg     60
tagctcgtaa attcaacccg gcaaagacac aaaagccaac gacaacgttg agctcgcgct    120
ggctgcctaa aaacagccca tagtgcgcgg tccccccgcc ctcggcctgt ggggttggga    180
```

```
cagaccgtca taatgcaggc tggctgccga gggtgcctgg acccgaggtg gcgagatctt      240
cccaggaccg gctctgagta tcccgtccgt gggagcctca gggacgtagc aaatcgcgga      300
ctacgcacgt agggtcgaag agcggacggc tttcggacgc gggttcgatt cccgccgcct      360
ccacca                                                                 366

<210> SEQ ID NO 55
<211> LENGTH: 380
<212> TYPE: DNA
<213> ORGANISM: Sulfurospirillum deleyianum

<400> SEQUENCE: 55
ggggctgatt ctggattcga caggagtagt tttagcttat ggctgcatgt cgggagtgag      60
ggtcttccgt tacacaacct tcaaacaata actgctaaca acagtaacta tcgtcctgct     120
tacgcgctag ctgcgtaagt ttaacaaata atggactgct ctcccctttg atgctatctt     180
aggaggtctt ggagagtatc atagatttga tagctatatt acatgaacgc ctttacatgt     240
aatgaagtta aaggctcgtt ttgcgtagtt ttctgattgt tgtacgaagc aaaattaaac     300
actatcaaca atatctaagc atgtagacgt cataggtggc tattttttgga ctgcgggttc     360 aactcccgcc agctccacca                                                 380

<210> SEQ ID NO 56
<211> LENGTH: 359
<212> TYPE: DNA
<213> ORGANISM: Chromatium vinosum

<400> SEQUENCE: 56
ggggctgatt ctggattcga cgtgggtcgc gaaacctaag gtgcatgccg aggtgcggtt      60
gacctcgtaa acccctccgc aaacttatag ttgccaacga cgacaactac gctctcgctg     120
cttaatccca gcgggcctct gaccgtcact tgcctgtggg cggcggattc caggggtaac     180
ctcacacagg atcgtggtga cgggagtccg gacctgatcc actaaaacct aacggaatcg     240
ccgactgatc gccctgccct tcgggcggca gaaggctaaa acaatagag tgggctaagc      300 atgtaggacc gagggcagag ggcttgcgga cgcgggttca actcccgcca gctccacca     359

<210> SEQ ID NO 57
<211> LENGTH: 395
<212> TYPE: DNA
<213> ORGANISM: Pseudomonas fluorescens

<400> SEQUENCE: 57
ggggctgatt ctggattcga cgccggttgc gaacctttag gtgcatgccg agttggtaac      60
agaactcgta aatccactgt tgcaactttc tatagttgcc aatgacgaaa cctacgggga     120
atacgctctc gctgcgtaag cagccttagc ccttccctcc tggtaccttc gggtccagca     180
atcatcaggg gatgtctgta aacccaaagt gattgtcata tagaacagaa tcgccgtgca     240
gtacgttgtg gacgaagcgg ctaaaactta cacaactcgc ccaaagcacc ctgcccgtcg     300
ggtcgctgag ggttaactta atagacacgg ctacgcatgt agtaccgaca gcagagtact     360
ggcggacgcg ggttcaactc ccgccagctc cacca                                395

<210> SEQ ID NO 58
<211> LENGTH: 362
<212> TYPE: DNA
<213> ORGANISM: Borrelia afzelii
```

```
<400> SEQUENCE: 58
ggggctgatt ctggattcga ctgaaaatgc taatattgta agttgcaagc agagggaatc      60
tcttaaaact tctaaaataa atgcaaaaaa taataacttt acaagttcaa accttgtaat     120
ggctgcttaa gttagcagag agttttgttg aatttggctt tgagattcac ttatactctt     180
ttagacatcg aagcttgctt aaaaatgttt tcaagttgat ttttagggac ttttatactt     240
gagagcaatt tggcggtttg ctagtatttc caaaccatat tgcttagtaa aatactagat     300
aagcttgtag aagcttatag tattgttttt aggacgcggg ttcaactccc gccagtccac     360
ca                                                                    362

<210> SEQ ID NO 59
<211> LENGTH: 363
<212> TYPE: DNA
<213> ORGANISM: Borrelia crocidurae

<400> SEQUENCE: 59
ggggctgatt ctggattcga ctaagaactt tagtagcata aatggcaagc agagtgaatc      60
tcttaaaact tctttaataa atgcaaaaaa taataacttt acaagttcag atcttgtaat     120
ggctgcttaa tttagcagag agttttgttg gattttgctt tgaggttcaa cttatactct     180
ttaagacatc aaagtatgcc taaaaatgtt tcaagttgat ttttagggac ctttaaactt     240
gagagtaatt tggtggtttg cttgttttcc aagccttatt gcttttttcta aaaattagct     300 aagcttgtag atatttatga tattattttt aggacgcggg ttcaactccc gccagttcca     360
cca                                                                   363

<210> SEQ ID NO 60
<211> LENGTH: 365
<212> TYPE: DNA
<213> ORGANISM: Borrelia hermsii

<400> SEQUENCE: 60
ggggctgatt ctggattcga ctaaaaactt tagtagcata aattgcaagc agagggaatc      60
tcttaaaact tctttaataa atgcaagaaa taataacttt acaagttcaa atcttgtaat     120
ggctgcttaa attagcagag agttctgctg gattttgctt tgaggttcag cttatactct     180
tttaagacat caaagcttgc ttaaaaatat ttcaagttga ttttaggga cttttaaatt      240 tgagagtaat ttggcggttt gctagttttt ccaaacctta ttacttaaag aaaacactag     300
ctaagcttgt agatatttat gatattattt ttaggacgcg ggttcaactc ccgccagctc     360
cacca                                                                 365

<210> SEQ ID NO 61
<211> LENGTH: 363
<212> TYPE: DNA
<213> ORGANISM: Borrelia garinii

<400> SEQUENCE: 61
ggggctgatt ctggattcga ctgaaaatgc gaatattgta agttgcaggc agagggaatc      60
tcttaaaact tctaaaataa atgcaaaaaa taataacttt acaagctcaa accttgtaat     120
ggctgcttaa gttagcaggg agtttcgttg aatttggctt tgaggttcac ttatactctt     180
ttcgatatcg aagcttgctt aaaaatgttt tcaagttaat ttttagggac ttttgtactt     240
gagagcaatt tggcggtttg ctagtatttc caaaccatat tgcttaagta aaatgctaga     300
taagcttgta gaagcttata atattgtttt taggacgcgg gttcaactcc cgccagtcca     360
```

```
cca                                                               363

<210> SEQ ID NO 62
<211> LENGTH: 357
<212> TYPE: DNA
<213> ORGANISM: Thermodesulfobacterium commune

<400> SEQUENCE: 62
gggggcggaa aggattcgac ggggataggt aggattaaac agcaggccgt ggtcgcaccc    60
aaccacgtta aatagggtgc aaaaacacaa ctgccaacga atacgcctac gctttggcag   120
cctaagcgtg ctgccacgca cctttagacc ttgcctgtgg gtctaaaggt gtgtgaccta   180
acaggctttg ggaggcttaa tcggtggggt taagcctccc gagattacat cccacctggt   240
agggttgctt ggtgcctgtg acaagcaccc tacgagattt cccacaggc taagcctgta    300 gcggtttaat ctgaactatc tccggacgcg ggttcgattc ccgccgcctc cccacca      357

<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63
gggggcggaa aggattcgac ggggatggag tccctggga agcgagccga ggtccccacc     60
tcctcgtaaa aaaggtggga acacgaataa gtgccaacga acctgttgct gttgccgcct   120
aatagatagg cggccgtcct ctccggagtt ggctgggctc cggaagaggg cgtgagggat   180
ccagcctacc gatctgggct ccgccttccg gccggatcg ggaaggttca ggaaggctgt    240
gggaagcgac accctgcccg tgggggtcc ttcccgagac acgaaacacg ggctgcgctc    300
ggagaagccc aggggcctcc atcttcngac gcgggttcga ttcccgccac ctccacca    358

<210> SEQ ID NO 64
<211> LENGTH: 347
<212> TYPE: DNA
<213> ORGANISM: Deinococcus proteolyticus

<400> SEQUENCE: 64
gggggcggaa aggattcgac gggggaacgg aaagcgctgc tgcgtgccga ggagccgttg    60
gcctcgtaaa caaacggcaa agccattaac tggcgaaaat aactacgctc tcgctgctta   120
agtgagacag tgaccacgta gccccgcctt tggcgacgtg tgaactgaga caaaagaagg   180
ctagcttagg tgaggttcca tagccaaaag tgaaaccaaa tggaaataag gcggacggca   240
gcctgtttgc tggcagccca ggcccgacaa tttaagagca gactacgcac gtagatgcac   300
gctggatgga cctttggacg cgggttcgat tccgccagc tccacca                  347

<210> SEQ ID NO 65
<211> LENGTH: 352
<212> TYPE: DNA
<213> ORGANISM: Prosthecobacter fusiformis

<400> SEQUENCE: 65
ggggctgatt ctggattcga cggggagtac aaggatcaaa agctgcaagc cgaggtgccg    60
ttacctcgta aaacaacggc aaaaagaag tgccaacaca aatttagcat tagctgctta    120
```

```
atttagcagc tacgctcttc taacccgggc tggcagggtt agaagggtgt cataatgagc      180
cagctgcccc ttccgactcc cctaaggaag ggaaagatgt aggggatagg tgcttacaga      240
atcctgcggg agggagtctg taagtgccga aaagttaaaa ctcccgctaa gcttgtagag      300
gcttttgatt cttgctctct ggacgcgggt tcaactcccg ccagctccac ca              352

<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 66
gggnnnnatt tggaattcgc cgaatgctag aagtggaggc tgcatgccgc ggatgattcg      60
ttggccgctt taccaattcg gatcaaacaa ctaaatgcgg actctaacga gcttgccctc     120
gccgcttaat tgacggtgac gttcctccag tgaagtctgt gaattggagg agcgactact     180
tacaggctgg ccaaaagagc gggcgaccgg ccccaaggcg agatctacag gccgctggat     240
ggacggcatc ctggcagtag gaggctggac atcgagatca aatnattgcc tgagcatgga     300
gacgctttca taaaggngtt cggacaggg                                       329

<210> SEQ ID NO 67
<211> LENGTH: 318
<212> TYPE: RNA
<213> ORGANISM: Thermoanaerobacterium saccharolyticum

<400> SEQUENCE: 67 cgggggguagu agagguaaaa guagcgagcc gagguuccau cugcucguaa aacgguggac      60
uuaaauauaa acgcaaacga uaauuuagcu uacgcugccu aauuacaagc agccguucaa     120
ccuuugauuc ccacaucaaa ggauugggcg ucgauuuagu ggggaacuga uuuaucaaag     180
cuuugagaua aaucggauuu uaugaagcua ccaaagcagu uauccugucu cuggagaaac     240
ugcagaggga augucaaaac agugacugcg cucggagaag cuuuuacugu gacaccuucg     300 gaccggggguu caacuccc                                                  318

<210> SEQ ID NO 68
<211> LENGTH: 187
<212> TYPE: RNA
<213> ORGANISM: Clostridium acetobutylicum

<400> SEQUENCE: 68
aaucuggcgu cgagagcggg gaaacgagcc uuacaaagcu uugaguaagg aacggaauuu      60
augaagcuac ugaagugaaa agcuuguuug uaggcguuuc auggagggaa uguuaaaaua     120
caaacugcac ucgagaugc uuaaaugaaa ccauuuucgg acaggguuc gauucccuc        180 gccucca                                                               187

<210> SEQ ID NO 69
<211> LENGTH: 335
<212> TYPE: RNA
<213> ORGANISM: Clostridium stercorarium

<400> SEQUENCE: 69 cggggguuauu gaagcaagag uagcggguag aggauucucg uuggccucuu uaaaaaacga      60
gagcuaaaaa uaaacgcaaa caacgauaac uacgcuuuag cugcugcgua aguaacacgc     120
```

-continued

```
agcccgucgg ccccgggguu ccugcgccuc gggauaccgg cgucaucaag gcagggaacc    180
agccggauca ggcuucaggu ccggugggau uuaaugaagc uaccgacuua uaaagccugu    240
cucugggcgu uauaagaagg gaaugucaaa acagagacac caaugcaccc ggagaagcuc    300
uuguggauau gguuccggac acgaguucga uuccc                               335
```

<210> SEQ ID NO 70
<211> LENGTH: 336
<212> TYPE: RNA
<213> ORGANISM: Clostridium perfringens

<400> SEQUENCE: 70

```
cgggguaag auggguuuga uaagcgaguc gagggaagca uggugccucg auaauaaagu     60
augcauuaaa gauaaacgca gaagauaauu uugcauuagc agcuuaauuu agcgcugcuc    120
auccuuccuc aauugcccac gguugagagu aagggguguca uuuaaaagug gggaaccgag   180
ccuagcaaag cuuugagcua ggaacggaau uuaugaagcu uagaggaagu uugucugugg    240
acguucucug agggaauuuu aaaacacaag acacuaaaau cuaguacacu cguagaaagu    300
cuuacugguc ugcuuucgga cacggguuca acuccc                              336
```

<210> SEQ ID NO 71
<211> LENGTH: 305
<212> TYPE: RNA
<213> ORGANISM: Clostridium lentocellum

<400> SEQUENCE: 71

```
cgggggucac aucuacuggg gcagccaucc guagaacgcc ggagucuacg uuaaaagcug     60
gcacuuaaag uaaacgcuga agauaauuua gcaaucgcug ccuaauuaag gcgcaguccu    120
ccuaggucuu ccgcagccua gaucagggcu ucgacucgcg gauccuucac cuggcaaagc    180
uuugagccaa cgugaacacu augaagcuag ccugucuuug ggcgcuagau ggagggaaug    240
ucaaaacaaa gaauaugaug guagagacca cgcuauaugg gcuuucggac aggguucga     300 uuccc                                                                305
```

<210> SEQ ID NO 72
<211> LENGTH: 319
<212> TYPE: RNA
<213> ORGANISM: Heliobacillus mobilis

<400> SEQUENCE: 72

```
cggggaacgu guuugcuugg gaugcgagcc ggguugccgc caggaccgua aaaagggcgg     60
aaggcuuuaa uugccgaaga uaacuacgcu uuagcugcuu uauugcaguc uaaccucuuc    120
uccucugugc ucucggugag gauguaaggg gucauuuaag agagcuggcu ucgaccaauu    180
cucggagguc caagcgagau uuaucgagau agccugacca acgcucuguc ugccgugcgg    240
aaggaaggcg aaaucuaaaa cgacagauac gcucguagug uccuuugugg gcauuucuuc    300
ggacgcgggu ucaacuccc                                                 319
```

<210> SEQ ID NO 73
<211> LENGTH: 321
<212> TYPE: RNA
<213> ORGANISM: Heliospirillum gestii

<400> SEQUENCE: 73

```
cggggaacgu guuugcuuag gacgcgagcc ggguugccgc caggaccgua aaaagggcgg     60
```

```
aaggcuuuaa uugccgaaga uaacuacgcu uuagcugcuu aauugcaguc uaaccucuuc    120
uccucugugc ucucggugag gauguaaggg gucauuuaag agagcuggcu cgaaccaauu    180
cucggagguu cgguaagac uuaucggau cagccugacc aacgcucugu cugccgugcg     240
gaaggauggc gaaaucuaaa acgacagaau acgcucguag ugoccuuugu gggcauuucu    300 ucggacgcgg guucaacucc c                                             321

<210> SEQ ID NO 74
<211> LENGTH: 325
<212> TYPE: RNA
<213> ORGANISM: Brevibacillus brevis

<400> SEQUENCE: 74
cggggauggu agagcaugag aagcgagccg gggggcuugcg gaccucguca ccaacgcaaa    60
cgccauuaac uggcaacaaa caacuuucuc ucgcugcuua auaaccagug aggcucuccc   120
acugcaucgg cccgugugcc guggauaggg cucaacuuua acgggcuacg ccggaggcuu   180
ccgccuggag ccaaaggaag aagaccaauc aggcuaggug ccaggucagc gcgucacucc   240
gcgaaucugu caccgaaacu cuaaacgagu gacugcgcuc ggagaugcuc auguaucgcu   300
guuuucggac gggggugcga uuccc                                        325

<210> SEQ ID NO 75
<211> LENGTH: 360
<212> TYPE: RNA
<213> ORGANISM: Bacillus subtilis

<400> SEQUENCE: 75
ggggacguua cggauucgac agggauggau cgagcuugag cugcgagccg agaggcgauc    60
ucguaaacac gcacuuaaau auaacuggca aaacuaacag uuuuaaccaa aacguagcau   120
uagcugccua auaagcgcag cgagcucuuc cugacauugc cuaugugucu gugaagagca   180
cauccaagua ggcuacgcuu gcguucccgu cugagaacgu aagaagagau gaacagacua   240
gcucucggaa ggcccgcccg caggcaagaa gaugagugaa accauaaaua ugcaggcuac   300
gcucguagac gcuuaaguaa ucgauguuuc uggacguggg uucgacuccc accgucucca   360

<210> SEQ ID NO 76
<211> LENGTH: 325
<212> TYPE: RNA
<213> ORGANISM: Bacillus badius

<400> SEQUENCE: 76
cagggauagu ucgagcuugg gcugcgagcc ggagggccgu cuucguacca acgcaaacgc    60
cuaaauauaa cuggcaaaaa agauuuagcu uuagcugcca aauauagguu cagcugcucc   120
ucccgcuauc guccauguag ucgguaagg gguccaaacu uaguggacua cgccggaguu   180
cuccgccugg ggacaaagga agagaucaau caggcuagcu gcccgacgc ccgucgauag    240 gcaaaaggaa cagugaaccc caaauauauc gacuacgcuc guagacguuc aaguggcguu   300
aucuuuggac gugggguucaa cuccc                                      325

<210> SEQ ID NO 77
<211> LENGTH: 341
<212> TYPE: RNA
<213> ORGANISM: Bacillus megaterium

<400> SEQUENCE: 77
ggggacguua cggauucgac agggauguuc gagcuuaggu ugcgagucga ggagauggcc    60
```

```
ucguuaaaac aucaacgcca auaauaacug gcaaaucuaa caauaacuuc gcuuuagcug    120
cauaauagua gcuuagcguu ccuccccuca ucgcccaugu gguaggguaa gggacucacu    180
uuaagugggc uacgccggag uucgccgucu gaggacgaag gaagagaaua aucagacuag    240
cgacugggac gccuguuggu aggcagaaca gcucgcgaau gaucaauaug ccaacagccg    300
uacacucgua gacgcuuaag uggccauauu ucuggacgug g                       341

<210> SEQ ID NO 78
<211> LENGTH: 315
<212> TYPE: RNA
<213> ORGANISM: Bacillus thermoleovorans

<400> SEQUENCE: 78
cggggguagg ucgagcuuaa gcggcgagcc gagggggacg uccucguaaa acgucaccu     60 aaagauaacu ggcaaacaaa acuacgcuuu agcugccuaa uugcugcagc uagcuccucc    120
cgccaucgcc cgcguggcgu ucgaggggcu cauauggagc gggcuacgcc caaauccgcc    180
gccugaggau gagggaagag acgaaucagg cuccggagg ccugucggua ggcggaacgg     240
acggcgaagc gaaauauacc gacuacgcuc guagaugcuu aaguggcgau gccucuggac    300 gugggguucga uuccc                                                   315

<210> SEQ ID NO 79
<211> LENGTH: 335
<212> TYPE: RNA
<213> ORGANISM: Enterococcus faecium

<400> SEQUENCE: 79
caggcacagu uugagcuuga auugcguuuc guagguuacg ucuacguuaa aacguuacag     60
uuaaauauaa cugcuaaaaa cgaaaacaac ucuuacgcuu uagcugccua aaaacaguua    120
gcguagaucc ucucggcauc gcccaugugc ucgaguaagg gucucaaauu uaguggggaua   180 cgugacaacu uuccgucugu aaguuguuaa agagaucauc agacuagcga uacagaaugc    240
cugucacucg gcaagcugua aagcgaaacc acaaaugagu ugauaugaac guagauuuuu    300
aaguggcgau guguuuggac gcgggucaa cuccc                               335

<210> SEQ ID NO 80
<211> LENGTH: 364
<212> TYPE: RNA
<213> ORGANISM: Enterococcus faecalis

<400> SEQUENCE: 80
gggggcguua cggauucgac aggcauaguu gagcuugaau ugcguuucgu agguuacggc     60
uacguuaaaa cguuacaguu aaauauaacu gcuaaaaacg aaacaauuc uuucgcuuua    120 gcugccuaaa aaccagcuag cgaagauccu cccggcaucg cccaugugcu cgggucaggg    180
uccuaaucga aguggggauac gcuaaauuuu ccgucugua aaauuuagag gagcuuacca    240
gacucagcaa uacagaaugc cugucacucg gcacgcugua aagcgaaccu uuaaaugagu    300
guuaugaacg uagagauuua aguggcaaua uguuuggacg cgggucgac ucccgccguc    360 ucca                                                                364

<210> SEQ ID NO 81
<211> LENGTH: 346
<212> TYPE: RNA
<213> ORGANISM: Streptococcus pyogenes
```

```
<400> SEQUENCE: 81
gggguuguua cggauucgac aggcauuaug aggcauguuu ugcgucccau cggcagaugu    60
aaauugccag uuaaauauaa cugcaaaaaa uacaaacucu uacgcuuuag cugccuaaaa   120
accagcuagc gugacuucua caagauugcu uguguccugu uagaagcucu aaaauagcaa   180
gcuacgguua cgaaauuguc uaguuucgug acaagagauu gauagacucc gcaaacuaau   240
ggcuugaguu auguguucuuu aguuuguaa augaagacau aaccuaugga cguagacaaa   300
uauguuggca gguguuugga cgugggguucg acucccacca gcucca               346

<210> SEQ ID NO 82
<211> LENGTH: 344
<212> TYPE: RNA
<213> ORGANISM: Streptococcus pneumoniae

<400> SEQUENCE: 82
ggggucguua cggauucgac aggcauuaug aggcauauuu ugcgacucgu guggcgacgu    60
aaacgcucag uuaaauauaa cugcaaaaaa uaacacuucu uacgcucuag cugccuaaaa   120
accagcaggc gugacccgau uuggauugcu cguguucaau gacaggucuu auuauuagcg   180
agauacgauu aagccuuguc uagcgguuug auaagagauu gauagacucg caguuucuag   240
acuugaguua ugugucgagg ggcuguuaaa auaauacaua acuaugguug uagacaaaua   300
uguuggcagg uguuuggacg ugggguucgac ucccaccggc ucca                 344

<210> SEQ ID NO 83
<211> LENGTH: 364
<212> TYPE: RNA
<213> ORGANISM: Streptococcus gordonii

<400> SEQUENCE: 83
ggggucguua cggauucgac aggcauuaug aggcauauuu ugcgacucau cuagcggaug    60
uaaaacgcca guuaaauaua acugcaaaaa auaauacuuc uuacgcuuua gcugccuaaa   120
aaccagcggg cgugacccga uucggauugc uugugucuga gacaggucuu auuauuagc   180 aagcuacggu agaaucuugu cuagugauuu acaagagau ugauagacua cguuagaacu   240
gagucagccg cuugauuugg gcuuaguua ugugucaaaa ucaaguuaaa acaauacaua   300
gcuaugguug uagacaaaua uguuggcaga guuuggacg ugggguucgac ucccaccggc   360 ucca                                                              364

<210> SEQ ID NO 84
<211> LENGTH: 329
<212> TYPE: RNA
<213> ORGANISM: Streptococcus mutans

<400> SEQUENCE: 84
ggggucguua cggauucgac aggcauuaug agaccuauuu ugcgacucau cuagcggaug    60
uaaaacgcca guuaaauaua acugcaaaaa auacaaauuc uuacgcagua gcugccuaaa   120
aaccagccug ugugaucaau aacaaauugc uuguguuugu gauuggucu uauuguuaac   180 aagcugcugu ucuaaaagag uucuacugac uccgcaucgu uagaguuuga guuauguauu   240 guaacgugu uaaauaaaca cauaaccuau aguguagac aaaugggguua gcagauguuu   300 ggacgugggu ucgacucccaccggcucca                                    329

<210> SEQ ID NO 85
<211> LENGTH: 328
```

-continued

```
<212> TYPE: RNA
<213> ORGANISM: Staphylococcus epidermidis

<400> SEQUENCE: 85
cagggguccc cgagcuuauu aagcgugucg gaggguuggc uccgucauca acacauuucg      60
guuaaauaua acugacaaau caaacaauaa uuucgcagua gcugcguaau agccacugca     120
ucgccuaaca gcaucccua cgugcuguua acgcgauuca acccaguag gauaugcuaa      180 acacugccgc uugaagucug uuuagaugaa auauaaucaa gcuaguauca uguugguugu    240
uuauugcuua gcaugaugcg aaaauuauca auaaacuaca cacguagaaa gauuuguauc    300
aggaccucug gacgcggguu caacuccc                                       328

<210> SEQ ID NO 86
<211> LENGTH: 359
<212> TYPE: RNA
<213> ORGANISM: Staphylococcus aureus

<400> SEQUENCE: 86
ggggacguuc auggauucga cagggguccc ccgagcucau uaagcgguguc ggaggguugu    60 cuucgucauc aacacacaca guuuauaaua acuggcaaau caaacaauaa uuucgcagua   120
gcugccuaau cgcacucugc aucgccuaac agcauuuccu augugcuguu aacgcgauuc   180
aaccuuaaua ggauaugcua acacugccg uuugaagucu guuuagaaga acuuaauca    240 aacuagcauc auguuggug uuuaucacuu uucaugaugc gaaaccuauc gauaaacuac   300
acacguagaa agaugugugu caggaccuuu ggacgcgggu ucaaaucccg ccgucucca   359

<210> SEQ ID NO 87
<211> LENGTH: 334
<212> TYPE: RNA
<213> ORGANISM: Lactobacillus acidophilus

<400> SEQUENCE: 87
caggcguaga cccgcauuga cugcgguucg uagguuacgu cuacguaaaa acguuacagu     60
uaaauauaac ugcaaauaac aaaaauucuu acgcauuagc ugcuuaauuu agcgcaugcg   120
uugcucuuug ucgguuuacu cguggcugac acugaguauc aacuuagcga guuacguuua   180
acuaccucac cugaauaguu gaaaagaguc uuagcagguu agcuagucca uacuagcccu   240 guuuauauggc guuuuggacu agugaaguuc aaguaauaua acuaugaucg uagaggucag   300
ugacgagaug cguuuggaca ggguucaac uccc                                 334

<210> SEQ ID NO 88
<211> LENGTH: 347
<212> TYPE: RNA
<213> ORGANISM: Aquifex aeolicus

<400> SEQUENCE: 88
gggggcggaa aggauucgac ggggacaggc gguccccgag gagcaggccg gguggcuccc     60
guaacagccg cuaaaacagc ucccgaagcu gaacucgcuc ucgcugccua auuaaacggc   120
agcgcguccc cgguagguuu gcgguggcc uaccggaggg cgucagagac acccgcucgg    180
gcuacucggu cgcacggggc ugaguagcug acaccuaacc cgugcuaccc ucggggagcu    240
ugcccguggg cgacccgagg ggaaauccug aacacgggcu aagccguguag agccucggau    300 guggccgccg uccucggacg cgggucgau uccgccgcc uccacca                    347

<210> SEQ ID NO 89
```

```
<211> LENGTH: 355
<212> TYPE: RNA
<213> ORGANISM: Thermotoga maritima

<400> SEQUENCE: 89
gggggcgaac gguuucgacg gggauggagu ccccugggaa gcgagccgag gucccccaccu    60 ccucguaaaa aagguggac aaagaauaag ugccaacgaa ccuguugcug uugccgcuua    120
auagauaagc ggccguccuc uccgaaguug gcugggcuuc ggaagagggc gugagagauc    180
cagccuaccg auucaguucg ccuuccggcc ugaaucggga aaacucagga aggcuguggg    240
agaggacacc cugcccgugg gagucccuc ccgagagcga aaacacgggc ugcgcucgga    300
gaagcccagg ggccuccauc uucggacggg gguucgaauc ccccccgccuc cacca        355

<210> SEQ ID NO 90
<211> LENGTH: 355
<212> TYPE: RNA
<213> ORGANISM: Thermotoga neapolitana

<400> SEQUENCE: 90
gggggcggaa aggauucgac ggggauggag uccccuggga agcgagccga ggucccccacc    60 uccucguaaa aaggguggga acacgaauaa gugccaacga accuguugcu guugccgccu    120
aauagauagg cggccguccu uccggaguu ggcugggcuc cggaagaggg cgugagggau    180
ccagccuacc gaucugggcu ccgccuuccg gcccggaucg ggaagguuca ggaaggcugu    240
gggaagcgac acccugcccg uggggggucc uucccgagac acgaaacacg ggcugcgcuc    300
ggagaagccc agggggccucc aucuucggac ggggguucga uucccgccgc cucca         355

<210> SEQ ID NO 91
<211> LENGTH: 350
<212> TYPE: RNA
<213> ORGANISM: Thermus thermophilus

<400> SEQUENCE: 91
gggggugaaa cggucucgac gggggucgcc gagggcgugg cugcgcgccg aggugcgggu    60
ggccucguaa aaacccgcaa cggcauaacu gccaacacca acuacgcucu cgcggcuuaa    120
ugaccgcgac cucgcccggu agcccugccg ggggcucacc ggaagcgggg acacaaaccc    180
ggcuagcccg gggccacgcc cucuaaccc gggcgaagcu ugaaggggc ucgcuccugg    240 ccgcccguccc gcgggccaag ccaggaggac acgcgaaacg cggacuacgc gcguagaggc    300
cacgccccgg cgaccuucgg acgggguuc gauuccccc accuccacca                 350

<210> SEQ ID NO 92
<211> LENGTH: 349
<212> TYPE: RNA
<213> ORGANISM: Deinococcus radiodurans

<400> SEQUENCE: 92
gggggugacc cgguuucgac agggaacug aaggugaugu ugcgugucga ggugccguug    60
gccucguaaa caaacggcaa agccauuuaa cuggcaacca gaacuacgcu cucgcugcuu    120
aagugagaug acgaccgugc agcccggccu uuggcgucgc ggaagucacu aaaaaagaag    180
gcuagcccag gcgauucucc auagccgacg gcgaaacuuu auggagcuac ggccugcgag    240
aaccugccca cuggugagcg ccggcccgac aaucaaacag ugggauacac acguagacgc    300
acgcuggacg gaccuuugga cggcgguucg acuccgccca ccuccacca                349
```

<210> SEQ ID NO 93
<211> LENGTH: 347
<212> TYPE: RNA
<213> ORGANISM: Deinococcus proteolyticus

<400> SEQUENCE: 93

| | | | | | |
|---|---|---|---|---|---|
| gggggcggaa | aggauucgac | gggggaacgg | aaagcgcugc | ugcgugccga | ggagccguug | 60 |
| gccucguaaa | caaacggcaa | agccauuaac | uggcgaaaau | aacuacgcuc | ucgcugcuua | 120 |
| agugagagca | gugaccacgu | agccccgccu | uuggcgacgu | gugaacugag | acaaaagaag | 180 |
| gcuagcuuag | gugagguucc | auagccaaaa | gugaaaccaa | auggaaauaa | ggcgacggc | 240 |
| agccuguuug | cuggcagccc | aggcccgaca | auuuaagagc | agacuacgca | cguagaugca | 300 |
| cgcuggaugg | accuuggac | ggcgguucga | uucccgccgc | cucacca | | 347 |

<210> SEQ ID NO 94
<211> LENGTH: 334
<212> TYPE: RNA
<213> ORGANISM: Thermomicrobium roseum

<400> SEQUENCE: 94

| | | | | | |
|---|---|---|---|---|---|
| cagggccgua | ggugcgagga | uugcaggucg | aggucgccca | cgaacucgua | aaaggggca | 60 |
| ccaaguaacu | ggcgagcgcg | aacucgcucu | ggcugcguaa | uucacgcagc | cacgucugcc | 120 |
| cggacccuuc | ccugguggu | ucggagcggg | cgccgcaaga | ccggggugcc | ccuggcccaa | 180 |
| gcgccggugc | gggccagguc | aagcgugauc | cggcucggcu | gaccgggauc | cugucggugg | 240 |
| gagccuggca | gcgacaguag | aacaccgacu | aagccuguag | cauauccucg | gcugaacgcu | 300 |
| cuggacgggg | guucaacucc | cgccagcucc | acca | | | 334 |

<210> SEQ ID NO 95
<211> LENGTH: 353
<212> TYPE: RNA
<213> ORGANISM: Coprothermobacter proteolyticus

<400> SEQUENCE: 95

| | | | | | |
|---|---|---|---|---|---|
| gggggcggaa | aggauucgac | ggggagucgg | agccuugagc | ugcaggcagg | guuggcugcc | 60 |
| acaccuuaaa | aagggguagca | aggcaaaaau | aaaugccgaa | ccagaauuug | cacuagcugc | 120 |
| uuaauguaag | cagccgcucu | ccaaacugag | gcugcauaag | uuuggaagag | cgucaaccca | 180 |
| ugcagcggcu | cuuaagcagu | ggcaccagcu | guuuaagggu | gaaagagug | gugcugggca | 240 |
| gugcgguugg | gcuuccuggg | cugcacuguc | gagacuucac | aggagggcua | agccuguaga | 300 |
| cgcgaaaggu | ggcggcucgu | cggacgcggg | uucgauuccc | gccgccucca | cca | 353 |

<210> SEQ ID NO 96
<211> LENGTH: 360
<212> TYPE: RNA
<213> ORGANISM: Herpetosiphon aurantiacus

<400> SEQUENCE: 96

| | | | | | |
|---|---|---|---|---|---|
| gggggcggaa | aggauucgac | ggggagggcc | aaucguaagu | ggcaagccga | gacgcugagc | 60 |
| cucguuaaau | cggcaacgcc | auuaacuggc | aaaaacacuu | uccgcgcucc | uguagcgcuu | 120 |
| gcugccuaau | uaaggcaaca | cgucucuacu | agccucagcc | cgaugggcuu | guagcggcga | 180 |
| cacuuagucg | ggucgcuccc | cuaguuaugu | cuguggggcua | ggggcuaaga | uuaacaggcu | 240 |
| ggucguggcc | cgcuuugucu | aucgggguggu | gcaccgauaa | gauuuaauca | auagacuacg | 300 |
| cuuguagaug | cuugcggguuu | aacuuuuugg | acgcggguuc | gauucccgcc | gccuccacca | 360 |

```
<210> SEQ ID NO 97
<211> LENGTH: 355
<212> TYPE: RNA
<213> ORGANISM: Thermodesulfobacterium commune

<400> SEQUENCE: 97
gggggcggaa aggauucgac ggggauaggu aggauuaaac agcaggccgu ggucgcaccc      60
aaccacguua aauagggugc aaaaacacaa cugccaacga auacgccuac gcuuuggcag     120
ccuaagcgug cugccacgca ccuuuagacc uugccugugg gucuaaaggu gugugaccua     180
acaggcuuug ggaggcuuaa ucggugggu uaagccuccc gagauuacau cccaccuggu      240
aggguugcuu ggugccugug acaagcaccc uacgagauuu cccacaggc uaagccugua      300 gcgguuuaau cugaacuauc uccggacgcg gguucgauuc ccgccgccuc cacca          355

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98
gggnnnnauu uggaauucgc cgaaugcuag aaguggaggc ugcaugccgc ggaugauucg      60
uuggccgcuu uaccaauucg gaucaaacaa cuaaaugcgg acucuaacga gcuugcccuc     120
gccgcuuaau ugacggugac guuccuccag ugaagucugu gaauuggagg agcgacuacu     180
uacaggcugg ccaaaagagc gggcgaccgg ccccaaggcg agaucuacag gccgcuggau     240
ggacggcauc cuggcaguag gaggcuggac aucgagauca aaunauugcc ugagcaugga     300
gacgcuuuca uaaaggnguu cggacaggg                                       329

<210> SEQ ID NO 99
<211> LENGTH: 351
<212> TYPE: RNA
<213> ORGANISM: Dictyoglomus thermophilum

<400> SEQUENCE: 99
gggggcggaa aggauucgac ggggaguaca aggaucaaaa gcugcaagcc gaggugccgu      60
uaccucguaa aacaacggca aaaagaagu gccaacacaa auuuagcauu agcugcuuaa      120
uuuagcagcu acgcucuucu aacccgggcu ggcaggguua gaagggguguc auaaugagcc    180 agcugccccu uccgacuccc cuaaggaagg gaaagaugua ggggauaggu gcuuacagaa     240
uccugcggga gggagucugu aagugccgaa aaguuaaaac ucccgcuaag cuuguagagg     300
cuuuugauuc uugcucucug gacgcggguu cgauucccgc cgccuccacc a              351

<210> SEQ ID NO 100
<211> LENGTH: 399
<212> TYPE: RNA
<213> ORGANISM: Synechocystis sp. PCC 6803

<400> SEQUENCE: 100
ggggccgcaa ugguuucgac agguuggcga aagcuugccc gugauacagg ucagagaguga     60 gucuccucuc gcaaaucaaa ggcucaaaaa aaaguaacug cgaauaacau cgucagcuuc     120
aaacgggaug ccauagcagc cuagucugua aaagcuacau uuucuuguca aagaccguuu     180
acuucuuuuc ugacuccguu aaggauuaga gguuaacccc aacggaugcu uuguuuggcu     240
```

```
cuucucuagu uagcuaaaca aucaagacuc agacuagagc aucccaccau cagggauaau    300
cgauggcccc cguccuaggg cuagaaggac uaaaccgugu aaugagcgga aaguuaauac    360
ccaguuugga cagcaguuca auucugcucg gcuccacca                           399
```

<210> SEQ ID NO 101
<211> LENGTH: 385
<212> TYPE: RNA
<213> ORGANISM: Nostoc muscorum

<400> SEQUENCE: 101

```
ggguccgucg guuucgacag guuggcgaac gcuacucugu gauucagguc gagagugagu    60
cuccucugca aaucaaggcu caaaacaaaa guaaaugcga auaacaucgu uaaauuugcu    120
cguaaggacg cucuaguagc ugccuaaaua gcccucuuca gguucgagcg ucuucgguuu    180
gacuccguua aggacugaag accaacccccc aacggaugcu cuagcaaugu ucucugguug    240
gcuugcuagc uaagauuuaa ucagagcauc cuacguucgg gauaaugaac gauucccgcc    300 uugagggguca gaaaggcuaa accgugaau gagcgggggg ucaauaccca auuggacag     360 caguucgacu cugcucgauc cacca                                          385
```

<210> SEQ ID NO 102
<211> LENGTH: 393
<212> TYPE: RNA
<213> ORGANISM: Synechococcus PCC 6301

<400> SEQUENCE: 102

```
ggggcuguaa ugguuucgac guguggguga auccuucacc gugauucagg ccgagaggga    60
guccacucuc guaauccag gcucaaccaa aaguaacugc gaacaacauc guuccuuucg     120
cucguaaggc ugcuccugua gcugcuuaaa cgccacaaac uuucggcuc gagcgucuag    180 ucguagacuc cguuaauacg ccuagacuua accccccaac ggaugcugag uggcggccuc    240
agguccgucc ucucgcuaag caaaaaccug agcaucccgc caacggggau aaucguuggc    300
ucccgcacag ugggucaacc gugcuaagcc ugugaacgag cggaaaguua cuagucaaug    360
cggacagcgg uucgauuccg cucagcucca cca                                 393
```

<210> SEQ ID NO 103
<211> LENGTH: 312
<212> TYPE: RNA
<213> ORGANISM: Leptolyngbya sp. (ATCC 27894)

<400> SEQUENCE: 103

```
ggcucaaaaa aauagaugca aacaacaucg uaccuuucgc ucguaaaacu gcaccuguug    60
cagcauaaaa caccucuaau ucagguucga gcgcuuaccg ucugacaccg uuaaagauag    120
uaagcacaac cccaacgguu gcucuagaau uucgccuuug gucggcauuc uagcuaagac    180
aauaccaaag caauccuauug uccgggacaa aggacaguuc ccgcuucgag gauuagagaa    240
gcuaaaccug ugaaugauug auagagcuaa uacccaguuu ggacacgggu ucaacucccg    300
ccagcuccac ca                                                        312
```

<210> SEQ ID NO 104
<211> LENGTH: 323
<212> TYPE: RNA
<213> ORGANISM: Porphyra purpurea

<400> SEQUENCE: 104

```
gggcugcaa gguuucuaca uugugaaaaa acaaauauau gaaaguaaaa cgagcucauu      60
auuagagcuu uuaguuaaau aaaugcagaa aauaauauua uugcuuuuuc ucgaaaauua    120
gcuguugcau aaauagucuc aauuuuugua auucgaagug auagacucuu auacacuacg    180
aauauucugu uagaguugcu cuuaauaaaa gaaaaguaaa aaaauacaaa ucuuauguu     240 uuuuaccuga auugauucaa uuuaagguua guauuuuug auuuuacaa uggacguggg      300 uucaagcccc accagcucca cca                                            323

<210> SEQ ID NO 105
<211> LENGTH: 294
<212> TYPE: RNA
<213> ORGANISM: Cyanophora paradoxa

<400> SEQUENCE: 105
ggggcuguuu agguuucgac guuuuuucu aauuauguuu guuaagcaag ucgaggauuu     60
guucuaucuc gaaaucaag aacucucaaa auuuaaacgc aacuaauauu guacguuuua    120
accguaaagc agcuuucgcu guuuaauaau uacuuuaau uuaaaaaccu aauuuuuuua    180
ggaauuuauu uauuuauugu uuauccugcu uaugaauaa aaaaaagcua acuugugaa     240 uaaacgcaua auuuaaaaaa acggacgugg guucaaaucc caccagcucc acca         294

<210> SEQ ID NO 106
<211> LENGTH: 371
<212> TYPE: RNA
<213> ORGANISM: Odontella sinensis

<400> SEQUENCE: 106
ggggcugacu ugguuucgac auuuaaaaau uguuacagua ugaugcaggu cgaaguuucu    60
aaucuucgua aaaaagaga aauuuauaau aaagcuaauu aauuuaauuu cuucuguguu   120
uaaaaguuua ucaacuaagc aaaauaguuu aaauuuaagu uuugcuguuu aaguuuuaug   180
cacauuuaau gaucuaguaa auaacuuugu ucgcuauaau uuauauuuau aacuagacuu   240
uugucuuuuu uauaguuuag aauaacuuua ucauuucaaa ccucguucca ucuaguugaa   300
cuaaaccugu gaacgaauac uauaauaaaa uuuuuagaug gacgugggu cgacucccau    360 cagcuccacc a                                                        371

<210> SEQ ID NO 107
<211> LENGTH: 348
<212> TYPE: RNA
<213> ORGANISM: Thls. weiss*

<400> SEQUENCE: 107
ggggcugauu ugguuucgac auuuaaaacu ucuuucuaug ugucagguca aaguuuguau    60
ucuuuguaaa aaaauacuaa aauacuaauaa aaugcuaauaa auauaauacc guuuauuuu   120 aaagcaguaa aaacaaaaaa agaagcaaug gcuuaaaauu uugcuguaua guucauuaac   180
uuagguuauu aaauauuuuu ucauuauaac uggacuuuuu cucaguuuau aguuagaau    240 aaauuuaaau uuugcaaaac ucguucgaaa auuuucgggc uaaaccugua aacgcaaaua   300
cuaagaaauu uuagauggac augggguucaa uucccaucag uuccacca               348

<210> SEQ ID NO 108
<211> LENGTH: 330
<212> TYPE: RNA
<213> ORGANISM: Guillardia theta

<400> SEQUENCE: 108
```

```
ggggcugauu uggauucgac auauaaauuu gcguguuuca uuaugaagca agucaaguuu    60
aaugaucuug uaaaaaacau uaaaguacaa auaaaugcaa gcauauagu uucauuuagu   120 ucaaaacguu uagucucuuu ugcauaagca aaauguguua auaacuuucu aguagaaau   180 uggagaaguu uacuaagauu uauauuuacu ccauaauuau uuuaaagaug guaaaaaggu   240
gauucaucau uuguauguuu cuaaacuuug ugaaagaaua gugggcucca uuuauaauga   300
acgugggguc aaaucccacc agcuccacca                                   330
```

```
<210> SEQ ID NO 109
<211> LENGTH: 353
<212> TYPE: RNA
<213> ORGANISM: Mycoplasma hyorhinis

<400> SEQUENCE: 109
cauacauaaa aggauauaaa uugcaguggu cuuguaaacc auaagacaau uucuuuacua    60
agcggaaaag aaacaaaaa agaagauuau ucauuauuaa ugaaugcuuc aacucaauca   120
aaucuagcuu uugcauuuua aaaaacuagu agaccaauuu gcuucucacg aauuguaauc   180
uuuauauuag agaauaguua aaaaucugau cacuuuuuaa ugaauuuaua gaucacaggc   240
uuuuuuaauc uuuuuguuau uuuagauaaa gagucuucuu aaaaauaacu aaacuguagg   300
aauuuauauu uaauuaugcg uggacccggg uucaacuccc gccagcucca cca         353
```

```
<210> SEQ ID NO 110
<211> LENGTH: 411
<212> TYPE: RNA
<213> ORGANISM: Mycoplasma capricolum

<400> SEQUENCE: 110
ggggauguca uggauuugac aggauaucuu uaguacauau aagcaguagu guuguagacu    60
auaaauacua cuagguuuaa aaaaacgcaa auaaaaacga agaaacuuuu gaaaugccag   120
cauuuaugau gaauaaugca ucagcuggag caaacuuuau guuugcuuaa uaacuacuag   180
uuuaguuaua guauuucacg aauuauagau auuuuaagcu uuauuuauaa ccguauuacc   240
caagcuuaau agaauauaug auugcaauaa auauauuuga aaucuaauug caaaugauau   300
uuaaccuuua guuaauuuua guuaaauauu uuaauuagaa aauuaacuaa acuguagaaa   360
guauguauua auauaucuug gacgcgaguu cgauucucgc caucuccacc a           411
```

```
<210> SEQ ID NO 111
<211> LENGTH: 381
<212> TYPE: RNA
<213> ORGANISM: Mycoplasma pirum

<400> SEQUENCE: 111
caugaaugau ggacccauag aggcaguggg guaugcccuu uauagcucaa gguuuaaauu    60
aaccgacaaa acugacgaaa acguugccgu ugauacaaau uuauuaauca accaacaagc   120
ucaauuuaac uacgcauuug cauaguauaa aaaaauaaau ugugcuacuc auuguaauua   180
gguuacuaaa uuacuuuguu uuauauaguc cuguaacuag uucagugau gucuauaaac   240 uagaaugaga uuuauagacu uauuguuggu cgguugugcc auagccuaaa ucaacaaaga   300
caauuuauuu augguacuaa acuguagauu cuaugaugaa auuauuugug gaaacggguu   360
cgauucccgc caucuccacc a                                            381
```

```
<210> SEQ ID NO 112
```

```
<211> LENGTH: 387
<212> TYPE: RNA
<213> ORGANISM: Mycoplasma pneumoniae

<400> SEQUENCE: 112
ggggauguag agguuuugac auaauguuga aaggaaaaca guugcagugg gguaugcccc      60
uuacagcucu agguauaaua accgacaaaa auaacgacga aguuuugua gauccaaugu     120 ugaucgcuaa ccaacaagca aguaucaacu acgcuuucgc uuagaacaua cuaaagcuac    180
acgaauugaa ucgccauagu ugguucgug ucacaguuua uggcucgggg uuaacugguu     240
caacuuaauc cuuaaauuau gaacuuaucg uuuacuugu ugucuauga ucuaaaguaa      300 gcgagacauu aaaacauaag acuaaacugu agaagcuguu uuaccaaucc uuuauggaaa    360
cggguucgau ucccgucauc uccacca                                        387

<210> SEQ ID NO 113
<211> LENGTH: 388
<212> TYPE: RNA
<213> ORGANISM: Mycoplasma genitalium

<400> SEQUENCE: 113
ggggauguuu uggguuugac auaaugcuga uagacaaaca guagcauugg gguaugcccc     60
uuacagcgcu agguucaaua accgacaaag aaauaacga aguguuggua gauccaaauu     120
ugaucauuaa ccaacaagca aguguuaacu uugcuuuugc auaaguagau acuaaagcua    180
cagcugguga auagcauag uuugcuagcu gucauaguuu augacucgag guuaaaucgu     240
ucaauuuaac cuuuaaaaau agaacuuguu guuccauga uuguuugug aucaauugga      300 aacaagacaa aauccacaa aacuaaaaug uagaagcugu uuguuguguc cuuuauggaa     360 acgguucga uuccgucau cuccacca                                         388

<210> SEQ ID NO 114
<211> LENGTH: 412
<212> TYPE: RNA
<213> ORGANISM: Ureaplasma urealyticum

<400> SEQUENCE: 114
ggggauguca cgguuucgac gugacacauu aauuuuaau ugcagugggg uuagccccuu      60
aucgcuuucg aggcauuuua aaugcagaaa auaaaaaauc uucugaagua gaauuaaacc    120
cagcguuuau ggcuucagcu acuaaugcaa acuacgcuuu ugcguacuaa uuaguuauua    180
guagaaacgu ucauuaacau aauuacuauu gguggguuuu ugggcuuauu uuacaauagu    240
uuuaaauuua aaauucuuau uguuguuuaa auuuaaauag auuuaacaaa uaguuaguua    300
auuuuaaauu uguuuuauua guuauuaacu acacauuuuu uaauaaaacu aaacuguaga    360
uauuauuaau uauguguugc ggaaaggggu ucgauucccc ucaucuccac ca            412

<210> SEQ ID NO 115
<211> LENGTH: 365
<212> TYPE: RNA
<213> ORGANISM: Mycoplasma salivarium

<400> SEQUENCE: 115
caggcauucg auucauuaug uugcaguggu uugcaaacca uaaggcacua ggcuuuuuua     60
aacgcaaaag accaaaaaac agaagaucaa gcaguugauc uagcauuuau gaauaauuca    120
caaaugcaau caaacucuagu uucgcuuag uaaaauuagu caauuauua ugggcucaa      180 cauaauaaau gguaguauga gcuuaauauc auaugauuuu aguuaauaug auaggauuug    240
```

```
uacuaaacu  auguuauaga  aauuuguaaa  uuauauauau  gacauaggaa  auuuaauuua    300
cuaaacugua  gaugcauaau  guugaagaug  ugggaccgg   gguucaacuc  ccgccagcuc    360
cacca                                                                     365

<210> SEQ ID NO 116
<211> LENGTH: 363
<212> TYPE: RNA
<213> ORGANISM: Clostridium innocuum

<400> SEQUENCE: 116
cggggauaug  ucgguacag   acugcagucg  agugguuacg  uaauaaccaa  uuaaauuuaa    60
acggaaaaac  uaaauuagcu  aaccucuuug  guggaaacca  gagaauggcu  uucgcugcuu    120
aauaaccgau  auagguucgc  agccgccucu  gcaugcuucu  uccuugacca  guggaugug     180 cgcguaagac  gcaagggaua  aggaaucugg  uuugccugag  aucagauuca  cgaaaauucu    240
ucaggcacau  ucaucagcgg  auguucauga  ccugcugaug  ucuuaaucuu  cauggacuaa    300
acuguagagg  ucuguacgug  gggcuguuuc  uggacaggag  uucgauuccc  gccgccucca    360
cca                                                                       363

<210> SEQ ID NO 117
<211> LENGTH: 359
<212> TYPE: RNA
<213> ORGANISM: Mycoplasma fermentans

<400> SEQUENCE: 117
caugcauugg  gugauacuaa  uaucaguagu  uggcagacu   auaaugcauc  uaggcuuuau    60
aaucgcagaa  gauaaaaaag  cagaagaagu  uaauauuucu  ucacuuauga  uugcacaaaa    120
aaugcaauca  caaucaaacc  uugcuuucgc  uuaguuaaaa  gugacaagug  guuuaaagu     180 ugacauuuuc  cuauauauuu  uaaaaucggu  uuuuaaggag  aacaggaguc  ugaaagggu     240 ccaaaaaucu  auauuguuug  cauuucggua  guauagauua  auuagaaaug  auaaacugua    300
aaaaguauug  guauugacuu  ggugugugga  cucggguuca  acucccgcca  gcuccacca    359

<210> SEQ ID NO 118
<211> LENGTH: 320
<212> TYPE: RNA
<213> ORGANISM: Acidobacterium capsulatum

<400> SEQUENCE: 118 cggggugac   ugcggcaaag  aggcaugccg  ggggguggcc  acccguaauc  gcucgcaaaa    60
caauacuugc  caacaacaau  cuggcacucg  cagcuuaauu  aaauaaguug  ccguccucug    120
aggcuucgcc  uguggggccga  ggcaggacgu  cauacagcag  gcugguuccu  ucggcugggu   180
cugggccgcg  gggaugagau  ccacggacua  gcauucugcg  uaucugucg   cuucuaagcg    240 cagagugcga  aaccuaaagg  aaugcgacug  agcauggagu  cucuuuucug  acaccaauuu    300
cggacgcggg  uucgauuccc                                                    320

<210> SEQ ID NO 119
<211> LENGTH: 319
<212> TYPE: RNA
<213> ORGANISM: Fusobacterium mortiferum

<400> SEQUENCE: 119
cggggUUaug  agguuauagg  uagcaugcca  ggaugaccgc  ugugagaggu  caacacaucg    60
```

```
uuuagaugga aacagaaauu acgcuuuagc ugcuuaauua gucagcucac cucugguuuc      120
ucucuucugu aggagaaucc aaccgaggug uuaccaauau acagauuacc uuuagugauu      180
ucucuaagcu caaagggaca uuuuagagaa uagcuucagu uagcccuguc ugcgggagug      240
auuguugcga aauaaaauag uagacuaagc auuguagaag ccuauggcgc ugguaguuuc      300
ggacacgggu ucaacuccc                                                   319

<210> SEQ ID NO 120
<211> LENGTH: 329
<212> TYPE: RNA
<213> ORGANISM: Fibrobacter succinogenes

<400> SEQUENCE: 120 cagggunuacc gaaguguuag uugcaagucg aggucucaga cgagggcuac ucguuaaaaa      60
gucugaaaaa aaauaagugc ugacgaaaac uacgcacucg cugccuaauu aacggcaacg     120
ccgggccuca uuccgcuccc aucgggugu acguccggac gcaauauggg auagggaagu      180
gucaugccug ggggcaucuc ccgagauuuu cuaggcuggu caaacuccgc gccgaccuuc     240
uugggcgugg auaagacgag aucuuaaauu cgaagggaac acuuguagga acguacaugg     300
acgugauuuu ggacaggggu ucaacuccc                                       329

<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121
acgcccuugu cucagacgag ggcacucguu aaaaagucug aaaagaauaa cugcagaacc      60
uguagcuaug gcugcuuaau uuaagggcaa cccuuggauc cgccuccauc ccgaagggggu    120 ggcauccgag ucgcaaaucg ggauaggaug gaucuuggca acgaggagua cauccgaaau     180
uugucgcugc uggcugaagc aucgccguuc cucuuugggc guggcaaggc aagauuaaau     240
ucagaggaua agcguguagu agcgagugag uagguguuuu uggacgcggg uucaagucccc    300

<210> SEQ ID NO 122
<211> LENGTH: 330
<212> TYPE: RNA
<213> ORGANISM: Pirellula staleyi

<400> SEQUENCE: 122
ccggauagcc ugaagcgaau acggcgugcc guggugauc agauggccac guaaaaagcu      60
gaucacaaac uuaacugccg agagcaaucu cgcacuugcu gccuaacuaa acguagcuu     120 ccgacugagg gcuuuagccg gagaggccca aaaguugguc accaaauccg gaccgcccug     180
ugccaugauc gaaacgcacg aggucaaaaa aguuucgauc uagugcaggg guagccagc     240 agcuaggcga caaacugugc aaaaaucaaa uuuucugcua cgcacguaga uguguucgug     300
aaaaugucuc gggacggggg uucaacuccc                                      330

<210> SEQ ID NO 123
<211> LENGTH: 329
<212> TYPE: RNA
<213> ORGANISM: Planctomyces maris

<400> SEQUENCE: 123
cugguucacc guauguuaag guggcggugc cgugguugau caguuggcca cguaaaaagc     60
```

```
ugaucacaau cuaauugcaa acaagcaauu uucaauggcu gcuuaauaaa agcaaccccg      120
gcuuaggaau cucugucuga ggaguccgac agcuggucac aaaaucagac ugguaucaga      180
ucaaugaccg cuccgucuga uacgagauuc gugguggacu gguuccaac aggcucuguu      240 uaucgugccc gaagaaacga gacucaaacg auaaaauaug caccguagag gcuuuagcug      300
aggguucaca ggacgcgggu ucaacuccc                                       329

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124
cagggaacca ggagguguga gaugcaugcc ggagacgcug uccgcuccgu uaucaagcag       60
cacaacaaaa uaauugcaaa caacaauuac uccuuagcag cguaagcagc uaacguucaa      120
ccucuccgga ccgccgggag gggauuuggg cgucgaaaca gcgcggacgc uccggauagg      180
acgcccauaa uauccggcua agaccauggg ucuggcucuc gcgggucuga uugucuucca      240
ccgcgcgggc cgcgaucaaa gacaacuaag cauguagguu cuugcauggc cuguucuuug      300
gacgcggguu cgauuccc                                                   318

<210> SEQ ID NO 125
<211> LENGTH: 407
<212> TYPE: RNA
<213> ORGANISM: Porphyromonas gingivalis

<400> SEQUENCE: 125
ggggcugacc ggcuuugaca gcgugaugaa gcgguaugua agcauguagu gcgugggugg       60
cuugcacuau aaucucagac aucaaaaguu uaauuggcga aaauaacuac gcucucgcug      120
cguaaucgaa gaauagauaga uuagacgcuu caucgccgcc aaaguggcag cgacgagaca     180
ucgcccgagc agcuuuuucc cgaaguagcu cgauggugcg gugcugacaa aucgggaacc     240
gcuacaggau gcuuccugcc uguggucaga ucgaacggaa gauaaggauc gugcauuggg     300
ucguuucagc cuccgcucgc ucacgaaaau ccaacugaa acuaaacaug uagaaagcau      360
auugauucca uguuuggacg agggucauu ucccuccagc uccacca                    407

<210> SEQ ID NO 126
<211> LENGTH: 379
<212> TYPE: RNA
<213> ORGANISM: Bacteroides thetaiotaomicron

<400> SEQUENCE: 126
cagcgggcag aaaugguagg uaagcaugca gugggucggu aauuccacu uaaaucucag        60 uuaucaaaac uuuaucuggc gaaacuaauu acgcucuugc ugcuuaaucg aaucacagua      120
gauuagcuua auccaggcac uaggugccca ggagagacau cacucggaag cuguugcucc     180
gaagcauucc gguucagugg ugcaguaaca ucggggauag ucagaagcgg ccucgcguuu     240
uugaugaaac uuuagaggau aaggcaggaa uugauggcuu gguucugcu ccugcacgaa      300 aauuuaggca aagauaagca guagaaagc uuaugauuuc cucguuugga cgagggucua      360
acuccgccca gcuccacca                                                  379

<210> SEQ ID NO 127
```

```
<211> LENGTH: 404
<212> TYPE: RNA
<213> ORGANISM: Chlorobium tepidum

<400> SEQUENCE: 127
ggggaugaca ggcuaucgac aggauaggug ugagaugucg uugcacuccg aguuucagca      60
uggacggacu cguuaaacaa gucuauguac caauagaugc agacgauuau ucguaugcaa     120
uggcugccug auuagcacaa guuaauucag aagccaucgu ccugcgguga augcgcuuac     180
ucugaagccg ccggauggca uaacccgcgc uugagccuac ggguucgcgc aaguaagcuc     240
cguacauuca ugcccgaggg ggugugcggg uaaccaaucg ggauaagggg acgaacgcug     300
cuggcggugu aaucggacca cgaaaaacca accaccagag augagugugg uaacugcauc     360
gagcagguc cuggacgcgg guucaagucc cgccaucucc acca                      404

<210> SEQ ID NO 128
<211> LENGTH: 372
<212> TYPE: RNA
<213> ORGANISM: Chlorobium limicola

<400> SEQUENCE: 128
caggauacgu gugagaugu cguugcacucc gaguuucagc augga cggac ucguuaaaca     60
agucuaugua ccauuagaug cagacgauua uucguaugca auggcugccu gauuagcaca    120
aguuaacuca gacgccaucg uccugcggug aaugcgcuua cucugaagcc gccggauggc    180
auaacccgcg cuugagccua cggguucgcg caaguaagcu ccguacauuc augcccgagg    240
ggcugugcgg guaauuucuc gggauaaggg gacgaacgcu gcuggcggug uaaucggccc    300
acgaaaaccc aaucaccaga gaugagugug gugacugcau cgagcagugu uuggacgcg    360
gguucaacuc cc                                                        372

<210> SEQ ID NO 129
<211> LENGTH: 420
<212> TYPE: RNA
<213> ORGANISM: Chlamydia trachomatis

<400> SEQUENCE: 129 gggggguguaa agguuucgac uuagaaauga agcguuaauu gcaugcggag ggcguuggcu     60
ggccuccuaa aaagccgaca aaacaauaaa ugccgaaccu aaggcugaau gcgaaauuau    120
cagcuucgcu gaucucgaag aucuaagagu agcugcuuaa uuagcaaagu uguuaccuaa    180
auacggguga cccgguguuc gcgagcucca ccagagguuu cgaaacaccg ucaugu auc    240
ugguuagaac uuagguccuu uaauucucga ggaaaugagu uugaaauuua augagagucg    300
uuagucucua uaggguuuc uagcugagga gacauaacgu auaguaccua ggaacuaagc    360
auguagaggu uagcggggag uuuacuaagg acgagaguuc gacucucucc accuccacca    420

<210> SEQ ID NO 130
<211> LENGTH: 421
<212> TYPE: RNA
<213> ORGANISM: Chlamydia mousep*

<400> SEQUENCE: 130 gggggguguaa agguuucgac uuagaaauga agcguuaauu gcaugcggag ggcguuggcu     60
ggccuccuaa aaagccgaca aaacaauaaa ugccgaaccu aaggcugaau gcgaaauuau    120
cagcuucgcu gaucuuaaug aucuaagagu ugcugcuuaa uuagcaaagu uguuaccuaa    180
guacuggua cccgguguuc gcgagcucca ccagagguuu cgaaacgcc gucauuuauc     240
```

| | |
|---|---|
| ugguuagaau uagggccuuu uaacucucaa gggaacuaau uugaauuuua augagagucg | 300 |
| uuggucucua uagagguuuc uagcugagga gauauaacgu aaaauauucu agaaacuaag | 360 |
| cauguagagg uuagcgggga guuuacuaag gacgagaguu cgaaucucuc caccuccacc | 420 |
| a | 421 |

<210> SEQ ID NO 131
<211> LENGTH: 426
<212> TYPE: RNA
<213> ORGANISM: Chlamydia pneumoniae

<400> SEQUENCE: 131

| | |
|---|---|
| ggggguguau agguuucgac uugaaaauga aguguuaauu gcaugcggag ggcguuggcu | 60 |
| ggccuccuaa aaagccaaca aaacaauaaa ugccgaaccu aaggcugaau gcgaaauuau | 120 |
| uagcuuguuu gacucaguag aggaaagacu agcugcuuaa uuagcaaaag uuguuagcua | 180 |
| gauaaucucu agguaacccg guaucugcga gcuccaccag aggcuugcaa aauaccguca | 240 |
| uuuaucuggu uggaacuuac uuucucuaau ucucaaggaa guucguucga gauuuugag | 300 |
| agucauuggc ugcuauagag gcuucuagcu aagggagucc aauguaaaca auucuagaag | 360 |
| auaagcaugu agagguuagc agggaguuug ucaaggacga gaguucgagu cucuccaccu | 420 |
| ccacca | 426 |

<210> SEQ ID NO 132
<211> LENGTH: 328
<212> TYPE: RNA
<213> ORGANISM: Micrococcus luteus

<400> SEQUENCE: 132

| | |
|---|---|
| cggugugugu cgcgucggga aagcgggcc gaggaugcag agucaucucg ucaaacgcuc | 60 |
| ucugcaaacc aauaagugcc gaauccaagc gcacugacuu cgcucucgcu gccugaucag | 120 |
| ugaucgaguc cgucacccg aggucgcugu cgccucggau cguggcguca gcuagauagc | 180 |
| cacugggcgu caccucgcc ggggucgug acgccgacau caauccggcu gggucccgggu | 240 |
| uggccgcccg ucugcgggac ggccaggacc gagcaacacc cacagcagac ugcgcccgga | 300 |
| gaagaccugg caacaccuca ucggacgc | 328 |

<210> SEQ ID NO 133
<211> LENGTH: 368
<212> TYPE: RNA
<213> ORGANISM: Mycobacterium leprae

<400> SEQUENCE: 133

| | |
|---|---|
| ggggcugaaa gguuucgacu ucgcgcaucg aaucaaggga agcgugccgg ugcaggcaag | 60 |
| agaccaccgu aagcgucguu gcagcaauau aagcgccgau ucauaugagc gcgacuaugc | 120 |
| ucucgcugcc uaagcgaugg cuagucuguc agaccgggaa cgcccucguc ccggagccug | 180 |
| gcaucagcua gagggaucua ccgauggguu cggucgcggg acucgucggg acaccaaccg | 240 |
| cgacugggau cgucauccug gcuaguucgc gugaucagga gauccgagua gaggcauagc | 300 |
| gaacuacgca cggagaagcc uugagggaaa ugccguagga cccgggguucg auucccggca | 360 |
| gcuccacc | 368 |

<210> SEQ ID NO 134
<211> LENGTH: 360
<212> TYPE: RNA

-continued

<213> ORGANISM: Mycobacterium tuberculosis

<400> SEQUENCE: 134

```
ggggcugaac gguuucgacu ucgcgcaucg aaucaaggga agcgugccgg ugcaggcaag     60
agaccaccgu aagcgucguu gcgaccaaau aagcgccgau ucacaucagc gcgacuacgc    120
ucucgcugcc uaagcgacgg cuagucuguc agaccgggaa cgcccucggc ccggacccug    180
gcaucagcua ccaccgauga guccggucgc gggacuccuc gggacaacca cagcgacugg    240
gaucgucauc ucggcuaguu cgcgugaccg ggagauccga gcagaggcau agcgaacugc    300
gcacggagaa gccuugaggg aaugccguag gacccggguu cgauucccgg cagcuccacc    360
```

<210> SEQ ID NO 135
<211> LENGTH: 373
<212> TYPE: RNA
<213> ORGANISM: Mycobacterium avium

<400> SEQUENCE: 135

```
ggggcugaaa gguuucgacu ucgcgcaucg aaucaaggga agcgugccgg ugcaggcaac     60
ugaccaccgu aagcgucguu gcagauagau aagcgccgau ucacaucagc gcgacuacgc    120
ucucgcugcc uaagcgacag cuagucgagg gaucgucagc ccgggaacgc ccucgacccg    180
gagccuggcg ucagcuagag ggauccaccg augaguucgg ucgcgggacu caucgggaca    240
ccaacagcga cugggaucgu cauccuggcu uguucgcgug accaggagau ccgaguagag    300
gcauagcgaa cugcgcacgg agaagccuug agggaaugcc guaggacccg gguucgauuc    360
ccggcagcuc cac                                                        373
```

<210> SEQ ID NO 136
<211> LENGTH: 331
<212> TYPE: RNA
<213> ORGANISM: Corynebacterium xerosis

<400> SEQUENCE: 136

```
cuucguacau ugagccaggg gaagcgugcc ggugaaggcu ggagaccacc gcaagcgucg     60
cagcaaccaa uuaagcgccg agaacucuca gcgcgacuac gcccucgcug ccuaagcagc    120
gaccgcgugu cugucagacc ggguaggccu cugauccgga cccuggcauc guuuaguggg    180
gcucgcucgc cgacuugguc gcaagggucg gcggggacac ucacuugcga cugggcccgu    240
cauccgguca uguucgacug aaccggaggg ccgagcagag accacgcgcg aacugcgcac    300
ggagaagccc uggcgaggug acggaggacc c                                    331
```

<210> SEQ ID NO 137
<211> LENGTH: 354
<212> TYPE: RNA
<213> ORGANISM: Treponema pallidum

<400> SEQUENCE: 137

```
ggggaugacu agguuucgac uagggaugug ggguguugcg cugcaggugg agugucgauc     60
uccugauucg gcgccuuuau aacugccaau ucugacaguu ucgacuacgc gcucgccgcg    120
uaaucgcggg ccuguguuug cgcugcucug agcgaacaua ucggcccgac gccaaacgga    180
gcuugcucuu acguugugca cggcggacgu agggggacuu uugucugugc uaagacucug    240
gcgcgugcgg ugcaggccua gcagaguccg acaaacgcag uacgcaccgc uaaaccugua    300
ggcgcgcagc acucgcucuu uaggacgggg guucgauucc ccccaucucc acca          354
```

-continued

<210> SEQ ID NO 138
<211> LENGTH: 362
<212> TYPE: RNA
<213> ORGANISM: Borrelia burgdorferi

<400> SEQUENCE: 138
ggggauguuu uggauuugac ugaaaauguu aauauuguaa guugcaggca gagggaaucu 60
cuuaaaacuu cuaaaauaaa ugcaaaaaau aauaacuuua caagcucaaa ucuuguaaug 120
gcugcuuaag uuagcagagg guuuuguuga auuuggcuuu gagguucacu uauacucuuu 180
ucgacaucaa agcuugcuua aaaauguuuu caaguugauu uuuagggacu uuuauacuug 240
agagcaauuu ggugguuugc uaguauuucc aaaccauauu gcuuaauaaa auacuagaua 300
agcuuguaga agcuuauagu auuauuuuua ggacgcgggu ucaauucccg ccaucuccac 360
ca 362

<210> SEQ ID NO 139
<211> LENGTH: 364
<212> TYPE: RNA
<213> ORGANISM: Borrelia garinii

<400> SEQUENCE: 139
ggggcugauu cuggauucga cugaaaaugc gaauauugua aguugcaggc agagggaauc 60
ucuuaaaacu ucuaaaauaa augcaaaaaa uaauaacuuu acaagcucaa accuuguaau 120
ggcugcuuaa guuagcaggg aguuucguug aauuuggcuu ugagguucac uuauacucuu 180
uucgauaucg aagcuugcuu aaaaauguuu ucaaguuaau uuuuagggac uuuuguacuu 240
gagagcaauu uggcgguuug cuaguauuuc caaaccauau ugcuuaagua aaaugcuaga 300
uaagcuugua gaagcuuaua auauuguuuu uaggacgcgg guucaauucc cgccaucucc 360
acca 364

<210> SEQ ID NO 140
<211> LENGTH: 363
<212> TYPE: RNA
<213> ORGANISM: Borrelia afzelii

<400> SEQUENCE: 140
ggggcugauu cuggauucga cugaaaaugc uaauauugua aguugcaagc agagggaauc 60
ucuuaaaacu ucuaaaauaa augcaaaaaa uaauaacuuu acaaguucaa accuuguaau 120
ggcugcuuaa guuagcagag aguuuuguug aauuuggcuu ugagauucac uuauacucuu 180
uuagacaucg aagcuugcuu aaaaauguuu ucaaguugau uuuuagggac uuuuauacuu 240
gagagcaauu uggcgguuug cuaguauuuc caaaccauau ugcuuaguaa aauacuagau 300
aagcuuguag aagcuuauag uauuguuuuu aggacgcggg uucaauuccc gccaucucca 360
cca 363

<210> SEQ ID NO 141
<211> LENGTH: 363
<212> TYPE: RNA
<213> ORGANISM: Borrelia crocidurae

<400> SEQUENCE: 141
ggggcugauu cuggauucga cuaagaacuu uaguagcaua aauggcaagc agagugaauc 60
ucuuaaaacu ucuuuaauaa augcaaaaaa uaauaacuuu acaaguucag aucuuguaau 120
ggcugcuuaa uuuagcagag aguuuuguug gauuuugcuu ugagguucaa cuuauacucu 180

```
uuaagacauc aaaguaugcc uaaaaauguu ucaaguugau uuuuagggac cuuuaaacuu    240
gagaguaauu uguggguuug cuuguuuucc aagccuuauu gcuuuuucua aaaauuagcu    300
aagcuuguag auauuuauga uauuauuuuu uggacgcggg uucaauuccc gccaucucca    360
cca                                                                 363

<210> SEQ ID NO 142
<211> LENGTH: 365
<212> TYPE: RNA
<213> ORGANISM: Borrelia hermsii

<400> SEQUENCE: 142
ggggcugauu cuggauucga cuaaaaacuu uaguagcaua aauugcaagc agagggaauc    60
ucuuaaaacu ucuuuaauaa augcaagaaa uauaacuuu acaaguucaa aucuuguaau    120
ggcugcuuaa auuagcagag aguucugcug gauuugcuu ugagguucag cuuauacucu    180
uuuaagacau caaagcuugc uuaaaaauau uucaaguuga uuuuuaggga cuuuuaaauu    240
ugagaguaau uuggcgguuu gcuaguuuuu ccaaaccuua uuacuuaaag aaaacacuag    300
cuaagcuugu agauauuuau gauuauuauu uuaggacgcg gguucaauuc ccgccaucuc    360
cacca                                                               365

<210> SEQ ID NO 143
<211> LENGTH: 330
<212> TYPE: RNA
<213> ORGANISM: Alcaligenes faecalis

<400> SEQUENCE: 143
cgggggucaa gaagcagcac agggcguguc gagcaccagu acgcucguaa auccacugga    60
aaacuauaaa cgccaacgac gagcguuucg cucuagccgc uuaaggcugg gccacugcac    120
uaauuugucu uugggguuagg uagggcaacc uacagcagug uuauuuacaa agaaucgaau    180
cggucugcgc cacgaagucc gguucuaaaa cuuaguggau cgccaaggaa aggccuguca    240
auuggcauag uccaagguua aaacuuaaaa uuaauugacu acacauguag aacugucugu    300
ggacggcuug cggacggggg uucgauuccc                                     330

<210> SEQ ID NO 144
<211> LENGTH: 340
<212> TYPE: RNA
<213> ORGANISM: Alcaligenes eutrophus

<400> SEQUENCE: 144
cguggguuac aaagcagugg agggcauacc gaggacccgu caccucguua aucaauggga    60
augcaauaac ugcuaacgac gaacguuacg cacuggccgc uuaauugcgg ccguccucgc    120
acuggcucgc ugacgggcua ggucgcaag accacgcgag gucauuuacg ucagauaagc    180
uccggaaggg ucacgaagcc ggggacgaaa accuagugac ucgccgucgu agagcguguu    240
cguccgcgau gcgccgguua aaucaaauga cagaacuaag uauguagaac ucucugugga    300
gggcuuacgg acgcggguuc gauucccgcc ggcuccacca                         340

<210> SEQ ID NO 145
<211> LENGTH: 326
<212> TYPE: RNA
<213> ORGANISM: Ralstonia pickettii

<400> SEQUENCE: 145
cggggguugc gaagcagcgg agggcauacc gaggacccgu caccucguua aucaauggga    60
```

```
augcaauaac ugcuaacgac gaacguuacg cacuggcagc cuaagggccg ccguccucgc      120
acuggcucgc ugacgggcua ggucgcaag accagcgagg ucauuuacgu cagauaagcu       180
uuaggugagu cacgggccua gagacgaaaa cuuagugaau cgccgucgua gagcguguuc      240
guccgcgaug cggcgguuaa aucaaaugac agaacuaagu auguagaacu cucuguggag      300
ggcuugcgga cgcgggcuucg auuccc                                          326
```

<210> SEQ ID NO 146
<211> LENGTH: 363
<212> TYPE: RNA
<213> ORGANISM: Neisseria gonorrhoeae

<400> SEQUENCE: 146

```
gggggcgacc uugguuucga cggggguugc gaagcagaug cgggcauacc ggggucucag      60
auccccguaa aacacugaau ucaaauaguc gcaaacgacg aaacuuacgc uuuagccgcu      120
uaaggcuagc cguugcagca gucggucaau gggcugugug ugaaagcca ccgcaacguc      180 aucuuacauu gacugguuuc cagccggguu acuggcagg aaauaagacu uaagguaacu      240
gguuuccaaa aggccuguug gucggcauga uggaaauaag auuucaaaau agacacaacu      300
aaguauguag aacgcuuugu agaggacuuu cggacggggg uucgauuccc cccgccucca     360
cca                                                                    363
```

<210> SEQ ID NO 147
<211> LENGTH: 363
<212> TYPE: RNA
<213> ORGANISM: Neisseria meningitidis

<400> SEQUENCE: 147

```
gggggcgacc uugguuucga cggggguugc gaagcagaug cgggcauacc ggggucucag      60
auccccguaa aacacugaau ucaaauaguc gcaaacgacg aaacuuacgc uuuagccgcu      120
uaaggcuagc cguugcagca gucggucaau gggcugugug gcgaaagcca ccgcaacguc      180
aucuuacauu gacugguuuc cugccggguu auuuggcagg aaaugagauu uaagguaacu      240
gguuuccaaa aggccuguug gucggcauga uggaaauaag auuucaaaau agacacaacu      300
aaguauguag aacgcuuugu agaggacuuu cggacggggg uucgauuccc cccgccucca     360
cca                                                                    363
```

<210> SEQ ID NO 148
<211> LENGTH: 333
<212> TYPE: RNA
<213> ORGANISM: Chromobacterium violaceum

<400> SEQUENCE: 148

```
cgggggguugc gaagcagaug agggcauacc gggauuucag ucaccccgua aaacgcugaa      60
uuuauauagu cgcaaacgac gaaacuuacg cucuggcagc cuaacggccg gccagacacu      120
acaacgguuc gcagauggc cggggcguc aaacccgu agucacucu acaucugcu           180 agugcuguuc cggguuacuu gguucagugc gaaauaauag guaacucgcc aaaguccagc      240
cuguccgucg gcguggcaga gguuaaauucc aaaugacacg acuaaguaug uagaacucac     300
uguagaggac uuucggacgc gggguucaacu ccc                                  333
```

<210> SEQ ID NO 149
<211> LENGTH: 330
<212> TYPE: RNA

<213> ORGANISM: Nitrosomonas cryotolerans

<400> SEQUENCE: 149

```
cguggguugc aaagcagcgc agggcauacc gaggaccaga auaccucgua aauacaucug    60
gaaaaaaaua gucgcaaacg acgaaaacua cgcuuuagcc gcuuaauacg gcuagccucu   120
gcaccgaugg gccuuaacgu cgggucuggc aacagacagc agagucauua gcaaggaucg   180
cguucuguag ggucacuuua cagaacguua aacaauaggu gacucgccug ccaucagccc   240
gccagcuggc gguugucagg uuaaauuaaa gagcauggcu aaguauguag aacugucugu   300
agaggacuug cggacgcggg uucaacuccc                                    330
```

<210> SEQ ID NO 150
<211> LENGTH: 331
<212> TYPE: RNA
<213> ORGANISM: Methylobacillus glycogenes

<400> SEQUENCE: 150

```
cgggggguugc aaagcagcgc agggcauacc gaggccuagu caccucguaa auaaacuaga    60
acaaguauag ucgcaaacga cgaaacuuac gcucuagccg cuuaaucccg gcuggacgcu   120
gcaccgaagg gccucucggu cgguggggu aacccacagc agcgucauua agagaggauc   180
gugcgauauu ggguuacuua auaucguauu aaauccaagg uaacucgccu gcuguuugcu   240
ugcucguugg ugagcaucag guuaaaucaa acaacacagc uaaguaugua aacugucug   300
uggagggcuu gcggacgggg guucgauucc c                                  331
```

<210> SEQ ID NO 151
<211> LENGTH: 375
<212> TYPE: RNA
<213> ORGANISM: Pseudomonas testosteroni

<400> SEQUENCE: 151

```
ggggccgauu cuggauucga cguggguucg ggaccggugc ggugcauguc gagcuugagu    60
gacgcucgua aaucuccauu caaaaaacua acugcaaacg acgaacguuu cgcacucgcc   120
gcuuaauccg gugagccuug caacagcacg cuagugggcu gggcaagggg guagcaauac   180
cucccggcug caagggaauu ucauuagcu ggcuggauac cgggcuucuu gguauuuggc   240
gagauuuuag gaagcuggcu acccaagcag cgugugccug cggggguugg guggcgagau   300
uuaaaacaga gcacuaaaca uguagaucug uccggcgaag gcuuacggac gcggguucaa   360
uucccgccgg cucca                                                    375
```

<210> SEQ ID NO 152
<211> LENGTH: 353
<212> TYPE: RNA
<213> ORGANISM: Variovorax paradoxus

<400> SEQUENCE: 152

```
cgugggguucg gagucgcagc ggggcauguc gagcugaaug cgcucguaaa acagauucaa    60
acaaacuaac ugcaaacgac gaacguuucg cacucgcugu uaauugcca gugagccuug   120
caacaguugg ccgaugggcu gggcaagggg gucuggagca auccugaccu cccggcugca   180
aggauaacua cauggcugg cuccgauccg gguaccuugg gucggggcga gaaaauaggg   240
uacuggcguc cgguuuagcg ugugacucg cgacuccgga agcgagacuc aaaacagauc   300
acuaaacaug uagaacugcg cgaugaaggc uugcggacgg ggguucaacu ccc          353
```

<210> SEQ ID NO 153
<211> LENGTH: 345
<212> TYPE: RNA
<213> ORGANISM: Hydrogenophaga palleroni

<400> SEQUENCE: 153

| | | | | | |
|---|---|---|---|---|---|
| cguggguucg | gacgcgcagc | agggcauguc | gagguucugu | caccucguaa aucagcagaa | 60 |
| aaaaaccaac | ugcaaacgac | gaacguuucg | cacucgccgc | uuaaacaccg gugagccuug | 120 |
| caacagcagg | ccgaugggcu | gggcaagggg | gucgcaagac | cucccggcug caagguaauu | 180 |
| uacaucggcu | gguucugcgu | cgggcaccuu | ggcgcaggau | gagauucaag gaugcuggcu | 240 |
| ucccguuuag | cgugccacug | cgcgacucgg | gcggcgagac | ccaaaucaga cggcuacaca | 300 |
| uguagaacug | cucgaaaaag | gcuugcggac | ggggguucaa | cuccc | 345 |

<210> SEQ ID NO 154
<211> LENGTH: 387
<212> TYPE: RNA
<213> ORGANISM: Bordetella pertussis

<400> SEQUENCE: 154

| | | | | | |
|---|---|---|---|---|---|
| ggggccgauc | cggauucgac | gugggucaug | aaacagcuca | gggcaugccg agcaccagua | 60 |
| agcucguuaa | uccacuggaa | cacuacaaac | gccaacgacg | agcgucucgc ucucgccgcu | 120 |
| uaagcgguga | gccgcugcac | ugaucugucc | uugggucagg | cggggaagg caacuuccca | 180 |
| ggggcaacc | ccgaaccgca | gcagcgacau | ucacaaggaa | ucggccaccg cuggggucac | 240 |
| acggcguugg | uuuaaauuac | gugaaucgcc | cuggccggc | ccgucgaucg gcuaagucca | 300 |
| ggguuaaauc | caauagauc | gacuaagcau | uagaaacugg | uugcggaggg cuugcggacg | 360 |
| ggggguucaau | uccccccggc | uccacca | | | 387 |

<210> SEQ ID NO 155
<211> LENGTH: 323
<212> TYPE: RNA
<213> ORGANISM: Legionella pneumophila

<400> SEQUENCE: 155

| | | | | | |
|---|---|---|---|---|---|
| cgugggugc | aaaaccggaa | gugcaugccg | agaaggagau | cucucguaaa uaagacucaa | 60 |
| uuaaauauaa | augcaaacga | ugaaaacuuu | gcuggugggg | aagcuaucgc ugccuaauaa | 120 |
| gcacuuuagu | uaaaccauca | cuguguacug | gccaauaaac | ccaguauccc guucgaccga | 180 |
| gcccgcuuau | cgguaucgaa | ucaacgguca | uaagagauaa | gcuagcgucc uaaucuaucc | 240 |
| cggguuaugg | cgcgaaacuc | agggaaucgc | uguguaucau | ccugcccguc ggaggagcca | 300 |
| caguuaaauu | caaaagacaa | ggc | | | 323 |

<210> SEQ ID NO 156
<211> LENGTH: 315
<212> TYPE: RNA
<213> ORGANISM: Chromatium vinosum

<400> SEQUENCE: 156

| | | | | | |
|---|---|---|---|---|---|
| cguggguucgc | gaaaccuaag | gugcaugccg | aggugcgguu | gaccucguaa aacccuccgc | 60 |
| aaacuuauag | uugccaacga | cgacaacuac | gcucucgcug | cuuaaucccca gcggccucu | 120 |
| gaccgucacu | ugccuguggg | cggcggauuc | cagggguaac | cucacacagg aucguguga | 180 |
| cgggagccg | gaccugaucc | acuaaaaccu | aacggaaucg | ccgacugauc gcccugcccu | 240 |
| ucgggcggca | gaaggcuaaa | aacaauagag | ugggcuaagc | auguaggacc gagggcagag | 300 |

```
ggcuugcgga cgcgg                                                315
```

<210> SEQ ID NO 157
<211> LENGTH: 318
<212> TYPE: RNA
<213> ORGANISM: Dichelobacter nodosus

<400> SEQUENCE: 157

```
cucgaggugc augucgagaa ugagagaauc ucguuaaaua cuucaaaac uuauaguugc   60 aaacgacgac aacuacgcuu uagcggcuua auucccgcuu ucgcuuaccu agauuugucu  120 gugguuuac cguaagcgac auuaacacag aaucgcuggu uaacgcgucc gcuguuaauc   180
gguuaaauua agcggaaucg cuuguaaaau gccugagcgu uggcuguuua ugaguuaaac  240
cuaauuaacu gcucuaaaca uguaguacca aaguuaagg auucgcggac gggguucaa    300 aucccccgc cuccacca                                                318
```

<210> SEQ ID NO 158
<211> LENGTH: 354
<212> TYPE: RNA
<213> ORGANISM: Pseudomonas aeruginosa

<400> SEQUENCE: 158

```
ggggccgauu aggauucgac gccgguaaca aaacuugagg ggcaugccga gcugguagca   60
gaacucguaa auucgcugcu gcaaacuuau aguugccaac gacgacaacu acgcucuagc  120
ugcuuaaugc ggcuagacag ucgcuagggg augccguaa acccgaaacg acugucagau  180
agaacaggau cgccgccaag uucgcuguag acguaacggc uaaaacucau acagcucgcu  240
ccaagcaccc ugccacucgg gcggcgcgga guuaacucag uagagcuggc uaagcaugua  300
gaaccgauag cggagagcug gcggacgggg guucaaaucc ccccggcucc acca        354
```

<210> SEQ ID NO 159
<211> LENGTH: 350
<212> TYPE: RNA
<213> ORGANISM: Pseudomonas fluorescens

<400> SEQUENCE: 159

```
cgccgguugc gaaccuuuag gugcaugccg aguugguaac agaacucgua aauccacugu   60
ugcaacuuuc uuaguugcca augacgaaac cuacggggaa uacgcucucg cugcguaagc  120
agccuuagcc cuuccuccu gguaccuucg gguccagcaa ucaucagggg augucuguaa   180
acccaaagug auugucauau agaacagaau cgccgugcag uacguuguggg acgaagcggc  240 uaaaacuuac acaacucgcc caaagcaccc ugcccgucgg gucgcugagg guuaacuuaa  300
uagacacggc uacgcaugua guaccgacag cagaguacug gcggacgggg              350
```

<210> SEQ ID NO 160
<211> LENGTH: 323
<212> TYPE: RNA
<213> ORGANISM: Marinobacter hydrocarbonoclasticus

<400> SEQUENCE: 160

```
cgccggugac gaacccuugg gugcaugccg agauggcagc gaaucucgua aauccaaagc   60
ugcaacguaa uagcgcaaa cgacgaaaac uacgcacugg cggcguaagc cguccagud   120 guccuggcug aggcgccuau aacucaguag caacaucccca ggacgucauc gcuuauaggc  180
ugcuccguuc accagagcuc acuggguguuc ggcuaagauu aaaagagcucg ccucuugcac  240 ccugaccuuc ggguucgcuug agguuaaauc aauagaagga cacuaagcau guagaccuca  300
```

```
aggccuagug cuggcggacg cgg                                               323

<210> SEQ ID NO 161
<211> LENGTH: 355
<212> TYPE: RNA
<213> ORGANISM: Shewanella putrefaciens

<400> SEQUENCE: 161
gggggcgauu cuggauucga caggauucac gaaacccugg gagcaugccg aggggcgguu        60
ggccucguaa aaagccgcaa aguuauaguu gcaaacgacg auaacuacgc ucuagccgcu       120
uaaugccgcu agccaucuac cacacgcuuu gcacaugggc aguggauuug auggucaucu       180
cacaucgugc uagcgaggga acccugucug ggggugaacc gcgaaacagu accggacuca       240
ccguguggga uccugucuuu cggaguucaa acgguuaaac aauagaaaga cuaagcaugu       300
agcgccuugg auguagguuu ucggacgcg gguucaaguc cgccgccuc cacca              355

<210> SEQ ID NO 162
<211> LENGTH: 314
<212> TYPE: RNA
<213> ORGANISM: Pseudoalteromonas haloplanktis

<400> SEQUENCE: 162
cggaauucaa gaagcccgag gugcaugucg aggugcgguu ugccucguaa aaagccgca        60 auuuaaagua aucgcaaacg acgauaacua cucucuagca gcuuaggcug gcuagcgcuc      120
cuuccaugua uucuugugga cuggauuuug gagugucacc cuaacaccug aucgcgacgg      180
aaacccuggc cggguugaa gcguuaaaac uaagcggccu cgccuuuauc uaccguguuu       240
guccgggauu uaaagguuaa uuaaaugaca auacuaaaca guaguaccg acggucgagg       300 cuuuucggac gggg                                                         314

<210> SEQ ID NO 163
<211> LENGTH: 316
<212> TYPE: RNA
<213> ORGANISM: Aeromonas salmonicida

<400> SEQUENCE: 163
caagauucac gaacccaag gugcaugccg aggugcggua ggccucguua acaaaccgca        60 aaaaauagu cgcaaacgac gaaaacuacg cacuagcagc uuaauaaccu gcauagagcc      120
cuucuacccu agcuugccug uguccuaggg aaucggaagg ucauccuuca caggaucgug      180 uggaagccu gcucggggcg gaagcauuaa aaccaaucga gcuagucaau cguggcgug       240 ucucuccgca gcgggguggc gaauguaaag agugacuaag caugaguac cgaggaugua      300 guaauuuugg acgggg                                                       316

<210> SEQ ID NO 164
<211> LENGTH: 363
<212> TYPE: RNA
<213> ORGANISM: Salmonella typhimurium

<400> SEQUENCE: 164
ggggcugauu cuggauucga cgggauuugc gaaacccaag gugcaugccg aggggcgguu      60
ggccucguaa aaagccgcaa aaaauagc gcaaacgacg aaaccuacgc uuuagcagcu       120
uaauaaccug cuuagagccc ucucucccua gccuccgcuc uuaggacggg gaucaagaga      180
ggucaaaccc aaaagagauc gcgcggaugc ccugccuggg guugaagcgu uaaaacgaau      240
```

```
caggcuaguc ugguaguggc guguccgucc gcaggugcca ggcgaaugua aagacugacu    300
aagcauguag uaccgaggau guaggaauuu cggacgcggg uucaacuccc gccagcucca    360
cca                                                                  363

<210> SEQ ID NO 165
<211> LENGTH: 363
<212> TYPE: RNA
<213> ORGANISM: Escherichia coli

<400> SEQUENCE: 165
ggggcugauu cuggauucga cgggauuugc gaaacccaag gugcaugccg aggggcgguu     60
ggccucguaa aaagccgcaa aaaauagucg caaacgacga aaacuacgcu uuagcagcuu    120
aauaaccugc uuagagcccu cucucccuag ccuccgcucu uaggacgggg aucaagagag    180
gucaaaccca aaagagaucg cguggaagcc cugccugggg uugaagcguu aaaacuuaau    240
caggcuaguu uguuaugugc guguccgucc gcagcggca agcgaaugua aagacugacu    300
aagcauguag uaccgaggau guaggaauuu cggacgcggg uucaacuccc gccagcucca    360
cca                                                                  363

<210> SEQ ID NO 166
<211> LENGTH: 364
<212> TYPE: RNA
<213> ORGANISM: Yersinia pestis

<400> SEQUENCE: 166
ggggcugauu cuggauucga cgggauucgc gaaacccaag gugcaugccg aggugcggug     60
gccucguaaa aaccgcaaa aaaauaguu gcaaacgacg aaaacuacgc acuagcagcu    120
uaauaaccug cuuagagccc ucucucccua gccuccgcuc uuaggacggg gaucaagaga    180
ggucaaaccu aaaagagcuc guguggaaac cuugccuggg guggaagcau aaaacuaau    240 caggauaguu ugucaguagc guguccaucc gcagcuggcc ggcgaaugua augauuggac    300
uaagcaugua gugccgacgg uguaguaauu ucggacgggg guucaaauuc ccccagcucc    360
acca                                                                 364

<210> SEQ ID NO 167
<211> LENGTH: 367
<212> TYPE: RNA
<213> ORGANISM: Vibrio cholerae

<400> SEQUENCE: 167
ggggcugauu caggauucga cgggaauuuu gcagucugag gugcaugccg aggugcggua     60
ggccucguua acaaaccgca aaaaaauagu cgcaaacgac gaaaacuacg cacuagcagc    120
uuaauacccu gcucagagcc cuuccucccu agcuuccgcu uguaagacgg ggaaaucagg    180
aaggucaaac caaaucaagc uggcguggau uccccaccu gagggaugaa gcgcgagauc    240
uaauucaggu uagccauucg uuagcguguc gguucgcagg cggugugaa auuaaagauc    300 gacuaagcau guguaccaa agaugaaugg uuuucggacg ggguucaac uccccccagc    360 uccacca                                                              367

<210> SEQ ID NO 168
<211> LENGTH: 366
<212> TYPE: RNA
<213> ORGANISM: Haemophilus influenzae

<400> SEQUENCE: 168
```

```
ggggcugauu cuggauucga cgggauuagc gaagcccaag gugcacgucg aggugcggua    60
ggccucguaa auaaaccgca aaaaaauacu cgcaaacgac gaacaauacg cuuuagcagc   120
uuaauaaccu gcauuuagcc uucgcgcucc agcuuccgcu cguaagacgg ggauaacgcg   180
gagucaaacc aaaacgagau cguguggaag ccaccguuug aggaucgaag cacuaaauug   240
aaucaaacua gcuuaaguuu agcgugucug uccgcaugcu uaagugaaau uaaagacgag   300
acuaaacgug uaguacugaa gguagaguaa uuucggacgg ggguucaacu cccccagcu   360 ccacca                                                              366

<210> SEQ ID NO 169
<211> LENGTH: 366
<212> TYPE: RNA
<213> ORGANISM: Haemophilus actinomycetemcomitans

<400> SEQUENCE: 169
ggggcugauu cuggauucga cgggauuagc gaagcccgaa gugcacgucg aggugcggua    60
ggccucguaa auaaaccgca aaaaaauagu cgcaaacgac gaacaauacg cuuuagcagc   120
uuaauaaccu gccuuuagcc uucgcuccc agcuuccgcu cguaagacgg ggauaaagcg   180
gagucaaacc aaaacgagau cguguggaag ccaccguuug aggaucgaag cauuaaauua   240
aaucaaagua gcuuaauugu cgcgguccg ucagcaggau uaagugaauu uaaagaccgg   300
acuaaacgug uagugcuaac ggcagaggaa uuucggacgg ggguucaacu cccccagcu   360 ccacca                                                              366

<210> SEQ ID NO 170
<211> LENGTH: 354
<212> TYPE: RNA
<213> ORGANISM: Desulfovibrio desulfuricans

<400> SEQUENCE: 170
cggggacgug gaagccguag cggcaggucg aggcgccgcu ggccucguaa aaagcggcac    60
aaaaguaauu gccaacaacg auuacgacua cgcuuacgcu gccuauaac agcgaggcaa   120 ugaccguuua acggucgcgc cgaucagggc caugccugau aacccugauu cacuuaucag   180
gcuggcgaaa accggcucuc gccggggguuu uucgcgagga guuuaccggc gggauuccug   240
cguugugccu ggucaggggc caacagcgcg gugaaauaca uacuugaccu aaaccuguag   300
augcuucgug uggaauguuc ucggacgggg guucaaaucc ccccggcucc acca         354

<210> SEQ ID NO 171
<211> LENGTH: 366
<212> TYPE: RNA
<213> ORGANISM: Myxococcus xanthus

<400> SEQUENCE: 171
gggggcggaa aggauucgac gggggcauug aaguucgaga cgcgugccga gcuugucagg    60
uagcucguaa auucaacccg gcaaagacac aaaagccaac gacaacguug agcucgcgcu   120
ggcugccuaa aaacagccca uagugcgcgg ucccccgcc cucggccugu gggguuggga   180
cagaccguca uaaugcaggc uggcugccga gggugccugg acccgaggug gcagaucuu   240 cccaggaccg gcucugagua ucccguccgu gggagccuca gggacguagc aaaucgcgga   300
cuacgcacgu agggucgaag agcggacggc uuucggacgc gggucgauu cccgccgccu   360 ccacca                                                              366
```

<210> SEQ ID NO 172
<211> LENGTH: 346
<212> TYPE: RNA
<213> ORGANISM: Bdellovibrio bacteriovirus

<400> SEQUENCE: 172
gggggcggaa aggauucgac ggggggugcug aagcauaagg agcauaccgg ggcggaugag    60
gaccucguua aaaacgucca cuuuguaauu ggcaacgauu acgcacuugc agcuuaauua   120
agcagcacga ucaaccuugu ggugguuccg cacuuggauu gaucgucauu uagggaccuc   180
ggcguguugg guuuucucca gcagacaugc uuaaauuuac uggggagag gucuuaggga    240 uuuugucugu ggaagcccga ggaccaaucu aaaacacuga cuaaguaugu agcgccuuau   300
cguggaucau uugcggacgg ggguucgauu cccgccgccu ccacca                  346

<210> SEQ ID NO 173
<211> LENGTH: 386
<212> TYPE: RNA
<213> ORGANISM: Helicobacter pylori

<400> SEQUENCE: 173
ggggcugacu uggauuucga cagauuucuu gucgcacaga uagcaugcca agcgcugcuu    60
guaaaacagc aacaaaaaua acuguaaaca acacagauua cgcuccagcu acgcuaaag   120 cugcgugagu uaaucuccuu uuggagcugg acugauuaga auuucuagcg uuuuaaucgc   180
uccauaaccu uaagcuagac gcuuuuaaaa ggugguucgc cuuuuaaacu aagaaacaag   240
aacucuugaa acuaucucaa gguuuuagaa aguuggacca gagcuaguuu uaaggcuaaa   300
aaaccaacca auuuucuaag cauuguagaa guuuguguuu agggcaagau uuuuggacug   360
ggguucgauu ccccacagcu ccacca                                        386

<210> SEQ ID NO 174
<211> LENGTH: 359
<212> TYPE: RNA
<213> ORGANISM: Campylobacter jejuni

<400> SEQUENCE: 174
gggagcgacu uggcuucgac aggaguaagu cugcuuagau ggcaugucgc uuugggcaaa    60
gcguaaaaag cccaaauaaa auuaaacgca aacaacguua aauucgcucc ugcuuacgcu   120
aaagcugcgu aaguucaguu gagccugaaa uuuaagucau acuaucuagc uuaauuuucg   180
gucauuuuug auaguguagc cuugcguuug acaagcguug aggugaaaua aagucuuagc   240
cuugcuuuug aguuuuggaa gaugagcgaa guagggugaa guagucaucu uugcuaagca   300
uguagagguc uuugugggau uauuuuugga caggggucg auucccccucg cuuccacca   359

<210> SEQ ID NO 175
<211> LENGTH: 355
<212> TYPE: RNA
<213> ORGANISM: Sulfurospirillum deleyianum

<400> SEQUENCE: 175
caggaguagu uuuagcuuau ggcugcaugu cgggagugag ggucuuccgu uacacaaccu    60
ucaaacaaua acugcuaaca acaguaacua ucguccugcu uacgcgcuag cugcguaagu   120
uuaacaaaua auggacugcu cuccccuuug augcuaucuu aggaggucuu ggagaguauc   180

-continued

```
auagauuuga uagcuauauu acaugaacgc cuuuacaugu aaugaaguua aaggcucguu      240
uucguaguuu ucugauuguu guacgaagca aaauuaaaca cuaucaacaa uaucuaagca      300
uguagacguc auagguggcu auuuuuggac uggggguucaa cucccgccag cucca          355
```

EUBACTERIAL TMRNA SEQUENCES AND USES THEREOF

CROSS-REFERENCE TO RELATED APPLICATIONS

The present application is a divisional application of U.S. patent application Ser. No. 09/958,206 filed 20 Feb. 2002, now U.S. Pat. No. 7,115,366, which in turn is a national stage filing under 35 U.S.C. 371 of International patent application No. PCT/US00/08988 filed on 6 Apr. 2000, which in turn is related to and claims priority under 35 U.S.C. 119(e) to U.S. provisional patent application Ser. No. 60/128,058 filed on 7 Apr. 1999. Each of these applications is incorporated herein by reference.

This application was made with Government support under Grant No. GM 48152, funded by the National Institutes of Health, Bethesda, Md. The Government has certain rights in this invention.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in *E. coli*, both as tRNA and as mRNA (for a review, see Muto et al., 1998). These ≈360±10% nucleotide RNAs are charged with alanine at their 3'-ends (Komine et al., 1994; Ushida et al., 1994) and also have a short reading frame coding for 9 to 27 amino acids depending on the bacterial species. *E. coli* tmRNA mediates recycling of ribosomes stalled at the end of terminator less mRNAs, via a trans-translation process (Tu et al., 1995; Keiler et al., 1996; Himeno et al., 1997). In *E. coli*, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. *E. coli* tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 3A, 3B and 3C show the sequence alignment, structural domains and structural features for the tmRNA of several species of *Firmicutes*. The tmRNA sequences are set forth in SEQ ID NOs:67-87.

FIGS. 4A and 4B show the sequence alignment, structural domains and structural features for the tmRNA of several species of *Thermophiles*. The tmRNA sequences are set forth in SEQ ID NOs:88-99.

FIGS. 7A-1, 7A-2, 7B, 7C and 7D show the sequence alignment, structural domains and structural features for the tmRNA of several species of *Mesophiles* (7A-1, 7A-2, 7C, 7D) and environmental sludge (7B). The tmRNA sequences of the *Mesophiles* are set forth in SEQ ID NOs:118-123 and 125-128, and the tmRNA sequence of the environmental sludge is set forth in SEQ ID NO:124.

FIGS. 8A and 8B show the sequence alignment, structural domains and structural features for the tmRNA of several species of *Actinobacteries* (8A) and *Spirochaetes* (8B). The tmRNA sequences of the *Actinobacteries* are set forth in SEQ ID NOs:132-136, and the tmRNA sequences of the *Spirochaetes* are set forth in SEQ ID NOs:137-142.

FIGS. 9A and 9B show the sequence alignment, structural domains and structural features for the tmRNA of several species of *Pourpres* beta. The tmRNA sequences are set forth in SEQ ID NOs:143-154.

FIGS. 10A, 10B and 10C show the sequence alignment, structural domains and structural features for the tmRNA of several species of *Pourpres* gamma. The tmRNA sequences are set forth in SEQ ID NOs:155-169.

DETAILED DESCRIPTION OF THE INVENTION

Figure 1B:
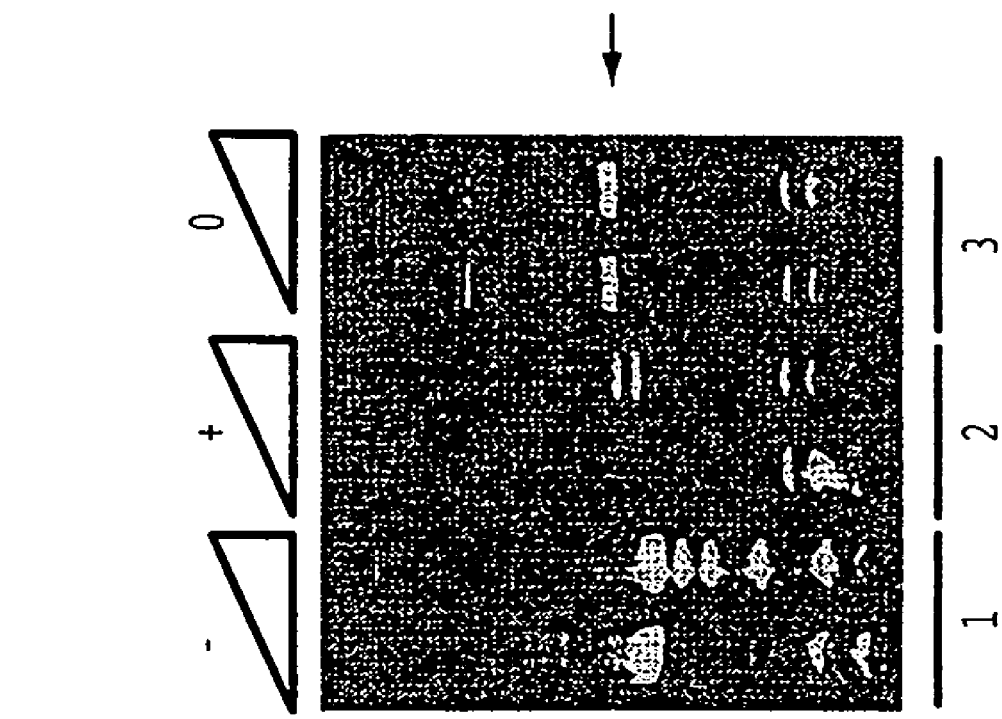
FIGS. 1A-1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of Thermus aquaticus (1). B; Varying the magnesium concentration to amplify tmDNA genes from Thermus aquaticus (1), negative effect of increasing the magnesium concentration), *Acholeplasma laidlawii* (2), positive effect of increasing the magnesium concentration, the upper band is the tmDNA gene) and from *Mycoplasma salivarium* (3), no discernible effect of magnesium ions in that concentration range). The arrows point toward the 4 novel tmDNA genes that have been sequenced.

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1-58, below. The alignment of tmRNA sequences is shown in FIGS. 3A-11B, which also show the structural domains and structural features of the tmRNA. The present invention also includes the tmRNA sequences set forth in these figures to the extent they differ from the sequences set forth in Tables 1-58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 basepairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonorrheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteries or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (Remington's, 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extaction of Genomic DNA

Bacterial genomic DNAs were prepared from ≈10 mg freeze-dried cells provided from ATCC (American Type Culture Collection, Virginia, USA). Cell pellets were resuspended in 750 µL of lysis buffer (50 mM Tris (pH 8.0), 50 mM EDTA and 20% sucrose). 150 µL of a 10 mg/mL solution of lysozyme was mixed and let stand at room temperature for 15 min. 150 µL of 1% SDS was added and let stand at room temperature for 15 minutes. Four to five phenol/chloroform extractions were performed, until the sample was clear and there was no interphase. Two to five µL of a 10 mg/mL solution of RNase DNase-free was added and incubated at room temperature for 30 minutes. After a phenol/chloroform extraction of the enzyme, the genomic DNA was precipitated with 1/10 volume of 3M NaOAc (pH 5.5) and 1 volume isopropanol, and stored at −20° C. for 2 hours. After centrifugation, the genomic DNAs were washed With 70% ethanol, vacuum-dried and diluted in sterile water to a final concentration of 10 ng/µL.

2. Primer Sets for PCR Reactions

The following primer sets were used during the PCR:

```
primer set A (based on E. coli tmRNA termini):
5'-GGG GCT GAT TCT GGA TTC GAC-3'                    (SEQ ID NO:1)
```

-continued and
5'-TGG AGC TGG CGG GAG TTG AAC-3'; (SEQ ID NO:2)

primer set B (based on *T neapolitana* tmRNA termini):
5'-GGG GGC GGA AAG GAT TCG ACG -3' (SEQ ID NO:3)
and
5'-TGG AGG CGG CGG GAA TCG AAC-3'; (SEQ ID NO:4)

primer set C (based on *M pneumoniae* tmRNA termini):
5'-GGG GAT GTC ATG GTT TTG ACA -3' (SEQ ID NO:5)
and
5'-TGG AGA TGG CGG GAA TCG AAC-3'; (SEQ ID NO:6)
and primer set D (based on *C. tepidum* tmRNA termini):
5'-GGG GAT GAC AGG CTA TCG ACA-3' (SEQ ID NO:7)
and
5'-TGG AGA TGG CGG GAC TTG AAC-3'. (SEQ ID NO:8)

3. PCR Reaction

Sequences of tmRNA genes were obtained by polymerase chain reaction (PCR) in 25 µL using 40 ng of genomic DNA per reaction. The following general scheme was utilized for all of the sequences:

(a) 94° C. to 96° C. for 4 min. (first denaturation of genomic DNAs, done only once); then (b) 35 to 40 PCR cycles with 2.5 to 5 Units of Taq DNA polymerase in a 25 µL reaction volume, according to the following scheme (40 ng of genomic DNAs/PCR reaction):

1. denature at 94° to −96° C. for 25 to 30 sec;
2. anneal at 44° to 55° C. for 20 to 30 sec; and
3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 µl solution containing 10 mM Tris-HCl buffer (pH 8.1). The following day, the PCR amplified tmDNAs were ethanol precipitated, washed in 70% ETOH, vacuum dried and the DNA pellets were dissolved in 18 µl of RNase-DNase free sterile water.

5. DNA Sequencing

Six µL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

*Acidobacterium*:

Primer Set B; Annealing temp. during PCR: 53° C. for 20 sec; $Mg^{2+}$ conc.: 4.5 mM.

*Coprothermobacter*:

Primer Set B; Annealing temp. during PCR: 55° C. for 30 sec; $Mg^{2+}$ conc.: 5.5 mM.

*Cytophagales*:

Primer Set A; Annealing temp. during PCR: 46° C. for 30 sec; $Mg^{2+}$ conc.: 4.5 mM.

*Dictyoglomus*:

Primer set B; Annealing temp. during PCR: 55° C. for 30 sec; $Mg^{2+}$ conc.: 4.5 mM.

Environmental Samples:

Sludge DNA

Primer set C; Annealing temp. during PCR: 51° C. for 20 sec; $Mg^{2+}$ conc.: 13.5 mM.

Rumenal fluid DNA

Primer set D; Annealing temp. during PCR: 50° C. for 30 sec; $Mg^{2+}$ conc.: 9.5 mM.

*Fibrobacter*:

Primer set A; Annealing temp. during PCR: 51° C.; $Mg^{2+}$ conc.: 3.5 mM.

*Firmicutes*:

*Fusobacteria*:

Primer set A; Annealing temp. during PCR: 52° C.; $Mg^{2+}$ conc.: 5.5 mM.

High G-C:

Primer set A; Annealing temp. during PCR: 50-55° C.; $Mg^{2+}$ conc.: 4.5 mM.

Low G-C:

Primer sets A or B; Annealing temp. during PCR: 52° C.; $Mg^{2+}$ conc.: 5.5 to 7.5 mM.

*Mycoplasmes*:

Primer set A; Annealing temp. during PCR: 52° C.; $Mg^{2+}$ conc.: 3.5 to 5.5 mM.

Green Non-Sulfur:

Primer sets A or B; Annealing temp. during PCR: 46 to 52° C.; $Mg^{2+}$ conc.: 4.5 mM.

Green Sulfer:

Primer set A; Annealing temp. during PCR: 46° C.; $Mg^{2+}$ conc.: 4.5 mM.

*Planctomycetales*:

Primer set A; Annealing temp. during PCR: 48 to 52° C.; $Mg^{2+}$ conc.: 7.5 mM.

*Proteobacteria:*
   beta:
      Primer sets A and/or B; Annealing temp. during PCR: 50° C. for 25 sec; Mg$^{2+}$ conc.: 3.5 mM.

Delta:
      Primer set B; Annealing temp. during PCR: 55° C.; Mg$^{2+}$ conc.: 3.5 to 4.5 mM.

Epsilon:
      Primer set A; Annealing temp. during PCR: 46° C. for 30 sec; Mg$^{2+}$ conc.: 3.5 mM.

Gamma:
      Primer set A; Annealing temp. during PCR: 44° C. for 30 sec; Mg$^{2+}$ conc.: 5.5 mM.

*Spirochetes:*
   Primer set A; Annealing temp. during PCR: 52° C.; Mg$^{2+}$ conc.: 4.5 mM.

*Thermodesulfo bacterium:*
   Primer set B; Annealing temp. during PCR: 55° C.; Mg$^{2+}$ conc.: 5.5 mM.

*Thermotogales:*
   Primer set B; Annealing temp. during PCR: 46° C.; Mg$^{2+}$ conc.: 7.5 mM.

*Deinococcales:*
   Primer set B; Annealing temp. during PCR: 52° C.; Mg$^{2+}$ conc.: 3.5 mM.

*Verrucomicrobia:*
   Primer set A; Annealing temp. during PCR: 53° C. for 25 sec; Mg$^{2+}$ conc.: 3.5 mM.

Example 3

Amplification of Eubacterial tmDNA

Figure 1A:
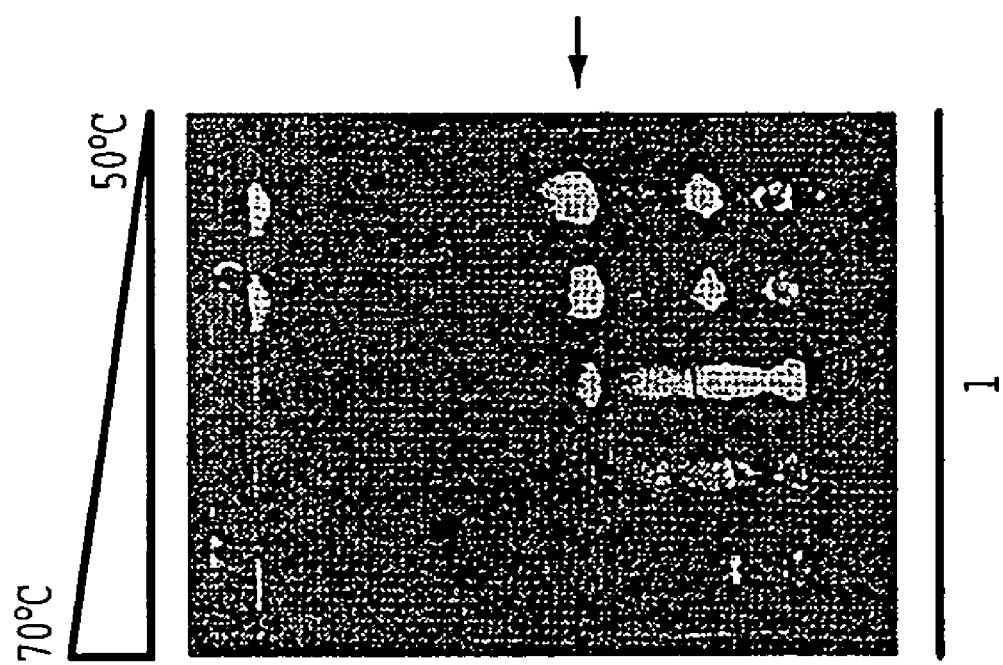

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

Figure 2:
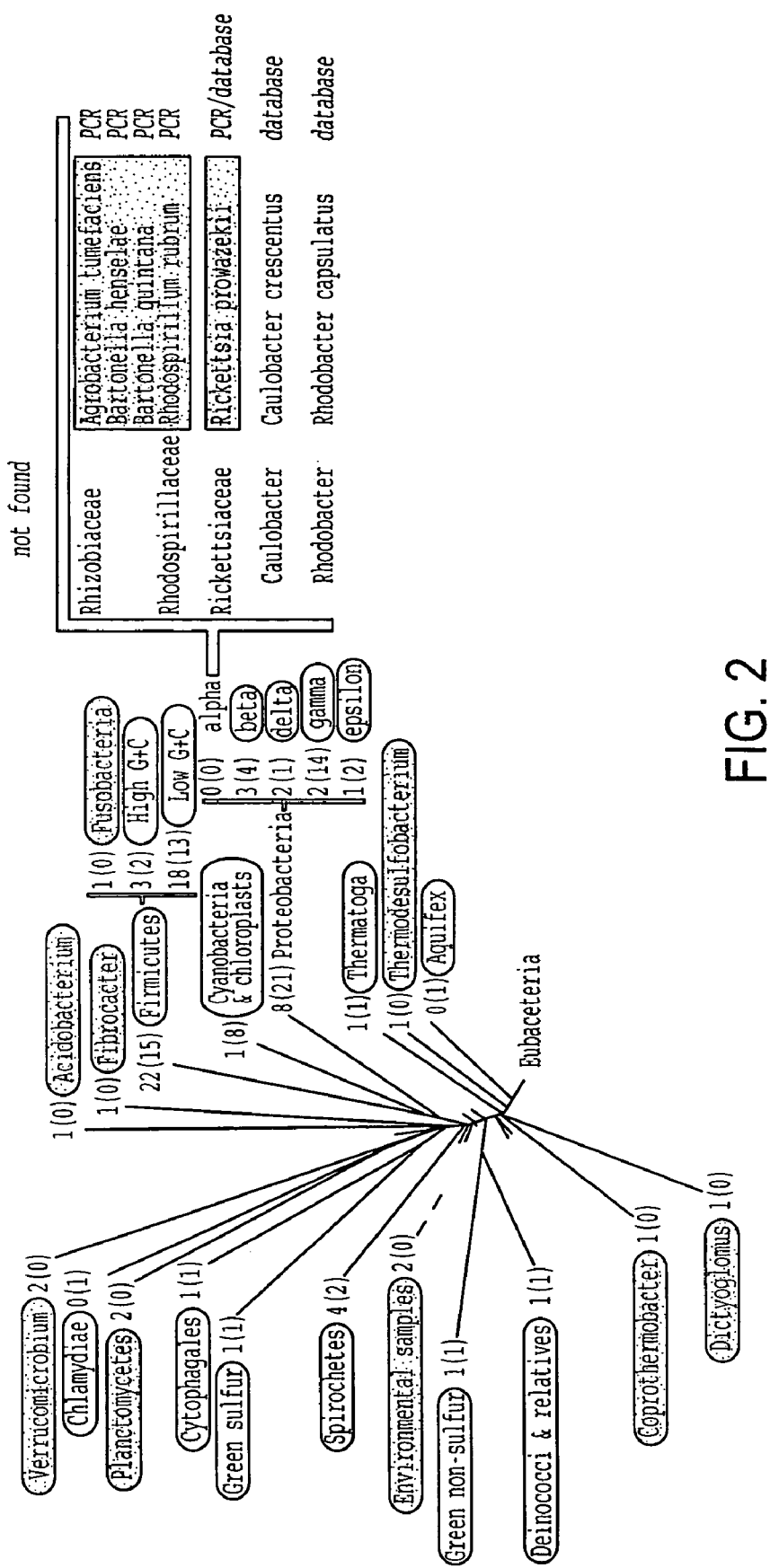
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 4A:
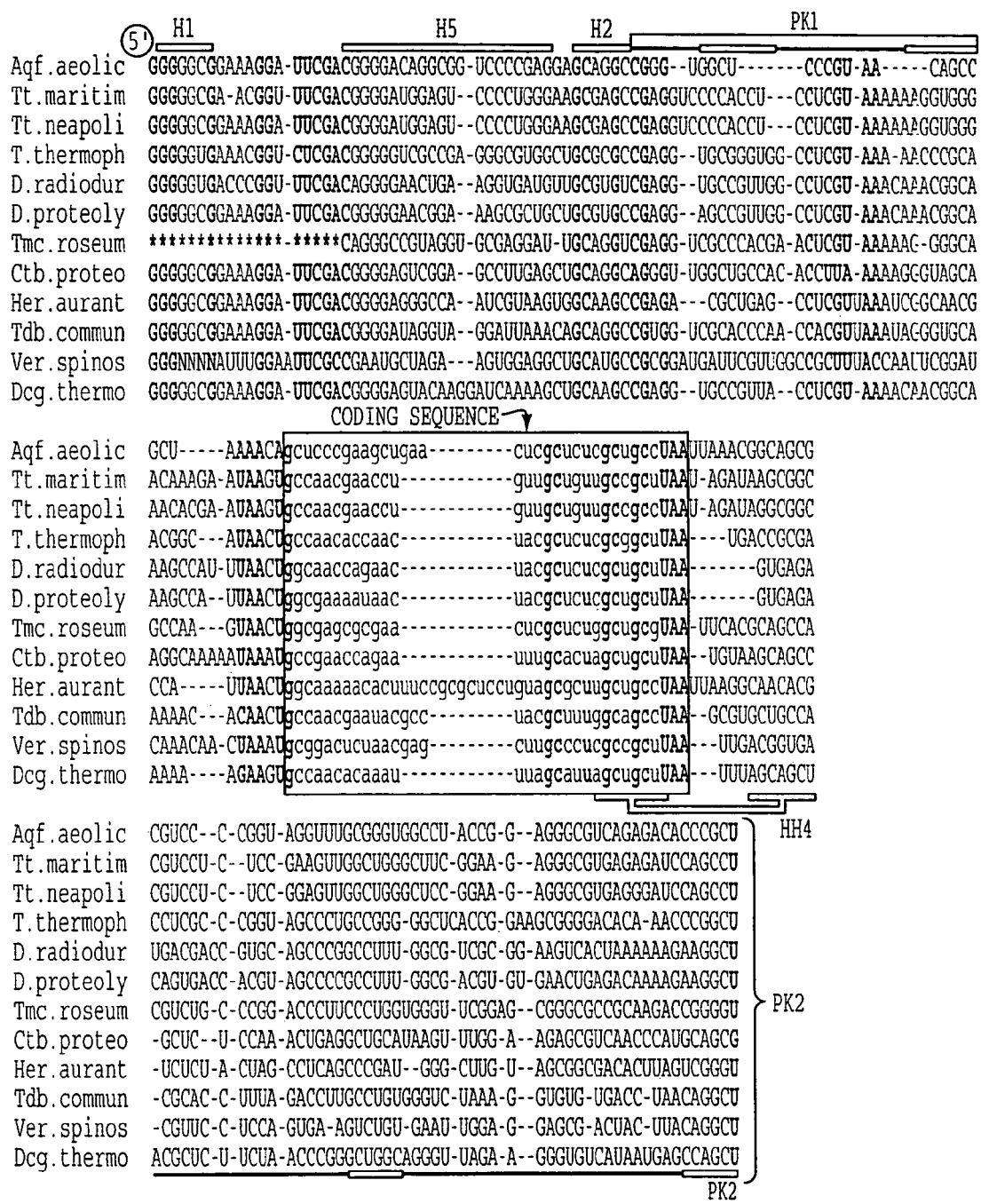
Figure 5A:
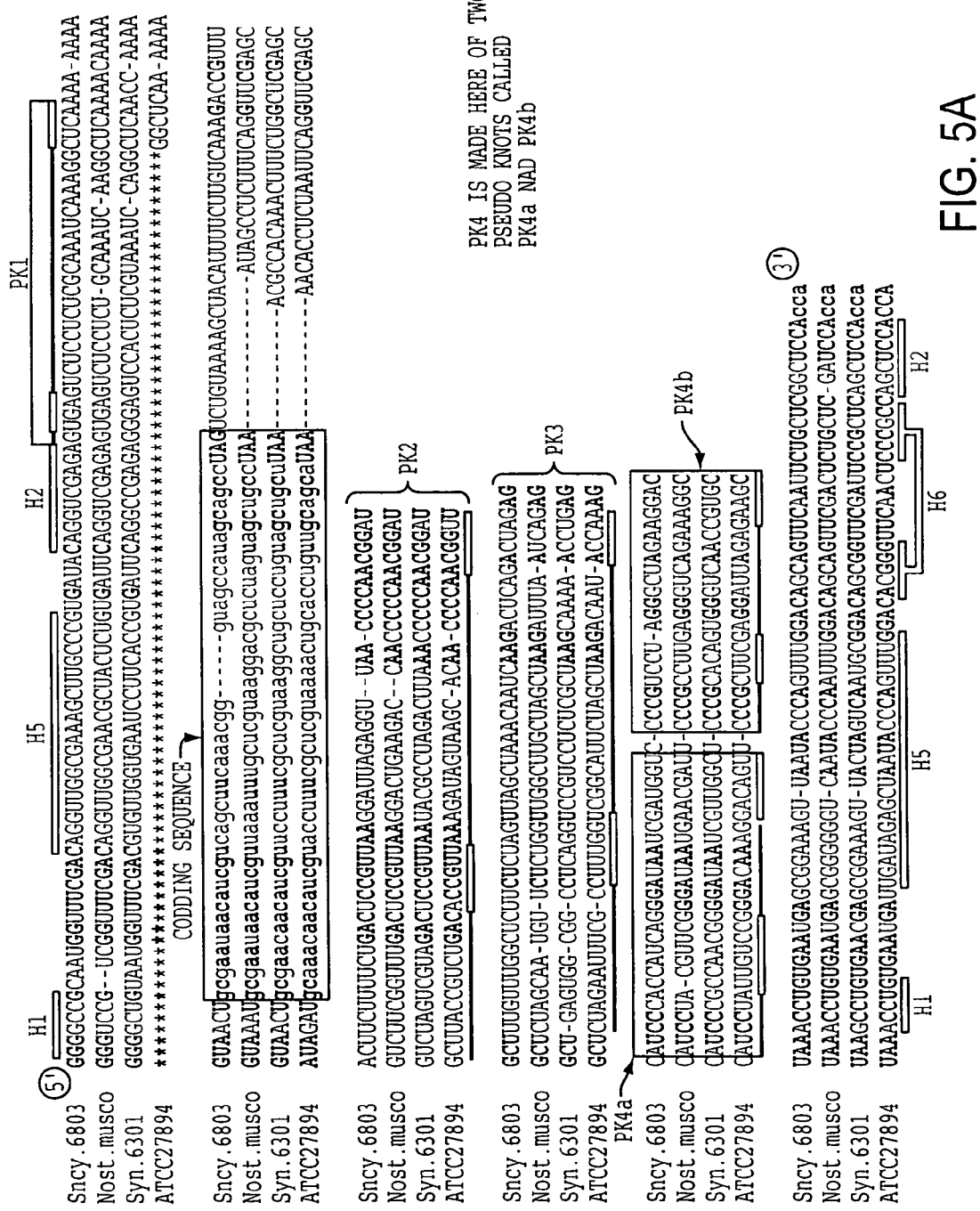
FIGS. 5A and 5B show the sequence alignment, structural domains and structural features for the tmRNA of several species of *Cyanobacteries* (5A) and chloroplasts (5B). The tmRNA sequences of the *Cyanobacteries* are set forth in SEQ ID NOs:100-103, and the tmRNA sequences of the chloroplasts are set forth in SEQ ID NOs:104-108.
Figure 5B:
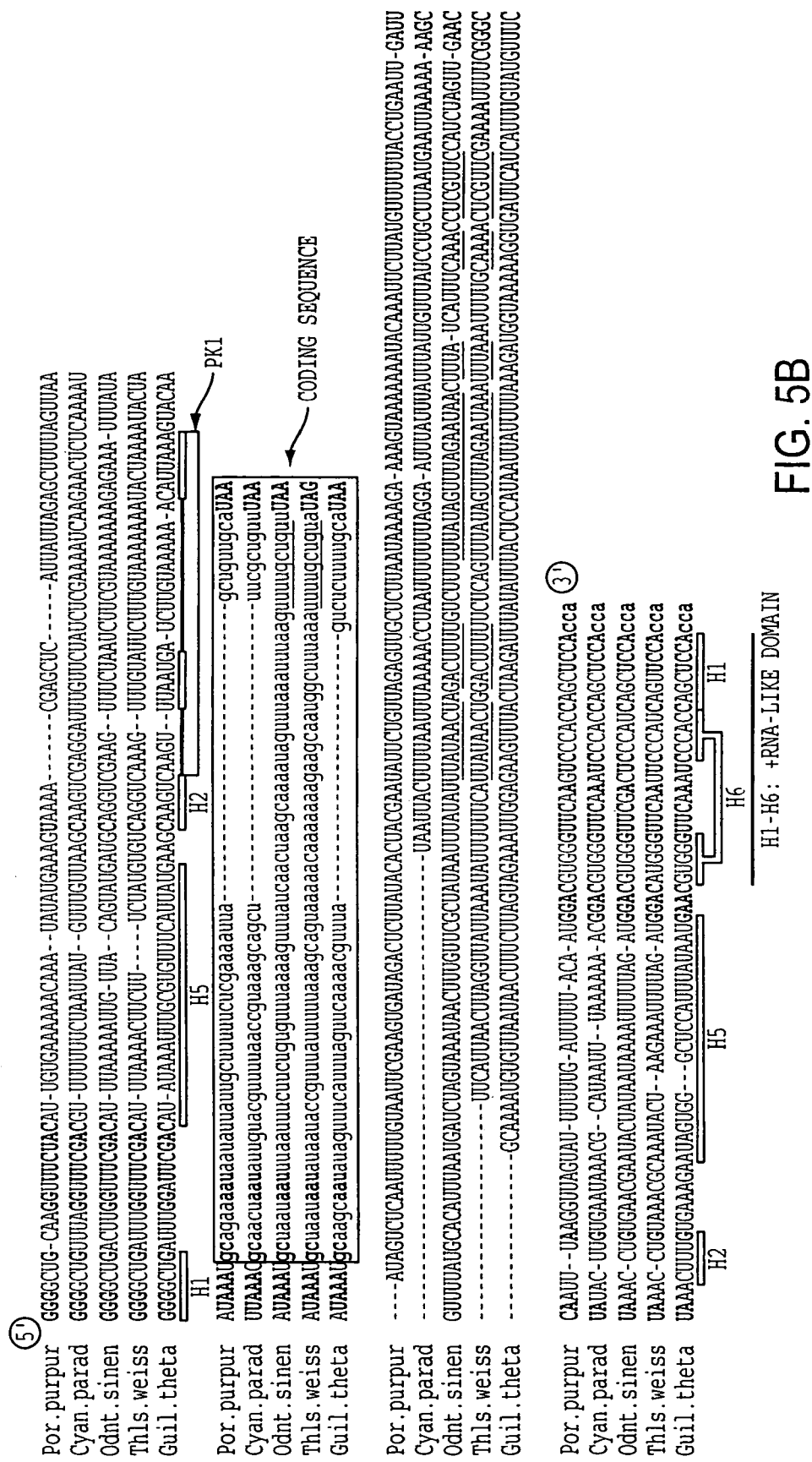
Figure 6A:
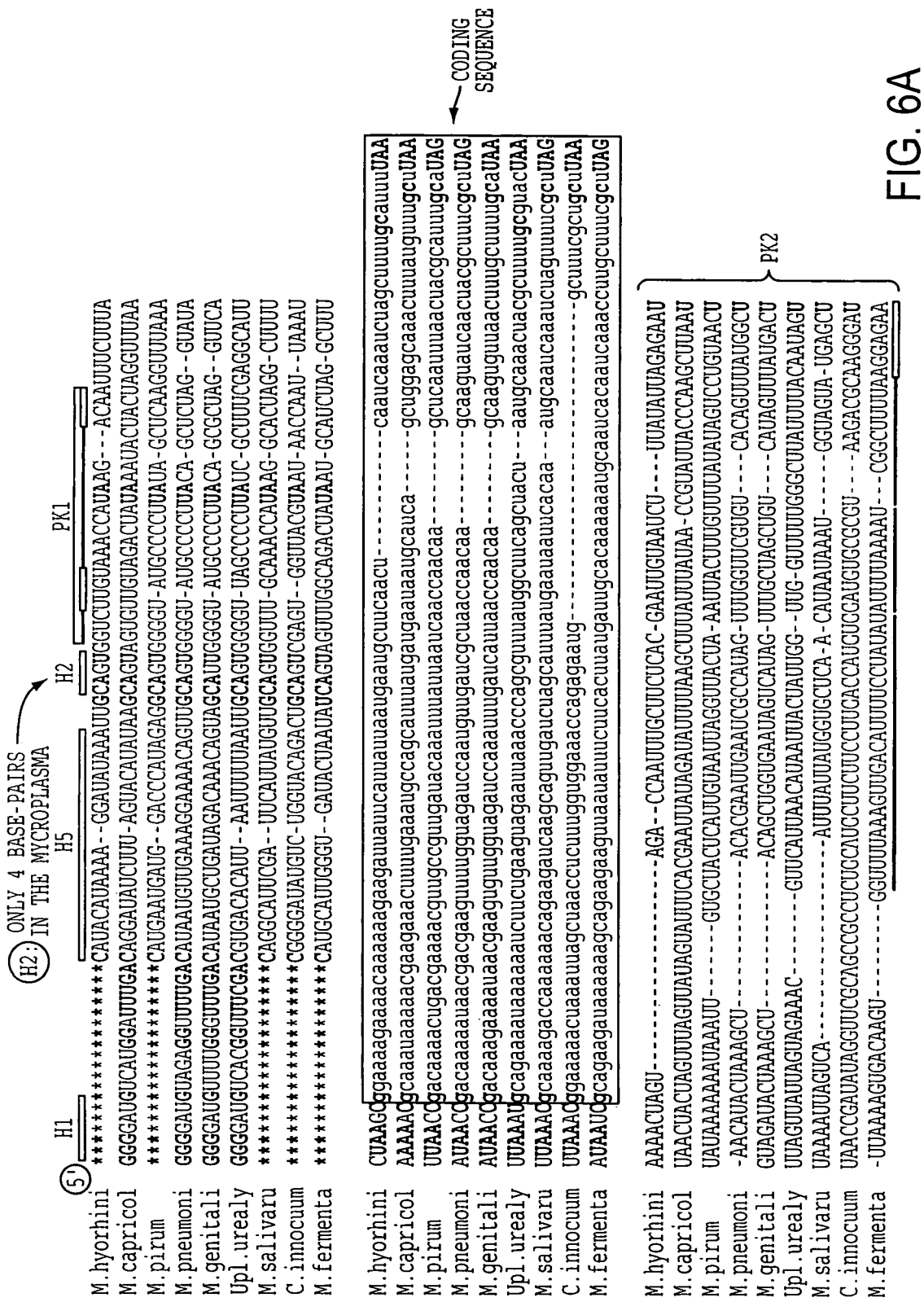
FIGS. 6A and 6B show the sequence alignment, structural domains and structural features for the tmRNA of several species of *Mycoplasmes*. The tmRNA sequences are set forth in SEQ ID NOs:109-117.
Figure 6B:
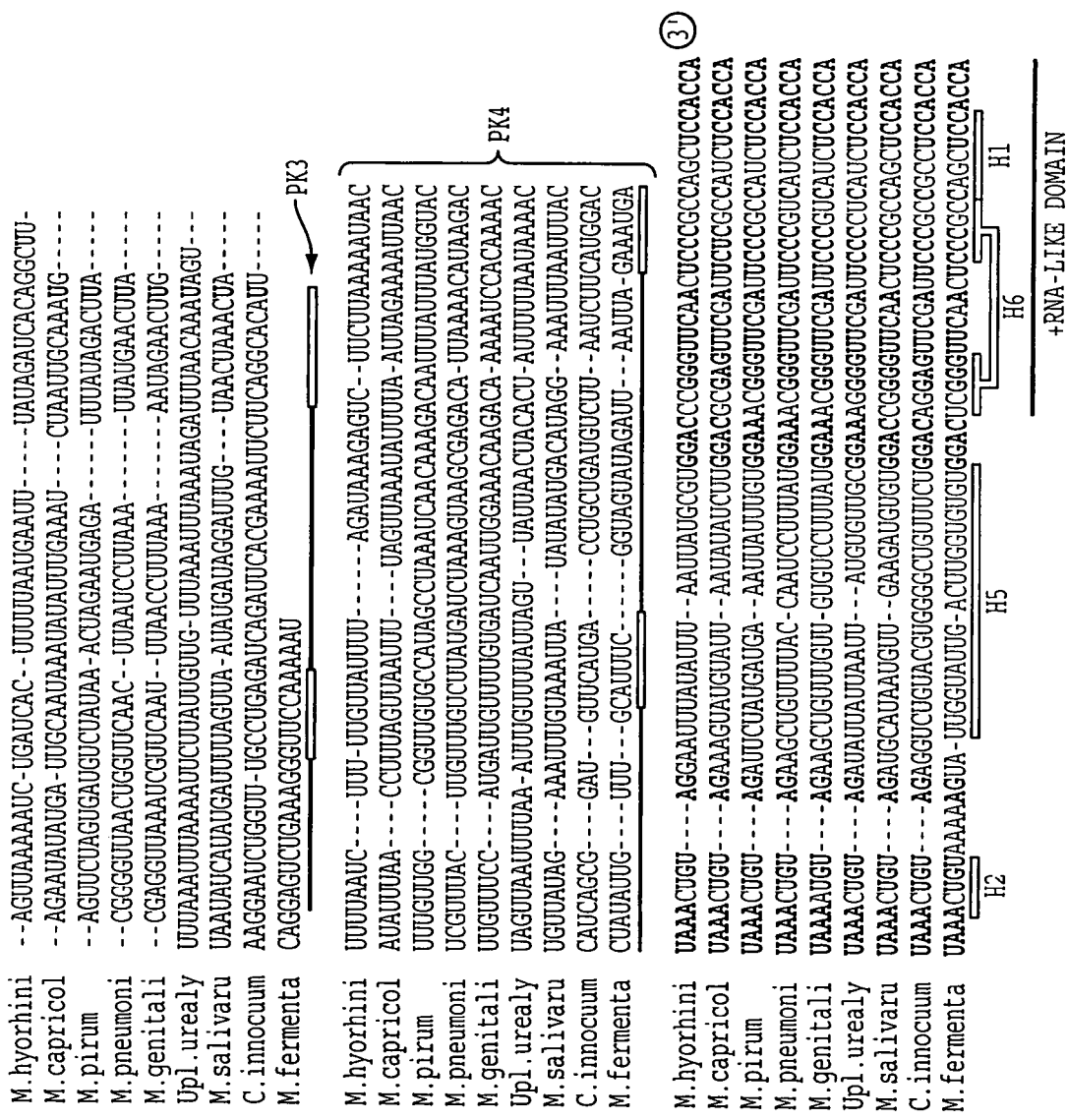
Figures 1, 7A:
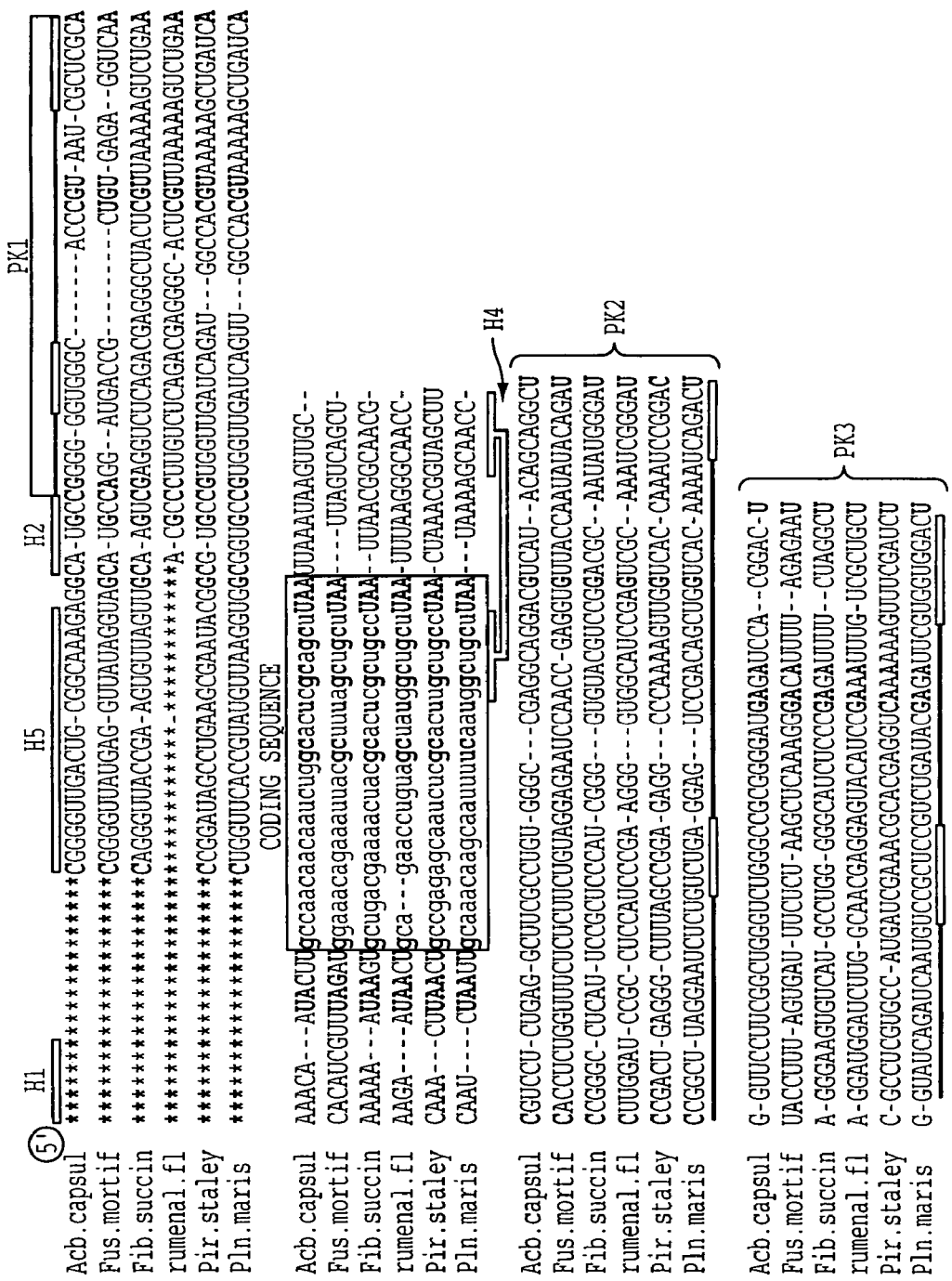
Figure 7C:
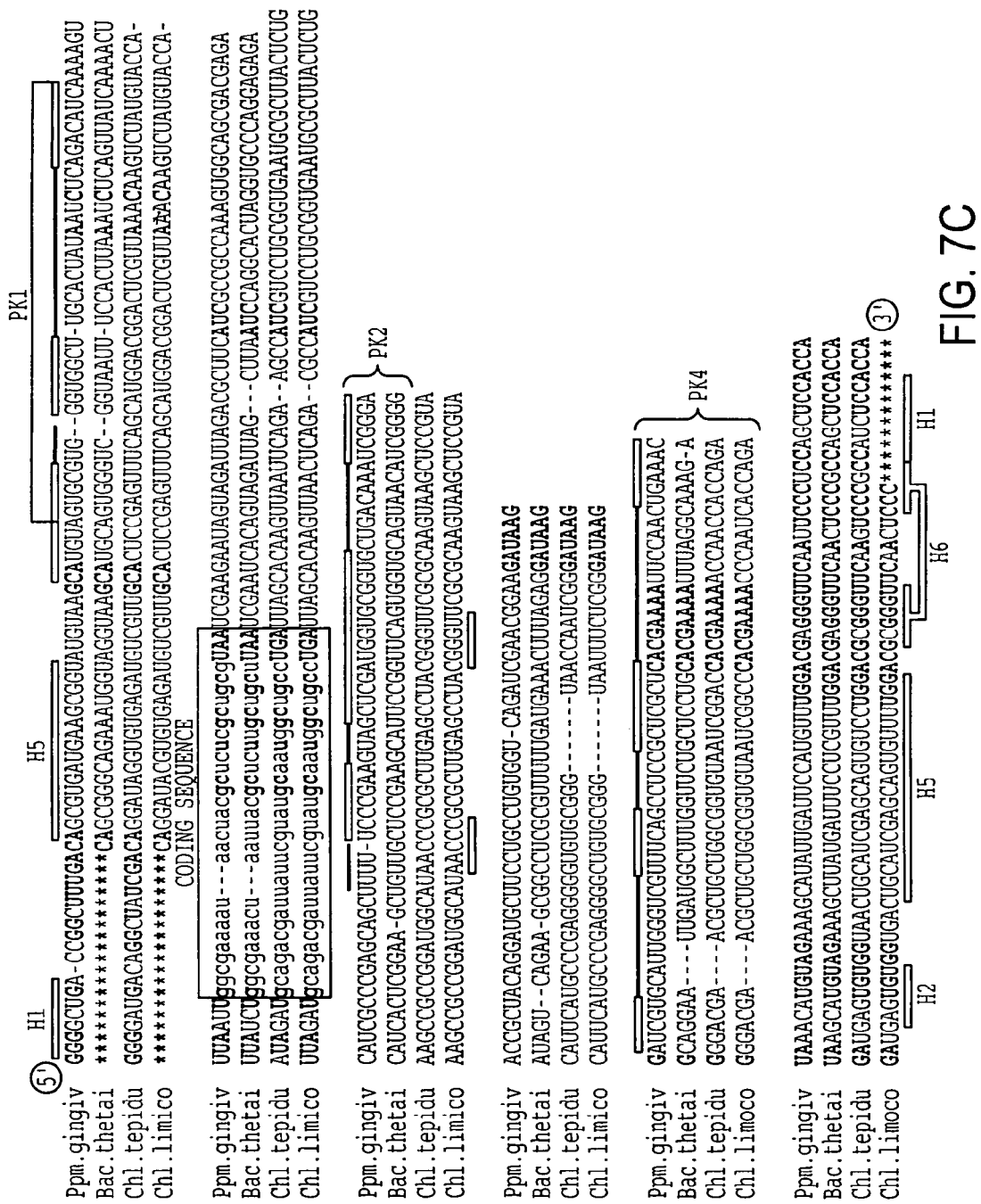
Figure 8A:
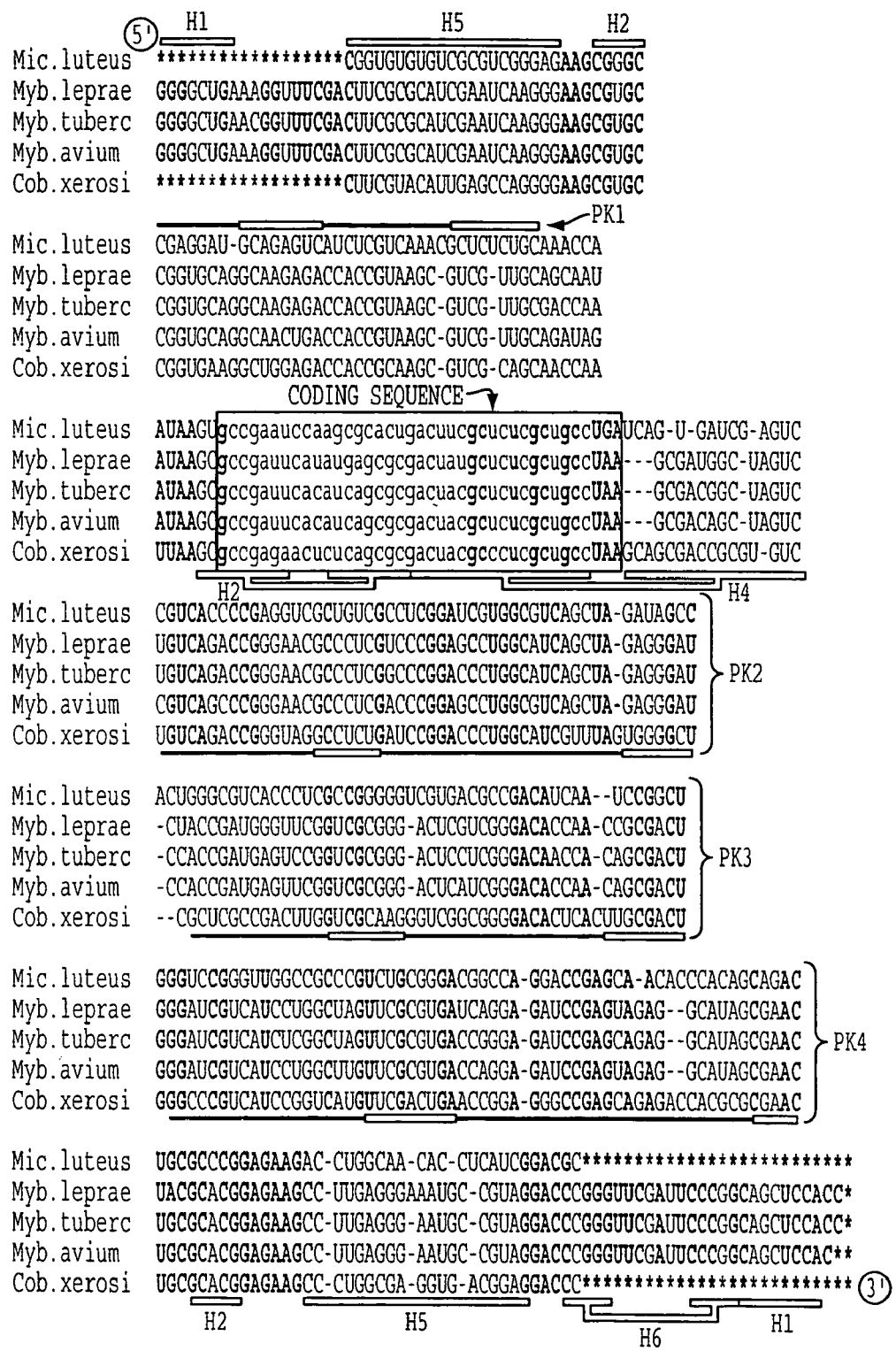
Figure 9A:
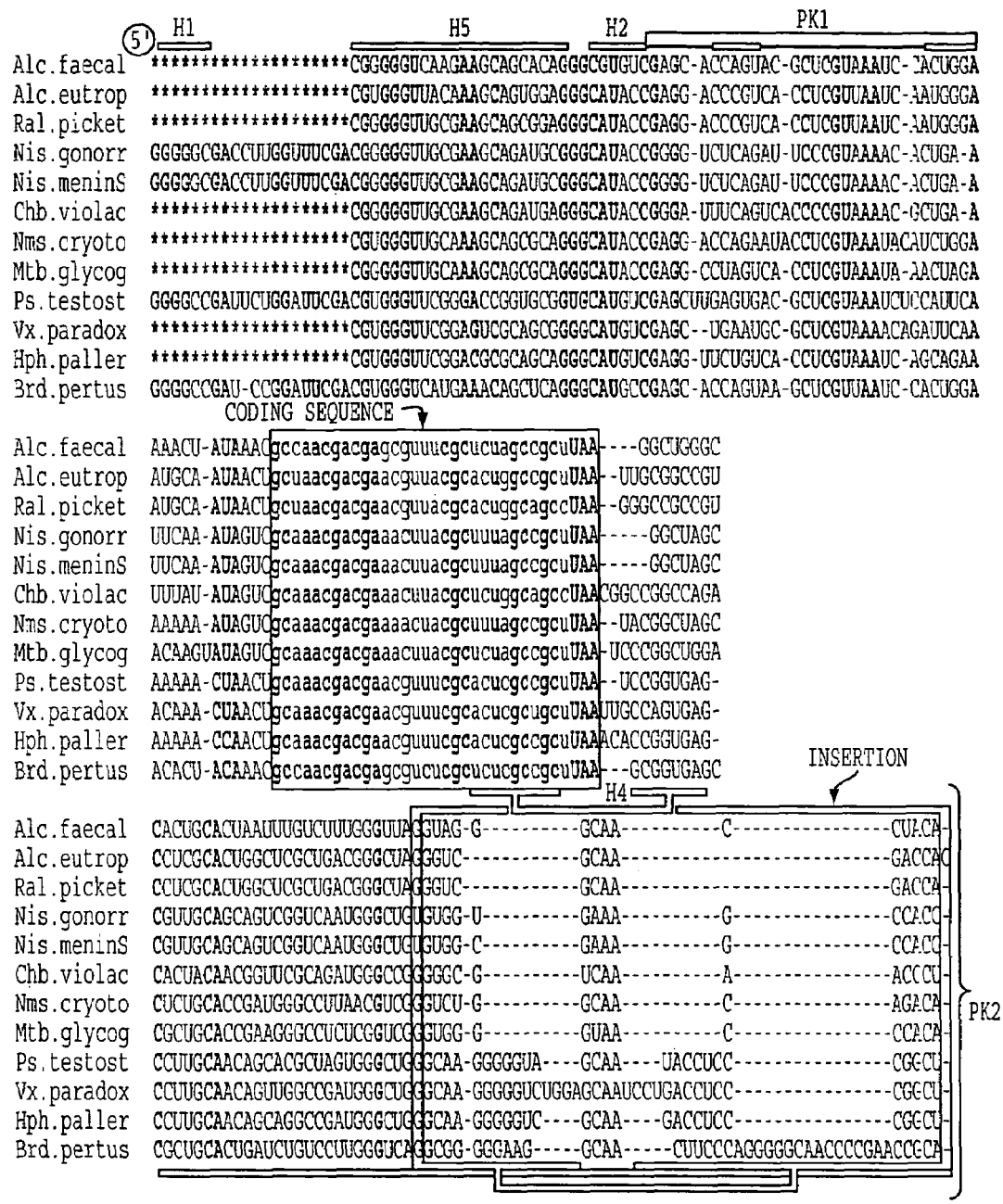
Figure 11A:
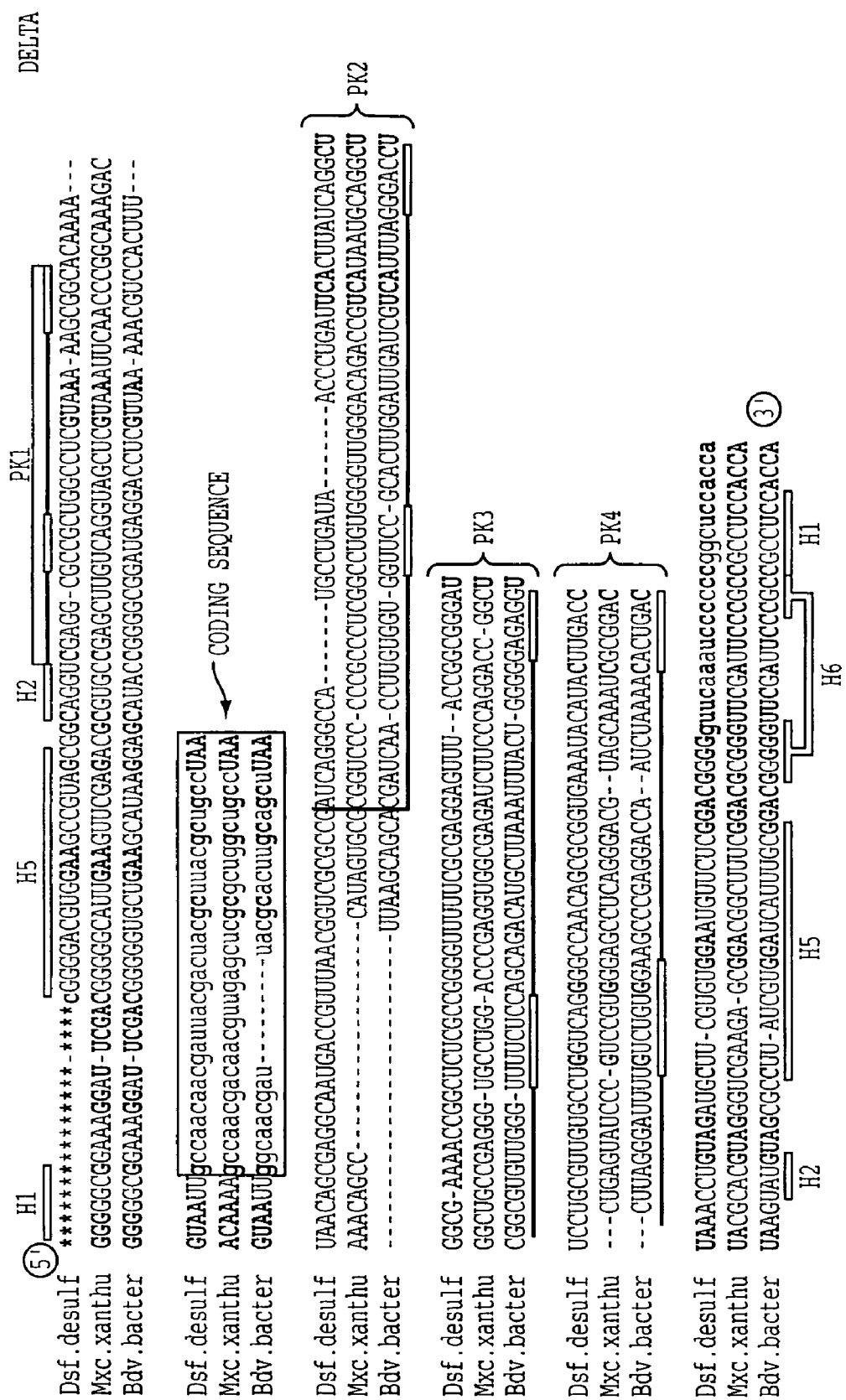
FIGS. 11A and 11B show the sequence alignment, structural domains and structural features for the tmRNA of several species of *Pourpres* delta (11A) and *Pourpres* epsilon (11B). The tmRNA sequences of the *Pourpres* delta are set forth in SEQ ID NOs:170-172, and the tmRNA sequences of the *Pourpres* epsilon are set forth in SEQ ID NOs:173-175.
Figure 11B:
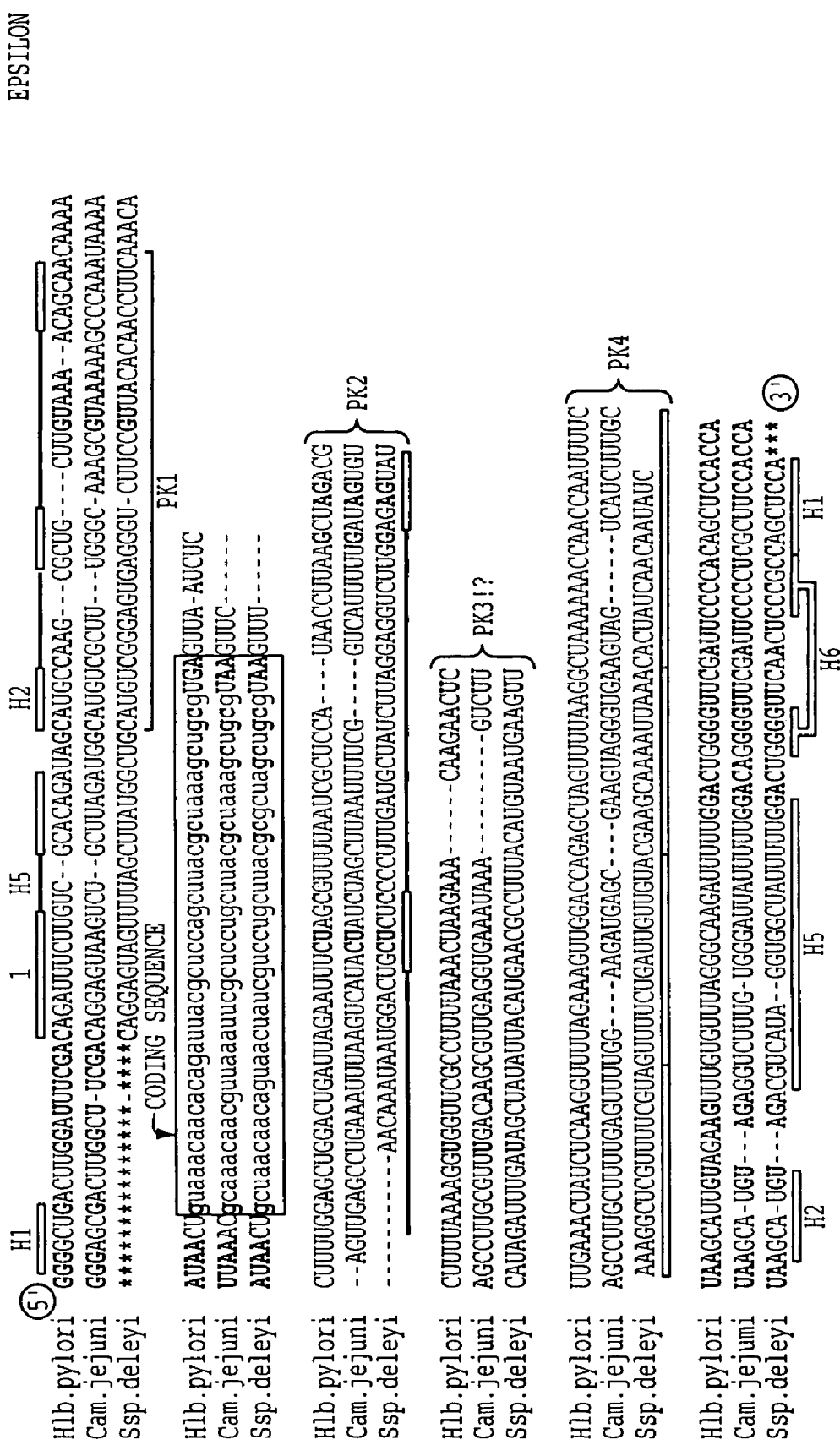

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1-58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tumefaciens*, *Bartonella henselae*, *Bartonella quintana*, *Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1 tmDNA Sequence for *Acidobacterium capsulatum* (Acidobacterium)

GGGGGCGGAAAGGATTCGACGGGGTTGACTGCGGCAAAGAGGCATGCCGG

GGGGTGGGCACCCGTAATCGCTCGCAAAACAATACTTGCCAACAACAATC

TGGCACTCGCAGCTTAATTAAATAAGTTGCCGTCCTCTGAGGCTTCGCCT

GTGGGCCGAGGCAGGACGTCATACAGCAGGCTGGTTCCTTCGGCTGGGTC

TGGGCCGCGGGGATGAGATCCACGGACTAGCATTCTGCGTATCTTGTCGC

TTCTAAGCGCAGAGTGCGAAACCTAAAGGAATGCGACTGAGCATGGAGTC

TCTTTTCTGACACCAATTTCGGACGCGGGTTCGATTCCCGCCGCCTCCAC

CA (SEQ ID NO:9)

TABLE 2 tmDNA Sequence for *Coprothermobacter proteolyticus* (60 degrees)

GGGGGCGGAAAGGATTCGACGGGGAGTCGGAGCCTTGAGCTGCAGGCAGG

GTTGGCTGCCACACCTTAAAAAGGGTAGCAAGGCAAAAATAAATGCCGAA

CCAGAATTTGCACTAGCTGCTTAATGTAAGCAGCCGCTCTCCAAACTGAG

GCTGCATAAGTTTGGAAGAGCGTCAACCCATGCAGCGGCTCTTAAGCAGT

GGCACCAGCTGTTTAAGGGTGAAAAGAGTGGTGCTGGGCAGTGCGGTTGG

TABLE 2-continued tmDNA Sequence for *Coprothermobacter proteolyticus* (60 degrees)

GCTTCCTGGGCTGCACTGTCGAGACTTCACAGGAGGGCTAAGCCTGTAGA
CGCGAAAGGTGGCGGCTCGTCGGACGCGGGTTCGATTCCCGCCGCCTCCA
CCA (SEQ ID NO:10)

TABLE 3 tmDNA Sequence for *Bacteroides thetaiotaomicron* (bacteroides/flavobacterium)

GGGGCTGATTCTGGATTCGACAGCGGGCAGAAATGGTAGGTAAGCATGCA
GTGGGTCGGTAATTTCCACTTAAATCTCAGTTATCAAAACTTTATCTGGC
GAAACTAATTACGCTCTTGCTGCTTAATCGAATCACAGTAGATTAGCTTA
ATCCAGGCACTAGGTGCCAGGACGAGACATCACTCGGAAGCTGTTGCTCC
GAAGCATTCCGGTTCAGTGGTGCAGTAACATCGGGGATAGTCAGAAGCGG
CCTCGCGTTTTTGATGAAACTTTAGAGGATAAGGCAGGAATTGATGGCTT
TGGTTCTGCTCCTGCACGAAAATTTAGGCAAAGATAAGCATGTAGAAAGC
TTATGATTTCCTCGTTTGGACGAGGGTTCAACTCCCGCCAGCTCCACCA
(SEQ ID NO:11)

TABLE 4 tmDNA Sequence for *Dictyoglomus thermophilum* (70 degrees)

GGGGCTGATTCTGGATTCGACAGGGAGTACAAGGATCAAAAGCTGCAAGC
CGAGGTGCCGTTACCTCGTAAAACAACGGCAAAAAAGAAGTGCCAACACA
AATTTAGCATTAGCTGCTTAATTTAGCAGCTACGCTCTTCTAACCCGGGC
TGGCAGGGTTAGAAGGGTGTCATAATGAGCCAGCTGCCCCTTCCGACTCC
CCTAAGGAAGGGAAAGATGTAGGGGATAGGTGCTTACAGAATCCTGCGGG
AGGGAGTCTGTAAGTGCCGAAAAGTTAAAACTCCCGCTAAGCTTGTAGAG
GCTTTTGATTCTTGCTCTCTGGACGCGGGTTCAACTCCCGCCAGCTCCAC
CA (SEQ ID NO:12)

TABLE 5 tmDNA Sequence for Environmental Sample from Rumenal Fluid

ACGCCCTTGTCTCAGACGAGGGCACTCGTTAAAAAGTCTGAAAAGAATAA
CTGCAGAACCTGTAGCTATGGCTGCTTAATTTAAGGGCAACCCTTGGATC
CGCCTCCATCCCGAAGGGGTGGCATCCGAGTCGCAAATCGGGATAGGATG
GATCTTGGCAACGAGGAGTACATCCGAAATTTGTCGCTGCTGGCTGAAGC
ATCGCCGTTCCTCTTTGGGCGTGGCAAGGCAAGATTAAATTCAGAGGATA
AGCGTGTAGTAGCGAGTGAGTAGGTGTTTTTGGACGCGGGTTCAAGTCCC
GCCATCTCCACCA (SEQ ID NO:13)

TABLE 6 tmDNA Sequence for Environmental Sample from Sludge

GGGGATGTCATGGTTTTGACAGGGAACCAGGAGGTGTGAGATGCATGCCG
GAGACGCTGTCCGCTCCGTTATCAAGCAGCAAACAAAACTAATTGCAAAC
AACAATTACTCCTTACCAGCGTAAGCAGCTAACGTTCAACCTCTCCGGAC
CGCCGGGAGGGATTTGGGCGTCGAAACAGCGCGGACGCTCCGGATAGGA
CGCCCATAATATCCGGCTAAGACCATGGGTCTGGCTCTCGCGGGTCTGAT
TGTCTTCCACCGCGCGGGCCGCGATCAAAGACAACTAAGCATGTAGGTTC
TTGCATGGCCTGTTCTTTGGACGCGGGTTCGATTCCCGCCATCTCCACCA
(SEQ ID NO:14)

TABLE 7 tmDNA Sequence for *Fibrobacter succinogenes* (Fibrobacter)

GGGGCTGATTCTGGATTCGACAGGGTTACCGAAGTGTTAGTTGCAAGTCG
AGGTCTCAGACGAGGGCTACTCGTTAAAAAGTCTGAAAAAAATAAGTGC
TGACGAAAACTACGCACTCGCTGCCTAATTAACGGCAACGCCGGGCCTCA
TTCCGCTCCCATCGGGGTGTACGTCCGGACGCAATATGGATAGGGAAGT
GTCATGCCTGGGGCATCTCCCGAGATTTTCTAGGCTGGTCAAACTCCGC
GCCGACCTTCTTGGGCGTGGATAAGACGAGATCTTAAATTCGAAGGGAAC
ACTTGTAGGAACGTACATGGACGTGATTTTGGACAGGGGTTCAACTCCCG
CCAGCTCCA (SEQ ID NO: 15)

TABLE 8 tmDNA Sequence for *Fusobacterium mortiferum*

GGGGCTGATTCTGGATTCGACGGGGTTATGAGGTTATAGGTAGCATGCCA
GGATGACCGCTGTGAGAGGTCAACACATCGTTTAGATGGAAACAGAAATT
ACGCTTTAGCTGCTTAATTAGTCAGCTCACCTCTGGTTTCTCTCTTCTGT
AGGAGAATCCAACCGAGGTGTTACCAATATACAGATTACCTTTAGTGATT
TCTCTAAGCTCAAAGGGACATTTTAGAGAATAGCTTCAGTTAGCCCTGTC
TGCGGGAGTGATTGTTGCGAAATAAAATAGTAGACTAAGCATTGTAGAAG
CCTATGGCGCTGGTAGTTTCGGACACCGGTTCAACTCCCGCCAGCTCCAA
(SEQ ID NO:16)

TABLE 9 tmDNA Sequence for *Corynebacterium xerosis* (gram +, high G-C content)

GGGGGTGATTCTGGATTCGACTTCGTACATTGAGCCACGGOAAGCGTGCC
GGTGAAGGCTGGAGACCACCGCAAGCGTCGCAGCAACCAATTAAGCGCCG
AGAACTCTCAGCGCGACTACGCCCTCGCTGCCTAAGCAGCGACCGCGTGT
CTGTCAGACCGGGTAGGCCTCTGATCCGGACCCTGGCATCGTTTAGTGGG

TABLE 9-continued tmDNA Sequence for *Corynebacterium xerosis*
(gram +, high G-C content)

GCTCGCTCGCCGACTTGGTCGCAAGGGTCGGCGGGGACACTCACTTGCGA
CTGGGCCCGTCATCCGGTCATGTTCGACTGAACCGGAGGGCCGAGCAGAG
ACCACGCGCGAACTGCGCACGGAGAAGCCCTGGCGAGGTGACCGAGGACC
CGGGTTCAACTCCCGCCAGCTCCACCA (SEQ ID NO:17)

TABLE 10 tmDNA Sequence for *Micrococcus luteus* (parfait)

GGGGCTATTCTGGATTCGACGGTGTGTGTCGCGTCGGGAGAAGCGGGCCG
AGGATGCAGAGTCATCTCGTCAAACGCTCTCTGCAAACCAATAAGTGCCG
AATCCAAGCGCACTGACTTCGCTCTCGCTGCCTGATCAGTGATCGAGTCC
GTCACCCCGAGGTCGCTGTCGCCTCGGATCGTGGCGTCAGCTAGATAGCC
ACTGGGCGTCACCCTCGCCGGGGGTCGTGACGCCGACATCAATCCGGCTG
GGTCCGGGTTGGCCGCCCGTCTGCGGGACGGCCAGGACCGAGCAACACCC
ACAGCAGACTGCGCCCGGAGAAGACCTGGCAACACCTCATCGGACGCGGG
TTCAACTCCCGCANTCCCACCA (SEQ ID NO:18)

TABLE 11 tmDNA Sequence for *Mycobacterium smegmatis*

TCATCTCGGCTTGTTCGCGTGACCGGGAGATCCGAGTAGAGACATAGCGA
ACTCCGCACGGAGAGGGGCTGATTCCTGGATTCGACTTCGAGCATCGAAT
CCACGGAAGCGTGCCGGTGCAGGCAAGAGACCACCGTAAGCGTCGTTGCA
ACCAATTAAGCGCCGATTCCAATCAGCGCGACTACGCCCTCGCTGCCTAA
GCGACGGCTGGTCTGTCAGACCGGGAGTGCCCTCGGCCCGGATCCTGGCA
TCAGCTAGAGGGACCCACCCACGCCTTCGCTCGCGGGACCTGTGGGGACA
TCAAACAGCGACTGGGATCGAGCCTCGAGGACATGCCGTAGGACCCGGGT
TCAACTCCCGCCAGCTCCACCA (SEQ ID NO:19)

TABLE 12 tmDNA Sequence for *Bacillus badius*

GGGGGTGATTCTGGATTCGACAGGCATAGTTCGAGCTTGGGCTGCGAGCC
GGAGGGCCGTCTTCGTACCAACGCAAACGCCTAAATATAACTGGCAAAAA
AGATTTAGCTTTAGCTGCCTAATATAGGTTCAGCTGCTCCTCCCGCTATC
GTCCATGTAGTCGGGTAAGGGGTCCAAACTTAGTGGACTACGCCGGAGTT
CTCCGCCTGGGGACAAAGGAAGAGATCAATCAGGCTAGCTGCCCGGACCC
CCGTCGATAGGCAAAAGGAACAGTGAACCCCAAATATATCGACTACGCTC
GTAGACGTTCAAGTGGCGTTATCTTTGGACGTGGGTTCAACTCCCGCCAG
CTCCA (SEQ ID NO:20)

TABLE 13 tmDNA Sequence for *Bacillus brevis*

GGGGGCGGAAAGGATTCGACGGGGATGGTAGAGCATGAGAAGCGAGCCGG
GGGGTTGCCGACCTCGTCACCAACGCAAACGCCATTAACTGGCAACAAAC
AACTTTCTCTCGCTGCTTAATAACCACTGAGGCTCTCCCACTGCATCGGC
CCGTGTGCCCTGGATAGGGCTCAACTTTAACGGGCTACGCCGCAGGCTTC
CGCCTGGAGCCAAAGGAAGAAGACCAATCAGGCTAGGTGCCAGGTCAGCG
CGTCACTCCGCGAATCTGTCACCGAAACTCTAAACGAGTGACTGCGCTCG
GAGATGCTCATGTATCGCTGTTTTCGGACGGGCGTTCGATTCCCGCCGCC
TCACCCA (SEQ ID NO:21)

TABLE 14 tmDNA Sequence for *Bacillus thermoleovorans*
(50-60 degres)

GGGGGCGGAAAGGATTCGACGGGGGTAGGTCGAGCTTAAGCGGCGAGCCG
AGGGGGACGTCCTCGTAAAAACGTCACCTAAAGATAACTGGCAAACAAAA
CTACGCTTTAGCTGCCTAATTGCTGCAGCTAGCTCCTCCCGCCATCGCCC
GCGTGGCGTTCGAGGGGCTCATATGGAGCGGGCTACGCCCAAATCCGCCG
CCTGAGGATGAGGGAAGAGACGAATCAGGCTAGCCGCCGGGAGGCCTGTC
GGTAGGCGGAACGGACGGCGAAGCGAAATATACCGACTACGCTCGTAGAT
GCTTAAGTGGCGATGCCTCTGCACGTGGGTTCGATTCCCGCCGCCTCCCC
ACCA (SEQ ID NO:22)

TABLE 15 tmDNA Sequence for *Clostridium innocuum*

GGGGGCGGAAAGGATTCGACGGGGATATGTCTGGTACAGACTGCAGTCGA
GTGGTTACCTAATAACCAATTAAATTTAAACGGAAAAACTAAATTAGCTA
ACCTCTTTGGTGGAAACCAGAGAATGGCTTTCGCTGCTTAATAACCGATA
TAGGTTCGCAGCCGCCTCTGCATGCTTCTTCCTTGACCATGTGGATGTGC
GCGTAAGACGCAAGGGATAAGGAATCTGGTTTGCCTGAGATCAGATTCAC
GAAAATTCTTCAGGCACATTCATCAGCGGATGTTCATGACCTGCTGATGT
CTTAATCTTCATGGACTAAACTGTAGAGGTCTGTACGTGGGGCTGTTTCT
GGACAGGAGTTCGATTCCCGCCGCCTCACCACCA (SEQ ID NO:23)

TABLE 16 tmDNA Sequence for *Clostridium lentocellum*

GGGGGCGGAAAGGATTCGACGGGGGTCACATCTACTGGGGCAGCCATCCG
TAGAACGCCGGAGTCTACGTTAAAAGCTGGCACTTAAAGTAAACGCTGAA
GATAATTTAGCAATCGCTGCCTAATTAAGGCGCAGTCCTCCTAGGTCTTC
CGCAGCCTAGATCAGGGCTTCGACTCGCGGATCCTTCACCTGGCAAAGCT
TTGAGCCAACGTGAACACTATGAAGCTACTAAAATCTAGAGCCTGTCTTT

TABLE 16-continued

**tmDNA Sequence for *Clostridium lentocellum***

GGGCGCTAGATGGAGGGAATGTCAAAACAAAGAATATGATGGTAGAGACC

ACGCTATATGGGCTTTCGGACAGGGGTTCGATTCCCGCCGCCTTCACCA (SEQ ID NO:24)

TABLE 17

**tmDNA Sequence for *Clostridium perfringens***

GGGGCTGATTCTGGATTCGACGGGGGTAAGATGGGTTTGATAAGCGAGTC

GAGGGAAGCATGGTGCCTCGATAATAAAGTATGCATTAAAGATAAACGCA

GAAGATAATTTTGCATTAGCAGCTTAATTTAGCGCTGCTCATGCTTGGTG

AATTGGCCAGGGTTGAGAGTAAGGGTCTCATTTAAAAGTGGGGAAGGGAG

GGTAGGAAAGCTTTGAGGTAGGAACGGAATTTATGAAGGTTACCAAAGAG

GAAGTTTGTGTGTGGACGTTCTCTGAGGGAATTTTAAAAGACAAGAGTAC

AGTGGTAGAAAGTGTTACTGGTGTGCTTTCGGAGAGGGCTTGAAGTGGGG

CCACTGCA (SEQ ID NO:25)

TABLE 18

**tmDNA Sequence for *Clostridium stercorarium***

GGGGGCCGAAAGGATTCGACGGGGTTATTGAAGCAAGAGTAGCGGGTAGA

GGATTCTCGTTGGCCTCTTTAAAAAACGAGAGGTAAAAATAAACGCAAAC

AACCATAACTACGCTTTAGCTGCTGCGTAAGTAACACGCAGCCCGTCGGC

CCCGGGGTTCCTGCGCCTCGGGATACCGGCGTCATCAAGGCAGGGAACCA

GCCGGATCAGGCTTCAGGTCCGGTGGGATTTAATGAAGCTACCGACTTAT

AAAGCCTGTCTCTGGGCGTTATAAGAAGGGAATGTCAAAACAGAGACTGC

ACCCGGAGAAGCTCTTGTGGATATGGTTCCGGACACGAGTTCGATTCCCG

CCGCCTCCACCA (SEQ ID NO:26)

TABLE 19

**tmDNA Sequence for *Enterococcus faecium* (sp.)**

GGGGCTGATTATGGATTCGACAGGATNGTTGAGCTTGAATTGCGTTTCGT

AGGTTACGGCTACGTTAAAACGTTACAGTTAAATATAACTGCTAAAAACG

AAAACAATTCTTTCGCTTTAGCTGCCTAAAAACCAGCTAGCGAAGATCCT

CCCGGCATCGCCCATGTGCTCGGGTCAGGGTCCTAATCGAAGTGGGATAC

GCTAAATTTTTCCGTCTGTAAAATTTAGAGGAGCTTACCAGACTAGCAAT

ACAAGAATGCCTGTCACTCGGCACGCTGTAAAGCGAACCTTTAAATGAGT

GTCTATGAACGTAGAGATTTAAGTGGGAATATGTTTTGGACGCGGGTTCA

ACTCCCGCCAGCTCCACCA (SEQ ID NO:27)

TABLE 20

**tmDNA Sequence for *Heliobacillus mobilis* (photosyn/gram+)**

GGGGCTGATTCTGGATTCGACGGGGAACGTGTTTGCTTGGGATGCGAGCC

GGGTTGCCGCCAGGACCGTAAAAAGGGCGGAAGGCTTTAATTGCCGAAGA

TAACTACGCTTTAGCTGCTTAATTGCAGTCTAACCTCTTCTCCTCTGTGC

TCTCGGTGAGGATGTAAGGGGTCATTTAAGAGAGCTGGCTTCGACCAATT

CTCGGAGGTCCAAGCGAGATTTATCGAGATAGCCTGACCAACGCTCTGTC

TGCCGTGCGGAAGGAAGGCGAAATCTAAAACGACAGACTACGCTCGTAGT

GTCCTTTGTGGGCATTTCTTCGGACGCGGGTTCAACTCCCGCCAGCTCCA

CCA (SEQ ID NO:28)

TABLE 21

**tmDNA Sequence for *Heliospirillum gestii***

GGGGCTGATTCTGGATTCGACGGGGAACGTGTTTGCTTAGGACGCGAGCC

GGGTTGCCGCCAGGACCGTAAAAAGGGCGGAAGGCTTTAATTGCCGAAGA

TAACTACGCTTTAGCTGCTTAATTGCAGTCTAACCTCTTCTCCTCTGTGC

TCTCGGTGAGGATGTAAGGGGTCATTTAAGAGAGCTGGCTCGAACCAATT

CTCGGAGGTTCGGGTAAGACTTATCGAGATAGCCTGACCAACGCTCTGTC

TGCCGTGCGGAAGGATGGCGAAATCTAAAACGACAGAATACGCTCGTAGT

GTCCTTTGTGGGCATTTCTTCGGACGCGGGTTCAACTCCCGCCAGCTCCA

CCA (SEQ ID NO:29)

TABLE 22

**tmDNA Sequence for *Lactobacillus acidophilus***

GGGGCTGATTCTGGATTCGACAGGCGTAGACCCGCATTGACTGCGGTTCG

TAGGTTACGTCTACGTAAAAACGTTACAGTTAAATATAACTGCAAATAAC

AAAAATTCTTACGCATTAGCTGCTTAATTTAGCCCATGCGTTGCTCTTTG

TCGGTTTACTCGTGGCTGACACTGAGTATCAACTTAGCGAGTTACGTTTA

ACTACCTCACCTGAATAGTTGAAAAGAGTCTTAGCAGGTTAGCTAGTCCA

TACTAGCCCTGTTATATGGCGTTTTGGACTAGTGAAGTTCAAGTAATATA

ACTATGATCGTAGAGGTCAGTGACGAGATGCGTTTGGACAGCGGGTTCAA

CTCCCGCCAGCTCCACCA (SEQ ID NO:30)

TABLE 23

**tmDNA Sequence for *Staphylococcus epidermidis***

GGGGCTGATTCTGCATTCGACAGGGGTCCCCGAGCTTATTAAGCGTGTGG

AGGGTTGGCTCCGTCATCAACACATTTCGGTTAAATATAACTGACAAATC

AAACAATAATTTCGCAGTAGCTGCGTAATAGCCACTGCATCGCCTAACAG

CATCTCCTACGTGCTGTTAACGCCATTCAACCCTAGTAGGATATGCTAAA

CACTGCCGCTTGAAGTCTGTTTAGATGAAATATAATCAAGCTAGTATCAT

TABLE 23-continued tmDNA Sequence for *Staphylococcus epidermidis*

GTTGGTTGTTTATTGCTTAGCATGATGCGAAAATTATCAATAAACTACAC

ACGTAGAAAGATTTGTATCAGGACCTCTGGACGCGGGTTCAACTCCCGCC

AGCTCCACCA (SEQ ID NO:31)

TABLE 24 tmDNA Sequence for *Streptococcus faecium*

GGGGCTGATTCTGGATTCGACAGGCACAGTTTGAGCTTGAATTGCGTTTC

GTAGGTTACGTCTACGTTAAAACGTTACAGTTAAATATAACTGCTAAAAA

CGAAAACAACTCTTACGCTTTAGCTGCCTAAAAACAGTTAGCGTAGATCC

TCTCCGCATCGCCCATGTGCTCGAGTAAGGGTCTCAAATTTAGTGGGATA

CGTGACAACTTTCCGTCTGTAAGTTGTTAAAGAGATCATCAGACTAGCGA

TACAGAATGCCTGTCACTCGGCAAGCTGTAAAGCGAAACCACAAATGAGT

TGACTATGAACGTAGATTTTTAAGTGGCGATGTGTTTGGACGCGGGTTCA

ACTCCCGCCGTTCCACCA (SEQ ID NO:32)

TABLE 25 tmDNA Sequence for Thermoanaerobacterium
*saccharolyticum* (Bacillus/clostridium)

GGGGTAGTAGAGGTAAAAGTAGCGAGCCGAGGTTCCATCTGCTCGTAAAA

CGGTGGACTTAAATATAAACGCAAACGATAATTTAGCTTACGCTGCTTAA

TTACAAGCAGCCGTTCAACCTTTGATTCCCACATCAAAGGATTGGGCGTC

GATTTAGTGGGGAACTGATTTATCAAAGCTTTGAGATAAATCGGATTTTA

TGAAGCTACCAAAGCAGTTATCCTGTCACTGGGAGAACTGCAGAGGGAAT

GTCAAAACACTGACTGCGCTCGGAGAAGCTTTTACTGTGACACCTTCGGA

CCGGGGTTCAACTCCCGCCAGCTCCACCA (SEQ ID NO:33)

TABLE 26 tmDNA Sequence for *Mycoplasma fermentans*

GGGGCTGATTCTGGATTCGACATGCATTGGGTGATACTAATATCAGTAGT

TTGGCAGACTATAATGCATCTAGGCTTTATAATCGCAGAAGATAAAAAG

CAGAAGAAGTTAATATTTCTTCACTTATGATTGCACAAAAAATGCAATCA

CAATCAAACCTTGCTTTCGCTTAGTTAAAAGTGACAAGTGGTTTTAAAGT

TGACATTTTCCTATATATTTTAAAATCGGCTTTTAAGGAGAACAGGAGTC

TGAAAGGGTTCCAAAAATCTATATTGTTTGCATTTCGGTAGTATAGATTA

ATTAGAAATGATAAACTGTAAAAGTATTGGTATTGACTTGGTGTGTGGA

CTCGGGTTCAACTCCCGCCAGCTCCACCA (SEQ ID NO:34)

TABLE 27 tmDNA Sequence for *Mycoplasma hyorhinis*

GGGGCTGATTCTGGATTCGACATACATAAAAGGATATAAATTGCAGTGGT

CTTGTAAACCATAAGACAATTTCTTTACTAAGCGGAAAAGAAAACAAAAA

AGAAGATTATTCATTATTAATGAATGCTTCAACTCAATCAAATCTAGCTT

TTGCATTTTAAAAAACTACTAGACCAATTTGCTTCTCACGAATTGTAATC

TTTATATTAGAGAATAGTTAAAAATCTGATCACTTTTTAATGAATTTATA

GATCACAGGCTTTTTTAATCTTTTTGTTATTTTAGATAAAGAGTCTTCTT

AAAAATAACTAAACTGTAGGAATTTATATTTAATTATGCGTGGACCCGGG

TTCAACTCCCGCCAGCTCCACCA (SEQ ID NO:35)

TABLE 28 tmDNA Sequence for *Mycoplasma pirum*

GGGGAGTCATGGTTTTGACATGAATGATGGACCCATAGAGGCAGTGGGGT

ATGCCCCTTATAGCTCAAGGTTTAAATTAACCGACAAAACTGACGAAAAC

GTTGCCGTTGATACAAATTTATTAATCAACCAACAAGCTCAATTTAACTA

CGCATTTGCATAGTATAAAAAAATAAATTGTGCTACTCATTGTAATTAGG

TTACTAAATTACTTTGTTTTATATAGTCCTGTAACTAGTTCTAGTGATGT

CTATAAACTAGAATGAGATTTATAGACTTATTTGTTGGCGGTTGTGCCAT

AGCCTAAATCAACAAAGACAATTTATTTATGGTACTAAACTGTAGATTCT

ATGATGAAATTATTTGTGGAAACGGCTTCGATTCCCGCCATCTCCACCA (SEQ ID NO:36)

TABLE 29 tmDNA Sequence for *Mycoplasma salivarium*

GGGGCTGATTCTGGATTCGACAGGCATTCGATTCATTATGTTGCAGTGGT

TTGCAAACCATAAGGCACTAGGCTTTTTTAAACGCAAAAGACCAAAAAAC

AGAAGATCAAGCAGTTGATCTAGCATTTATGAATAATTCACAAATGCAAT

CAAATCTAGTTTTCGCTTAGTAAAATTAGTCAATTTATTATGGTGCTCAA

CATAATAAATGGTAGTATGAGCTTAATATCATATGATTTTAGTTAATATG

ATAGGATTTGTAACTAAACTATGTTATAGAAATTTGTAAATTATATATAT

GACATAGGAAATTTAATTTACTAAACTGTAGATGCATAATGTTGAAGATG

TGTGGACCGGGGTTCAACTCCCGCCAGCTCCACCA (SEQ ID NO:37)

TABLE 30 tmDNA Sequence for *Herpetosiphon aurantiacus*

GGGGGCGGAAAGGATTCGACGGGGAGGGCCAATCGTAAGTGGCAAGCCGA

GACGCTGAGCCTCGTTAAATCGGCAACGCCATTAACTGGCAAAAACACTT

TCCGCGCTCCTGTAGCGCTTGCTGCCTAATTAAGGCAACACGTCTCTACT

AGCCTCAGCCCGATGGGCTTGTAGCGGCGACACTTAGTCGGGTCGCTCCC

TABLE 30-continued tmDNA Sequence for *Herpetosiphon aurantiacus*

CTAGTTATGTCTGTGGGCTAGGGGCTAAGATTAACAGGCTGGTCGTGGCC

CGCTTTGTCTATCGGGTGGTGCACCGATAAGATTTAATCAATAGACTACG

CTTGTAGATGCTTGCGGTTTAACTTTTTGGACGCGGGTTCGATTCCCGCC

GCCTCACCACCA (SEQ ID NO:38)

TABLE 31 tmDNA Sequence for *Thermomicrobium roseum*
(352 nts, temp. 70 degrees, green non sulfur)

GGGGCTGATTCTGGATTCGACAGGGCCGTAGGTGCGAGGATTGCAGGTCG

AGGTCGCCCACGAACTCGTAAAAAGGGGCAGCCAAGTAACTGGCGAGCGC

GAACTCGCTCTGGCTGCGTAATTCACGCAGCCACGTCTGCCCGGACCCTT

CCCTGGTGGGTTCGGAGCGGGCGCCGCAAGACCGGGGTGCCCCTGGCCCA

AGCGCCGGTGCGGGCCAGGTCAAGCGTGATCCGGCTCGGCTGACCGGGAT

CCTGTCGGTGGGAGCCTGGCAGCGACAGTAGAACACCGACTAAGCCTGTA

GCATATCCTCGGCTGAACGCTCTGGACGCGGGTTCAACTCCCGCCAGCTC

CACCA (SEQ ID NO:39)

TABLE 32 tmDNA Sequence for *Chlorobium limicola*

GGGGCTGATTCTGGATTCGACAGGATACGTGTGAGATGTCGTTGCACTCC

GAGTTTCAGCATGGACGGACTCGTTAAACAAGTCTATGTACCATTAGATG

CAGACGATTATTCGTATGCAATGGCTGCCTGATTAGCACAAGTTAACTCA

GACGCCATCGTCCTGCGGTGAATGCGCTTACTCTGAAGCCGCCGGATGGC

ATAACCCGCGCTTGAGCCTACGGGTTCGCGCAAGTAAGCTCCGTACATTC

ATGCCCGAGGGGCTGTGCGGGTAATTTCTCGGGATAAGGGGACGAACGCT

GCTGGCGGTGTAATCGGCCCACGAAAACCCAATCACCAGAGATGAGTGTG

GTGACTGCATCGAGCAGTGTTTTGGACGCGGGTTCAACTCCCGCCAGCTC

CACCA (SEQ ID NO:40)

TABLE 33 tmDNA Sequence for *Pirellula staleyi*
(planctomyces)

GGGGCTGATTCTGGATTCGACCGGATAGCCTGAAGCGAATACGGCGTGCC

GTGGTTGATCAGATGGCCACGTAAAAAGCTGATCACAAACTTAACTGCCG

AGAGCAATCTCGCACTTGCTGCCTAACTAAACGGTAGCTTCCGACTGAGG

GCTTTAGCCGGAGACGCCCAAAAGTTGGTCACCAAATCCGGACCGCCTCG

TGCCATGATCGAAACGCACGAGGTCAAAAAAGTTTCGATCTAGTGCAGGG

TGTAGCCAGCAGCTAGGCGACAAACTGTGCAAAAATCAAATTTTCTGCTA

TABLE 33-continued tmDNA Sequence for *Pirellula staleyi*
(planctomyces)

CGCACGTAGATGTGTTCGTGAAAATGTCTCGGCACGGGGGTTCAACTCCC

GCCACTCCACCA (SEQ ID NO:41)

TABLE 34 tmDNA Sequence for *Planctomyces limnophilus*

GGGGCTGATTCTCGATTCGACAACCTCTCAAGAGGAGCGTGGCCACTATG

GGACTCGATTATGTTGAATTCGTCATGGATCTTGAAGAGACCTTCGACAT

CAAACTGGATGACAAACATTTTTCAGCAGTCAAAACACCACGCGATTTGG

CAATCATTATTCGGGATCAATTAGCTGCTGAAGGCAGAATCTGGGATGAA

TCGAATGCTTTTCGCAAAATCTCGAATTTGAATTGGACGATGTTGCCCGA

GTTCCGCATGTGGACTCAAATCAAAAGCTCTCTACCACTTTCTTTTCACC

GACTGCGTCCCAGCACCCGTCTCGTTCAACTCCCGCCANTCCACCA (SEQ ID NO:42)

TABLE 35 tmDNA Sequence for *Planctomyces maris*

GGGGCTGATTCTGGATTCGACTGGTTCACCGTATGTTAAGGTGGCGGTGC

CGTGGTTGATCAGTTGGCCACGTAAAAAGCTGATCACAATCTAATTGCAA

ACAAGCAATTTTCAATGGCTGCTTAATAAAAGCAACCCCGGCTTAGGAAT

CTCTGTCTGAGGAGTCCGACAGCTGGTCACAAAATCAGACTGGTATCAGA

TCAATGTCCGCTCCGTCTGATACGAGATTCGTGGTCGACTGGTTTCCAAC

AGGCTCTGTTTATCGTGCCCGAAGAAACGAGACTCAAACGATAAAATATG

CACCGTAGAGGCTTTAGCTGAGGGTTCACAGGACGCGGGTTCAACTCCCG

CCAGCTCCACCA (SEQ ID NO:43)

TABLE 36 tmDNA Sequence for *Alcaligenes eutrophus*

GGGGTTCATTCTGGATTCGACGTGGGTTACAAAGCAGTGGAGGGCATACC

GAGGACCCGTCACCTCGTTAATCAATGGGAATGCAATAACTGCTAACGAC

GAACGTTACGCACTGGCCGCTTAATTGCGGCCGTCCTCGCACTGGCTCGC

TGACGGGCTAGGGTCGCAAGACCACGCGAGGTCATTTACGTCAGATAAGC

TCCGGAAGGGTCACGAAGCCGGGCACGAAAACCTAGTGACTCGCCGTCGT

AGAGCGTGTTCGTCCGCGATGCCCCGGTTAAATCAAATGACAGAACTAAG

TATGTAGAACTCTCTGTCGAGGGCTTACGGACGCGGGTTCAACTCCCCCC

AGCTCCACCA (SEQ ID NO:44)

TABLE 37 tmDNA Sequence for *Alcaligenes faecalis*
(beta proteobacteria)

GGGGGCGGAAAGGATTCGACGGGGGTCAAGAAGCAGCACAGGGCGTGTCG

AGCACCAGTACGCTCGTAAATCCACTGGAAAACTATAAACGCCAACCACC

AGCGTTTCGCTCTAGCCGCTTAAGGCTGGGCCACTGCACTAATTTGTCTT

TGGGTTAGGTAGGGCAACCTACAGCAGTGTTATTTACAAAGAATCGAATC

GGTCTCCGCCACGAAGTCCGGTTCTAAAACTTAGTGGATCGCCAAGGAAA

GGCCTGTCAATTGGCATAGTCCAAGGTTAAAACTTAAAATTAATTGACTA

CACATGTAGAACTGTCTGTGGACGGCTTGCGGACGCGGGTTCGATTCCCG

CCGCCTCCACCA (SEQ ID NO:45)

TABLE 38 tmDNA Sequence for *Chromobacterium violaceum*
(beta-purple)

GGGGCTGATTCTGGATTCGACGGGGGTTGCGAAGCAGATGAGGGCATACC

GGGATTTCAGTCACCCCGTAAAACGCTGAATTTATATAGTCGCAAACGAC

GAAACTTACGCTCTGGCAGCCTAACGGCCGGCCAGACACTACAACGGTTC

GCAGATGGGCCGGGGCGTCAAAACCCTGTAGTGTCACTCTACATCTGCT

AGTGCTGTTCCGGGTTACTTGGTTCAGTGCGAAATAATAGGTAACTCGCC

AAAGTCCAGCCTGTCCGTCGGCGTGGCAGAGGTTAAATCCAAATGACACG

ACTAAGTATGTAGAACTCACTGTAGAGGACTTTCCGACGCGGGTTCAACT

CCCGCCAGCTCCACCA (SEQ ID NO:46)

TABLE 39 tmDNA Sequence for *Hydrogenophaga palleroni*
(beta-purple)

GGGGCTGATTCTGGATTCGACGTGGGTTCGGACGCGCAGCAGGGCATGTC

GAGGTTCTGTCACCTCGTAAATCAGCAGAAAAAAACCAACTGCAAACGAC

GAACGTTTCGCACTCGCCGCTTAAACACCGGTGAGCCTTGCAACAGCAGG

CCGATGGGCTGGGCAAGGGGTCGCAAGACCTCCCGGCTGCAAGGTAATT

TACATCGGCTGGTTCTGCGTCGGGCACCTTGGCGCAGGATGAGATTCAAG

GATGCTGGCTTCCCGTTTAGCGTGCCACTGCGCGACTCGGGCGGCGAGAC

CCAAATCAGACGGCTACACATGTAGAACTGCTCGAAAAAGGCTTGCGGAC

GGGGGTTCAACTCCCGCCAGCTCCACCA (SEQ ID NO:47)

TABLE 40 tmDNA Sequence for *Methylobacillus glycogenes*
(beta-purple)

GGGGGCGGAAAGGATTCGACGGGGGTTGCAAAGCAGCGCAGGGCATACCG

AGGCCTAGTCACCTCGTAAATAAACTAGAACAAGTATAGTCGCAAACGAC

GAAACTTACGCTCTAGCCGCTTAATCCCGGCTGGACGCTGCACCGAAGGG

TABLE 40-continued tmDNA Sequence for *Methylobacillus glycogenes*
(beta-purple)

CCTCTCGGTCGGGTGGGGTAACCCACAGCAGCGTCATTAAGAGAGGATCG

TGCGATATTGGGTTACTTAATATCGTATTAAATCCAAGGTAACTCGCCTG

CTGTTTGCTTGCTCGTTGGTGAGCATCAGGTTAAATCAAACAACACAGCT

AAGTATGTAGAACTGTCTGTGGAGGGCTTGCGGACGGGGGTTCGATTCCC

GCCGCCTCACCACCA (SEQ ID NO:48)

TABLE 41 tmDNA Sequence for *Nitrosomonas cryotolerans*
(beta-purple)

GGGGCTGATTCTGGATTCGACGTGGGTTGCAAAGCAGCGCAGGGCATACC

GAGGACCAGAATACCTCGTAAATACATCTGGAAAAAAATAGTCGCAAACG

ACGAAAACTACGCTTTAGCCGCTTAATACGGCTAGCCTCTGCACCGATGG

GCCTTAACGTCGGGTCTGGCAACAGACAGCAGAGTCATTAGCAAGGATCG

CGTTCTGTAGGGTCACTTTACAGAACGTTAAACAATAGGTGACTCGCCTG

CCATCAGCCCGCCAGCTGGCGGTTGTCAGGTTAAATTAAAGAGCATGGCT

AAGTATGTAGAACTGTCTGTAGAGGACTTGCGGACGCGGGTTCAACTCCC

GCCAGTCCACCA (SEQ ID NO:49)

TABLE 42 tmDNA Sequence for *Pseudomonas testosteroni*

GCGGCTGATTCTGGATTCGACGTGGGTTCGGGACCGGTGCGGTGCATGTC

GAGCTTGAGTGACGCTCGTAAATCTCCATTCAAAAAACTAACTGCAAACG

ACGAACGTTTCGCACTCGCCGCTTAATCCGGTGAGCCTTGCAACAGCACG

CTAGTGGGCTGGGCAAGGGGGTAGCAATACCTCCCGGCTGCAAGGGAATT

TTCATTAGCTGGCTGGATACCGGGCTTCTTGGTATTTGGCGAGATTTTAG

GAAGCTGGCTACCCAAGCAGCGTGTGCCTGCGGGGTTTGGGTGGCGAGAT

TTAAAACAGAGCACTAAACATGTAGATCTGTCCGGCGAAGGCTTACGGAC

GCGGGTTCAACTCCCGCCAGCTCCACCA (SEQ ID NO:50)

TABLE 43 tmDNA Sequence for *Raistonia pickettii*
(Burkholderia)

GGGGGCGGAAAGGATTCGACGGGGGTTGCGAAGCAGCGGAGGGCATACCG

AGGACCCGTCACCTCGTTAATCAATGGGAATGCAATAACTGCTAACGACG

AACGTTACGCACTGGCAGCCTAAGGGCCGCCGTCCTCGCACTGGCTCGCT

GACGGGCTAGGGTCGCAAGACCAGCGAGGTCATTTACGTCAGATAAGCTT

TAGGTGAGTCACGGGCCTAGAGACGAAAACTTAGTGAATCGCCGTCGTAG

AGCGTGTTCGTCCGCGATGCGGCGGTTAAATCAAATGACAGAACTAAGTA

TABLE 43-continued tmDNA Sequence for *Raistonia pickettii* (Burkholderia)

TGTAGAACTCTCTGTGGAGGGCTTGCGGACGCGGGTTCGATTCCCGCCGC

CTCACCACCA (SEQ ID NO:51)

TABLE 44 tmDNA Sequence for *Variovax paradoxus* (pseudomonas sp.)

GGGGCTCATTCTGGATTCGACGTGGGTTCGGAGTCGCAGCGGGGCATGTC

GAGCTGAATGCGCTCGTAAAACAGATTCAAACAAACTAACTGCAAACGAC

GAACGTTTCGCACTCGCTGCTTAATTGCCAGTGAGCCTTGCAACAGTTGG

CCGATGGGCTGGGCAAGGGGGTCTGGAGCAATCCTGACCTCCCGGCTGCA

AGGATAACTACATGGGCTGGCTCCGATCCGGGTACCTTGGGTCGGGGCGA

GAAAATAGGGTACTGGCGTCCGGTTTAGCGTGTGACTGCGCGACTCCGGA

AGCGAGACTCAAAACAGATCACTAAACATGTAGAACTGCGCGATGAAGGC

TTGCGGACGGGGGTTCAACTCCCGCCAGCTCCACCA (SEQ ID NO:52)

TABLE 45 tmDNA Sequence for *Bdellovibrio bacteriovorus* (delta proteobactene)

GGGGGCGGAAAGGATTCGACGGGGGTGCTGAAGCATAAGGAGCATACCGG

GGCGGATGAGGACCTCGTTAAAAACGTCCACTTTGTAATTGGCAACGATT

ACGCACTTGCAGCTTAATTAAGCAGCACGATCAACCTTGTGGTGGTTCCG

CACTTGGATTGATCGTCATTTAGGGACCTCGGCGTGTTGGGTTTTCTCCA

GCAGACATGCTTAAATTTACTGGGGGAGAGGTCTTAGGGATTTTGTCTGT

GGAAGCCCGAGGACCAATCTAAAACACTGACTAAGTATGTAGCGCCTTAT

CGTGGATCATTTGCGGACGGGGGTTCGATTCCCGCCGCCTCCACCA (SEQ ID NO:53)

TABLE 46 tmDNA Sequence for *Myxococcus xanthus* (delta proteobacterie)

GGGGGCGGAAACGATTCGACGGGGGCATTGAAGTTCGAGACGCGTGCCGA

GCTTGTCAGGTAGCTCGTAAATTCAACCCGGCAAAGACACAAAAGCCAAC

GACAACGTTGAGCTCGCGCTGGCTGCCTAAAAACACCCCATAGTGCGCGG

TCCCCCCGCCCTCGGCCTGTGGGGTTGGGACAGACCGTCATAATGCAGGC

TGGCTGCCGAGGGTGCCTGGACCCGAGGTGGCGAGATCTTCCCAGGACCG

CCTCTGAGTATCCCGTCCGTGGGAGCCTCAGGGACGTAGCAAATCGCGGA

CTACGCACGTAGGGTCGAAGAGCGGACGGCTTTCGCACGCGGGTTCGATT

CCCGCCGCCTCCACCA (SEQ ID NO:54)

TABLE 47 tmDNA Sequence for *Sulfurospirillum Deleyianum*

GGGGCTGATTCTGGATTCGACAGGAGTAGTTTTAGCTTATGGCTGCATGT

CGGGAGTGAGGGTCTTCCGTTACACAACCTTCAAACAATAACTGCTAACA

ACAGTAACTATCGTCCTGCTTACGCGCTAGCTGCGTAAGTTTAACAAATA

ATGGACTGCTCTCCCCTTTGATGCTATCTTAGGAGGTCTTGGAGAGTATC

ATAGATTTGATAGCTATATTACATGAACGCCTTTACATGTAATGAAGTTA

AAGGCTCGTTTTGCGTAGTTTTCTGATTGTTGTACGAAGCAAAATTAAAC

ACTATCAACAATATCTAAGCATGTAGACGTCATAGGTGGCTATTTTTGGA

CTGCGGGTTCAACTCCCGCCAGCTCCACCA (SEQ ID NO:55)

TABLE 48 tmDNA Sequence for *Chromatium vinosum*

GGGGCTGATTCTGGATTCGACGTGGGTCGCGAAACCTAAGGTGCATGCCG

AGGTGCGGTTGACCTCGTAAAACCCTCCGCAAACTTATAGTTGCCAACGA

CGACAACTACGCTCTCGCTGCTTAATCCCAGCGGGCCTCTGACCGTCACT

TGCCTGTGGGCGGCGGATTCCAGGGGTAACCTCACACAGGATCGTGGTGA

CGGGAGTCCGGACCTGATCCACTAAAACCTAACGGAATCGCCGACTGATC

GCCCTGCCCTTCGGGCGGCAGAAGGCTAAAAACAATAGAGTGGGCTAAGC

ATGTAGGACCGAGGGCAGAGGGCTTGCGGACGCGGGTTCAACTCCCGCCA

GCTCCACCA (SEQ ID NO:56)

TABLE 49 tmDNA Sequence for *Pseudomonas fluorescens* (gamma proteobacteria)

GGGGCTGATTCTGGATTCGACGCCGGTTGCGAACCTTTAGGTGCATGCCG

AGTTGGTAACAGAACTCGTAAATCCACTGTTGCAACTTTCTATAGTTGCC

AATGACGAAACCTACGGGGAATACGCTCTCGCTGCGTAAGCAGCCTTAGC

CCTTCCCTCCTGGTACCTTCGGGTCCAGCAATCATCAGGGGATGTCTGTA

AACCCAAAGTGATTGTCATATAGAACAGAATCGCCGTGCAGTACGTTGTG

GACGAAGCGGCTAAAACTTACACAACTCGCCCAAAGCACCCTGCCCGTCG

GGTCGCTGAGGGTTAACTTAATAGACACGGCTACGCATGTAGTACCGACA

GCAGAGTACTGGCGGACGCGGGTTCAACTCCCGCCAGCTCCACCA (SEQ ID NO:57)

TABLE 50 tmDNA Sequence for *Borrelia afzeli*

GGGGCTGATTCTGGATTCGACTGAAAATGCTAATATTGTAAGTTGCAAGC

AGAGGGAATCTCTTAAAACTTCTAAAATAAATGCAAAAAATAATAACTTT

ACAAGTTCAAACCTTGTAATGGCTGCTTAAGTTAGCAOAGAGTTTTGTTG

AATTTGGCTTTGAGATTCACTTATACTCTTTTAGACATCGAAGCTTGCTT

TABLE 50-continued tmDNA Sequence for *Borrelia afzeli*

AAAAATGTTTTCAAGTTGATTTTTAGGGACTTTTATACTTGAGAGCAATT

TGGCGGTTTGCTAGTATTTCCAAACCATATTGCTTAGTAAAATACTAGAT

AAGCTTGTAGAAGCTTATAGTATTGTTTTTAGGACGCGGGTTCAACTCCC

GCCACTCCACCA (SEQ ID NO:58)

TABLE 51 tmDNA Sequence for *Borrelia crociduarae*

GGGGCTGATTCTGGATTCGACTAAGAACTTTAGTAGCATAAATGGCAAGC

AGAGTGAATCTCTTAAAACTTCTTTAATAAATGCAAAAAATAATAACTTT

ACAAGTTCAGATCTTGTAATGGCTGCTTAATTTAGCAGAGAGTTTTGTTG

GATTTTGCTTTGAGGTTCAACTTATACTCTTTAAGACATCAAAGTATGCC

TAAAAATGTTTCAAGTTGATTTTTAGGGACCTTTAAACTTGAGAGTAATT

TGGTGGTTTGCTTGTTTTCCAAGCCTTATTCCTTTTTCTAAAAATTAGCT

AAGCTTGTAGATATTTATGATATTATTTTTAGGACGCGGGTTCAACTCCC

GCCAGTTCCACCA (SEQ ID NO:59)

TABLE 52 tmDNA Sequence for *Borrelia hermsii*

GGGGCTGATTCTGGATTCGACTAAAAACTTTAGTAGCATAAATTGCAAGC

AGAGGGAATCTCTTAAAACTTCTTTAATAAATGCAAGAAATAATAACTTT

ACAAGTTCAAATCTTGTAATGGCTGCTTAAATTAGCAGAGAGTTCTGCTG

GATTTTGCTTTGAGGTTCAGCTTATACTCTTTTAAGACATCAAAGCTTGC

TTAAAAATATTTCAAGTTCATTTTTAGGGACTTTTAAATTTGAGAGTAAT

TTGGCGGTTTCCTAGTTTTTCCAAACCTTATTACTTAAAGAAAACACTAG

CTAAGCTTCTAGATATTTATGATATTATTTTTAGGACGCGGGTTCAACTC

CCGCCAGCTCCACCA (SEQ ID NO:60)

TABLE 53 tmDNA Sequence for *Borrelia garinii*

GGGGCTGATTCTGGATTCGACTGAAAATGCGAATATTGTAAGTTGCAGGC

AGAGGGAATCTCTTAAAACTTCTAAAATAAATGCAAAAAATAATAACTTT

ACAAGCTCAAACCTTGTAATGGCTGCTTAAGTTAGCAGGGAGTTTCGTTG

AATTTGGCTTTGAGGTTCACTTATACTCTTTTCGATATCGAAGCTTGCTT

AAAAATGTTTTCAAGTTAATTTTTAGGGACTTTTGTACTTGAGAGCAATT

TGGCGGTTTGCTAGTATTTCCAAACCATATTGCTTAAGTAAAATGCTAGA

TAAGCTTGTAGAAGCTTATAATATTGTTTTTAGGACGCGGGTTCAACTCC

CGCCAGTCCACCA (SEQ ID NO:61)

TABLE 54 tmDNA Sequence for *Thermodesulfobacterium commune* (70 degrees)

GGGGGCGGAAAGGATTCGACGGGGATAGGTAGGATTAAACAGCAGGCCGT

GGTCGCACCCAACCACGTTAAATAGGGTGCAAAAACACAACTGCCAACGA

ATACGCCTACGCTTTGGCAGCCTAAGCGTGCTCCCACGCACCTTTAGACC

TTGCCTGTGGGTCTAAAGGTGTGTGACCTAACAGGCTTTGGGAGGCTTAA

TCCGTGGGGTTAAGCCTCCCGAGATTACATCCCACCTGGTAGGGTTGCTT

GGTGCCTGTGACAAGCACCCTACGAGATTTTCCCACAGGCTAAGCCTGTA

GCGGTTTAATCTGAACTATCTCCGGACGCGGGTTCGATTCCCGCCGCCTC

CCCACCA (SEQ ID NO:62)

TABLE 55 tmDNA Sequence for *Thermotoga neapolitana* (Thermotogales)

GGGGGCGGAAAGGATTCGACGGGGATGGAGTCCCCTGGGAAGCGACCCGA

GGTCCCCACCTCCTCGTAAAAAAGGTGGGAACACGAATAAGTGCCAACGA

ACCTGTTGCTGTTGCCGCCTAATAGATAGGCGGCCGTCCTCTCCGGAGTT

GGCTGGGCTCCGGAAGAGGGCGTGAGGGATCCAGCCTACCGATCTCCCCT

CCGCCTTCCGGCCCGGATCCGGAAGGTTCAGCAAGGCTGTGGGAAGCGAC

ACCCTCCCCGTGGGGGTCCTTCCCGACACACGAAACACGGGCTGCGCTC

GGAGAAGCCCAGGGGCCTCCATCTTCNGACGCGGGTTCGATTCCCGCCAC

CTCCACCA (SEQ ID NO:63)

TABLE 56 tmDNA Sequence for *Deinococcus proteolyticus*

GGGGGCGGAAAGGATTCGACGGGGGAACGGAAAGCGCTGCTGCGTGCCGA

GGAGCCGTTGGCCTCGTAAACAAACGGCAAAGCCATTAACTGGCGAAAAT

AACTACGCTCTCGCTGCTTAAGTGAGACAGTGACCACGTAGCCCCGCCTT

TGGCGACGTGTGAACTGAGACAAAAGAAGGCTAGCTTAGGTGAGGTTCCA

TAGCCAAAAGTGAAACAAATGGAAATAAGGCGGACGGCAGCCTGTTTGC

TGGCAGCCCAGGCCCCACAATTTAAGAGCAGACTACGCACGTAGATGCAC

GCTGGATGGACCTTTGGACGCGGGTTCGATTCCCGCCAGCTCCACCA (SEQ ID NO:64)

TABLE 57 tmDNA Sequence for *Prosthecobacter fusiformis* (verrucomicrobia)

GGGGCTGATTCTGGATTCGACGGGGAGTACAAGGATCAAAAGCTGCAAGC

CGAGGTGCCGTTACCTCGTAAAACAACGGCAAAAAAGAAGTGCCAACACA

AATTTAGCATTAGCTGCTTAATTTAGCAGCTACGCTCTTCTAACCCGGGC

TGGCAGGGTTAGAAGGGTGTCATAATGAGCCAGCTGCCCCTTCCGACTCC

TABLE 57-continued tmDNA Sequence for *Prosthecobacter fusiformis* (verrucomicrobia)

CCTAAGGAAGGGAAAGATGTAGGGGATAGGTGCTTACAGAATCCTGCGGG

AGGGAGTCTGTAAGTGCCGAAAAGTTAAAACTCCCGCTAAGCTTGTAGAG

GCTTTTGATTCTTGCTCTCTGGACGCGGGTTCAACTCCCGCCAGCTCCAC

CA (SEQ ID NO:65)

TABLE 58 tmDNA Sequence for *Verrucomicrobium spinosum* (verrucomicrobium)

GGGNNNNATTTGGAATTCGCCGAATGCTAGAAGTGGAGGCTGCATGCCGC

GGATGATTCGTTGGCCGCTTTACCAATTCGGATCAAACAACTAAATGCGG

ACTCTAACGAGCTTGCCCTCGCCGCTTAATTGACGGTGACGTTCCTCCAG

TGAAGTCTGTGAATTGGAGGAGCGACTACTTACAGGCTGGCCAAAAGAGC

GGGCGACCGGCCCCAAGGCGAGATCTACAGGCCGCTGGATGGACGGCATC

CTGGCAGTAGGAGGCTGGACATCGAGATCAAATNATTGCCTGAGCATGGA

GACGCTTTCATAAAGGNGTTCGGACAGGG (SEQ ID NO:66)

Example 4

Alignment of tmRNA Sequences

The newly discovered tmRNA sequences and several known tmRNA sequences were aligned to identify target sites for drug development. The alignments of the sequences are shown in FIGS. 3A-11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in each Phylum that could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133-140.
Ando, H. et al. (1996). *Genes & Genet. Syst.* 71:47-50.
Breithaupt, H. (1999). *Nature Biotechnol.* 17:1165-1169.
Felden, B. et al. (1996). *Biochimie* 78:979-983.
Felden, B. et al. (1997). *RNA* 3:89-103.
Felden, B. et al. (1998). *EMBO J.* 17:3188-3196.
Felden et al. (1999). *Biochim. Biophys. Acta* 1446:145-148.
Gray, M. W. and Spencer, D. F. (1996). In *Evolution of Microbial Life*, Cambridge University Press, pp. 109-126.
Hickerson, R. P. et al. (1998). *J. Mol. Biol.* 279:577-587.
Himeno, H. et al. (1997). *J. Mol. Biol.* 268:803-808.
Huang, C. et al. (2000). *EMBO J.* 19:1098-1107.
Julio, S. M et al. (2000). *J. Bacteriol.* 182:1558-1563.
Keiler, K. C. et al. (1996). *Science* 271:990-993.
Komine, Y. et al. (1994). *Proc. Natl. Acad. Sci. USA* 20:9223-9227.
Mateeva, O. et al. (1997). *Nucleic Acids Res.* 25:5010-5016.
Muto, A. et al. (1998). *Trends Biochem. Sci.* 1:25-29.
Nameki, N. et al. (1999). *J. Mol. Biol.* 286:733-744.
Nakemi, N. et al. (2000). *FEBS Lett.* 470:345-349.
*Remington's Pharmaceutical Sciences,* 18th Ed., Mack Publishing Co., Easton, Pa., 1990.
Tu, G. F. et al. (1995). *J. Biol. Chem.* 270:9322-9326.
Ushida, C. et al. (1994). *Nucleic Acids Res.* 16:3392-3396.
Williams, K. P. (1999). *Nucleic Acids Res.* 27:165-166.
Williams, K. P. and Bartel, D. P. (1996). *RNA* 2:1306-1310.
Wower, J. and Zwieb, C. (1999). *Nucleic Acids Res.* 27:167.
Yang, D. et al. (1985). *Proc. Natl. Acad. Sci. USA* 82:4443-4447.

What is claimed is:

1. An isolated nucleic acid sequence selected from the group consisting of the tmRNA sequence for *Staphylococcus aureus* set forth in SEQ ID NO:86, and the coding sequence thereof consisting of nucleotides 94-129 of SEQ ID NO:86.

2. A method for diagnosing a bacterial infectious agent comprising determining the presence of a bacterial nucleic acid sequence selected from the group consisting of the tmRNA sequence for *Staphylococcus aureus* set forth in SEQ ID NO: NO:86, and the coding sequence thereof consisting of nucleotides 94-129 of SEQ ID NO:86.

3. The method of claim 2, wherein the determination is made by performing an amplification-based assay.

* * * * *